(12) United States Patent
Bernett et al.

(10) Patent No.: US 8,314,213 B2
(45) Date of Patent: Nov. 20, 2012

(54) HUMAN EQUIVALENT MONOCLONAL ANTIBODIES ENGINEERED FROM NONHUMAN VARIABLE REGIONS

(75) Inventors: Matthew J. Bernett, Monrovia, CA (US); Gregory Moore, Monrovia, CA (US); John R. Desjarlais, Pasadena, CA (US)

(73) Assignee: Xencor, Inc., Monrovia, CA (US)

( * ) Notice: Subject to any disclaimer, the term of this patent is extended or adjusted under 35 U.S.C. 154(b) by 588 days.

(21) Appl. No.: 12/426,785

(22) Filed: Apr. 20, 2009

(65) Prior Publication Data

US 2010/0004431 A1 Jan. 7, 2010

Related U.S. Application Data

(60) Provisional application No. 61/046,399, filed on Apr. 18, 2008, provisional application No. 61/115,449, filed on Nov. 17, 2008, provisional application No. 61/120,675, filed on Dec. 8, 2008.

(51) Int. Cl.
   *C07K 16/28* (2006.01)

(52) U.S. Cl. ............................... 530/388.2; 530/388.7

(58) Field of Classification Search ........................ None
   See application file for complete search history.

(56) References Cited

U.S. PATENT DOCUMENTS

| | | | | |
|---|---|---|---|---|
| 5,530,101 | A * | 6/1996 | Queen et al. | 530/387.3 |
| 5,693,762 | A | 12/1997 | Queen | |
| 5,859,205 | A * | 1/1999 | Adair et al. | 530/387.3 |
| 6,797,492 | B2 | 9/2004 | Daugherty | |
| 7,083,784 | B2 | 8/2006 | Dall'Acqua | |
| 7,117,096 | B2 | 10/2006 | Luo | |
| 7,217,798 | B2 | 5/2007 | Hinton | |
| 7,297,334 | B2 | 11/2007 | Baca et al. | |
| 7,317,091 | B2 | 1/2008 | Lazar et al. | |
| 2004/0132101 | A1 | 7/2004 | Lazar | |
| 2005/0054832 | A1 | 3/2005 | Lazar | |
| 2006/0024298 | A1 | 2/2006 | Lazar | |
| 2006/0121032 | A1 | 6/2006 | Dahiyat | |
| 2006/0235208 | A1 | 10/2006 | Lazar | |
| 2007/0148170 | A1 | 6/2007 | Desjarlais | |
| 2007/0275460 | A1 | 11/2007 | Desjarlais | |
| 2008/0167449 | A1 | 7/2008 | Lazar | |

FOREIGN PATENT DOCUMENTS

| | | |
|---|---|---|
| WO | WO 92/11018 | 7/1992 |
| WO | WO 03/025019 A | 3/2003 |
| WO | WO 03/050260 A | 6/2003 |
| WO | WO 2005/014653 A | 2/2005 |
| WO | WO 2005/144653 A | 2/2005 |
| WO | WO 2005/047327 | 5/2005 |
| WO | WO 2005/054273 A | 6/2005 |
| WO | WO 2005/056759 A | 6/2005 |
| WO | WO 2005/079479 A | 9/2005 |
| WO | WO 2006/020114 A | 2/2006 |
| WO | WO 2006/105338 A2 | 10/2006 |
| WO | WO 2006/135793 A | 12/2006 |
| WO | WO 2008/031056 A | 3/2008 |

OTHER PUBLICATIONS

Portolano et al., J Immunol. Feb. 1, 1993;150(3):880-7.*
Eduardo Padlan, Mol Immunol. Feb. 1994;31(3):169-217.*
Antibodies, A laboratory manual, Harlow and Lane, Cold Spring Harbor Laboratory, 1988, p. 28.*
Davies J et al. "Affinity Improvement of Single Antibody VH Domains: Residues in All Three Hypervariable Regions Affect Antigen Binding" 1996, Immunotechnology, Elsevier Sci Pub BV, NL, 2(3):169-179.
Holt L J et al. "Domain Antibodies: Proteins for Therapy" 2003, Trends in Bio, Elsevier Pub, 21(11):484-490.
Presta L G et al. "Humanization of an Anti-Vascular Endothelial Growth Factor Monoclonal Antibody for the Therapy of Solid Tumors and Other Disorders" 1997, Amer Assoc for Cancer Research 57:4593-4599.
Kashmiri, et al., "SDR grafting—a new approach to antibody humanization" 2005, *Methods* 36:25-34.
Kay et al., Phage display of peptides and proteins: a laboratory manual, Academic Press, San Diego, CA, 1996;.
Kim et al., "Analysis of FcγRIII and IgG Fc Polymorphism Reveals Functional and Evolutionary Implications of Protein-Protein Interaction" 2001, J. Mol. Evol. 54:1.
Kim, et al., "The Vascular Endothelial Growth Factor Proteins: Identification of Biologically Relevant Regions by Neutralizing Monoclonal Antibodies" *Growth Factor* (1992), vol. 7, pp. 53-64.
Knappik, et al., "Fully Synthetic Human Combinatorial Antibody Libraries (HuCAL) Based on Modular Consensus Frameworks and CDRs Randomized with Trinucleotides" 2000, *J Mol Biol* 296:57-86.
Knight, et al., "Construction and Initial Characterizaion of a Mouse-Human Chimeric Anti-TNF Antibody" 1993, *Mol Immunol* 30:1443-1453.
Kohler and Milstein, "Continuous cultures of fused cells secreting antibody of predefined specificity" 1975, Nature 256:495.
Lazar, et al., "A molecular immunology approach to antibody humanization and functional optimization" 2007, *Mol Immunol* 44:1986-1998.
Lazikani et al., "Standard Conformations for the Canonical Structures of Immunoglobulins" 1997, J. Mol. Biol. 273: 927-948.
Lefranc, et al., The human IgG subclasses: molecular analysis of structure, function and regulation. Pergamon, Oxford, pp. 43, (1990).
Lefranc, G. et al., "Gm, Am and Km Immunoglobulin Allotypes of Two Populations in Tunisia" 1979, Hum. Genet.: 50, 199.
Li et al., "Optimization of humanized IgGs in glyconengineered Pichia pastoris" 2006, Nature Biotechnology 24(2):210.
Loghem E van, "Allotypic markers", 1986, Monogr Allergy 19: 40.
Lonberg, "Standard Conformations for the Canonical Structures of Immunoglobulins" 2005, *Nat Biotechnol* 23:1117-1125.
U.S. Appl. No. 11/004,590, filed Dec. 3, 2004, Gregory Alan Lazar.
U.S. Appl. No. 11/102,621, filed Apr. 8, 2005, Paul R. Hinton.
U.S. Appl. No. 11/274,065, filed Nov. 14, 2005, Aaron Keith Chamberlain.
U.S. Appl. No. 11/429,793, filed May 8, 2006, Leonard Presta.
U.S. Appl. No. 11/436,266, filed May 17, 2006, Aaron Keith Chamberlain.

(Continued)

*Primary Examiner* — Zachary Skelding
(74) *Attorney, Agent, or Firm* — Morgan Lewis & Bockius LLP; Robin M. Silva, Esq.; Ada O. Wong, Esq.

(57) ABSTRACT

The present invention is directed to the creation of human equivalent CDRs and antibodies containing them by a method of producing an antibody which specifically binds to an antigen.

4 Claims, 42 Drawing Sheets

OTHER PUBLICATIONS

U.S. Appl. No. 11/932,151, filed Oct. 31, 2007, Aaron Keith Chamberlain.
U.S. Appl. No. 12/020,443, filed Jan. 25, 2008, Gregory Alan Lazar.
U.S. Appl. No. 12/156,183, filed May 30, 2008, Seung Yup Chu.
U.S. Appl. No. 12/341,769, Apr. 8, 2005, Paul R. Hinton.
Ashkenazi et al. "Immunoadhesions as research tools and therapeutic agents" 1997, *Curr Opin Immunol* 9:195-200.
Barbie & Lefranc, "The Human Immunoglobulin Kappa Variable (IGKV) Genes and Joining (IGKJ) Segments"1998, *Exp Clin Immunogenet* 15(3): 171-83.
Bruggemann et al., "Production of human antibody repertoires in transgenic mice" 1997, Curr Opin Biotechnol 8:455-458.
Carter, et al. "Potent antibody therapeutics by design" 2006, Nature Reviews Immunology 6:343-357.
Chamow et al., "Immunoadhesins: principles and applications" 1996, *Trends Biotechnol* 14:52-60.
Chothia et al. "Canonical Structures for the Hypervariable Regions of Immunoglobulins" 1987, J. Mol. Biol. 196: 901-917.
Chothia et al., "Canoncial Structures for the Hypervariable Regions of Immunoglobulins" 1989, Nature 342: 877-883.
Clark, "IgG effector mechanisms", Chem Immunol. 1997, 65:88.
Cox et al., "Glycan optimization of a human monoclonal antibody in the aquatic plant Lemna minor" 2006, Nat Biotechnol 24(12):1591.
Dall Acqua et al. "Increasing the Affinity of a Human IgG1 for the Neonatal Fc Receptor: Biological Consequences" Journal of Immunology, 2002, 169:5171-5180.
Dall'Acqua, et al., "Antibody humanization by framework shuffling"2005, *Methods* 36:43-60.
Damschroder, et al., "Framework shuffling of antibodies to reduce immunogenicity and manipulate functional and biophysical properties"2007, *Mol Immunol* 44:3049-3060).
Davies et al., "Expressions of GnTIII in a Recombinant Anti-CD20 CHO Production Cell Line" Epression of Antibodies with Altered Glycoforms Leads to an Increased in ADCC Through Higher Affinity for FcγRIII 2001, Biotechnol Bioeng 74:288.
Davis et al., "Fc receptor homologs: newest members of a remarkably diverse Fc receptor gene family" 2002, *Immunological Reviews* 190:123-136.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody" 2002, J. Immunol. 169:3076.
Gonzales, et al., "SDR grafting of a murine antibody using multiple human germline templates to minimize its immunogenicity" 2004, *Mol Immunol* 41:863-872.
Gorman et al., "Humanisation of monoclonal antibodies for therapy" 1990, Semin Immunol 2(6):457.
Green, et al., " Antigen-specific human monoclonal antibodies from mice engineered with human Ig heavy and light chain YACs" 1994, *Nat Genet* 7:13-21.
Griffiths et al., "Strategies for Selection of Antibodies by phage display" 1998, Curr Opin Biotechnol 9:102-108.
Griffiths, et al., "Isolation of high affinity human antibodies directly from large synthetic repertoires"1994, *Embo J* 13:3245-3260.
Hayhurst et al., "High-throughout antibody isolation" 2001, *Curr Opin Chem Biol* 5:683.
Hinton et al. "An Engineered Human IgG1 Antibody with Longer Serum Half-Life" 2006 Journal of Immunology 176:346.
Hinton et al., "Engineered Human IgG Antibodies with Longer Serum Half-Lives in Primates" 2004, J. Biol. Chem. 279(8): 6213.
Holliger et al, "Engineered antibody fragments and the rise of single domains" 2006, Nature Biotechnology 23(9):1126-1136.
Hwang, et al., "Use of human germline genes in a CDR homology-based approach to antibody humanization"2005, *Methods* 36:35-42.
Jones, et al., "Replacing the complementarity-determining regions in a human antibody with those from a mouse" 1986, *Nature* 321 :522.
Kabat et al., 1991, Sequences of Proteins of Immunological Interest, 5th Ed., United States Public Health Service, National Institutes of Health, Bethesda.
Kaneko et al., "Anti-Inflammatory Activity of Immunoglobulin G Resulting from Fc Sialylation" 2006, Science 313:670.
Kay et al., Phage display of peptides and proteins: a laboratory manual, Academic Press, San Diego, CA, 1996.
Kim, et al., "Analysis of FcgRIII and IgG Fc Polymorphism Reveals Functional and Evolutionary Implications of Protein—Protein Interaction"1992, *Growth Factors* 7:53-64.
Lefranc, et al., The human IgG subclasses: molecular analysis of structure, function and regulation. Pergamon, Oxford, pp. 43.
Lefranc, G. et al., "Gm, Am and Km Immunoglobulin Allotypes of Two Populations in Tunisia" 1979, Hum. Genet.: 50, 199, (1990).
Lonberg, et al., "Antigen-specific human antibodies from mice comprising four distinct genetic modifications" 1994, Nature 368:856-859.
Lowman et al., "Selecting High-Affinity Binding Proteins by Monovalent Phage Display" 1991, *Biochemistry* 30:10832-10838.
Matsuda et al., "The Complete Nucleotide Sequence of the Human Immunoglobulin Heavy Chain Variable Region Locus" 1998, *J Exp Med* 188: 2151-2162.
Maynard et al., "Anitbody Engineering" 2000, Annu Rev Biomed Eng 2:339.
Morea et al., "Antibody Modeling: Implications for Engineering and Design" 2000, Methods 20:267.
Morea et al., "Antibody structure prediction and redesign" 1997, Biophys Chem 68:9.
Morrison, et al., "Chimeric human antibody molecules: Mouse antigen-binding domains with human constant region domains"1984, *Proc Natl Acad Sci USA* 81 :6851.
Nechansky et al., "Compensation of endogenous IgG mediated inhibition of antibody-dependent cellular cytotoxicity by glyco-engineering of therapeutic antibodies" 2007, Mol Immunjol 44(7):1826.
Pallares et al., "The Human Immunoglobulin Heavy Variable Genes"1999, *Exp Clin lmmunogenet* 16(1): 36-60.
Queen, et al., "A Humanized Antibody that Binds to the Interleukin 2 Receptor"1989, *Proc Natl Acad Sci U S A* 86:10029-10033.
Roguska, et al., "A comparison of two murine monoclonal antibodies humanized by CDR-grafting and variable domain resurfacing" 1996, *Protein Eng* 9:895-904.
Roguska, et al., "Humanization of Murine Monoclonal Antibodies Through Variable Domain Resurfacing" 1994, *Proc Natl Acad Sci U S A* 91:969-973.
Roque et al.," Antibodies and Genetically Engineered Related Molecules: Production and Purification" 2004, Biotechnol. Prog. 20:639.
Shields et al, "High Resolution Mapping of the Binding Site on Human IgG1 for FcgRl, FcgRII, FcgRIII, and FcRn and Design of IgG1 Variants with Improved Binding to the FcgR" Journal of Biological Chemistry, 2001, 276(9):6591-6604.
Shields et al., "Lack of Fucose on Human IgG1 N-Linked Oligosaccharide Improves Binding to Human Fc_RIII and Antibody-dependent Cellular Toxicity"2002, J Biol Chem 277:26733.
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity" 2003, J Biol Chem 278:3466.
Smith, et al., "Filamentous Fusion Phage: Novel Expressions Vectors That Display Cloned Antigens on the Virion Suface" 1985, *Science* 228:1315-1317.
Tan et al., ""Superhumanized" Antibodies: Reduction of Immunogenic Potential by Complementarity-Determining Region Grafting with Human Germline Sequences: Application to an Anti-CD28l"2002, J. Immunol. 169:1119.
Tsurushita, et al., "Humanization of Monoclonal Antibodies", Molecular Biology of B Cells, 2004, 533.
Uchiyama, et al., A Monoclonal Antibody (Anti-Tac) Reactive With Activated and Functionally Mature Human T Cells 1981, *J Immunol* 126:1393-1397.
Umaña et al., "Engineered glycoforms of an antineuro-blastoma IgG1 with optimized antibody-dependent cellular cytotoxic activity"1999, Nat Biotechnol 17:176.
Verhoeyen et al., "Reshaping Human Antibodies: Grafting an Antilysozyme Activity" 1988, Science 239:1534.
WHO Review of the notation for the allotypic and related markers of human immunoglobulins. 1976, Eur. J. Immunol. 6, 599-601.

WHO Review of the notation for the allotypic and related markers of human immunoglobulins. J Immunogen 1976, 3: 357.

Yamane-Ohnuki et al., " Establishment of FUTS Knockout Chinese Hamster Ovary Cells: An Ideal Host Cell Line for Producing Completely Defucosylated Antibodies with Enhanced Antibody-Dependent Cellular Cytotoxicity" 2004, Biotechnol Bioeng 87 (5), 614-622.

Zachau, et al, "The Immunoglobulin _Gene Families of Human and Mouse: a Cottage Industry Approach" 2000, Biol Chem 381:951-954.

* cited by examiner

Figure 3.

Sequences of CDR and interface positions of anti-CD25 variants

Figure 3 continued

Binding data and humanness scores of anti-CD25 variants

| Variant | $k_{on}$ ($10^6 M^{-1}s^{-1}$) | $k_{off}$ ($10^{-4}s^{-1}$) | $K_d$ (nM) | Fold change in $K_d$ vs. H1L1 | Human 9-mers | IDs |
|---|---|---|---|---|---|---|
| anti-CD25 H0L0 | 1.6 | 1.3 | 0.09 | | 12 | 155 |
| anti-CD25 H1L1 | 1.5 | 5.0 | 0.32 | | 103 | 187 |
| daclizumab | 1.6 | 2.3 | 0.15 | | 94 | 184 |
| IGHV1-2*02 / IGKV3-11*01 | | | | | | |
| _VH Single variants_ | | | | | | |
| anti-CD25 H1.1L1 | 1.9 | 3.1 | 0.16 | 2.0 | 102 | 188 |
| anti-CD25 H1.2L1 | 1.4 | 4.7 | 0.35 | -1.1 | 103 | 188 |
| anti-CD25 H1.3L1 | 2.0 | 2.6 | 0.13 | 2.4 | 101 | 188 |
| anti-CD25 H1.4L1 | 2.0 | 6.0 | 0.30 | 1.1 | 106 | 188 |
| anti-CD25 H1.5L1 | 1.9 | 3.5 | 0.19 | 1.7 | 105 | 188 |
| anti-CD25 H1.6L1 | 0.80 | 14.3 | 1.79 | -5.6 | 112 | 188 |
| anti-CD25 H1.7L1 | 1.9 | 5.8 | 0.30 | 1.1 | 103 | 188 |
| anti-CD25 H1.8L1 | 2.1 | 1.1 | 0.05 | 6.2 | 107 | 188 |
| anti-CD25 H1.9L1 | 2.2 | 2.7 | 0.12 | 2.6 | 103 | 188 |
| anti-CD25 H1.10L1 | 1.6 | 3.2 | 0.20 | 1.6 | 103 | 188 |
| anti-CD25 H1.11L1 | 1.5 | 4.7 | 0.32 | 1.0 | 103 | 188 |
| _VL Single variants_ | | | | | | |
| anti-CD25 H1L1.1 | 1.6 | 16.7 | 1.06 | -3.3 | 107 | 188 |
| anti-CD25 H1L1.2 | 1.8 | 4.6 | 0.25 | 1.3 | 103 | 188 |
| anti-CD25 H1L1.3 | 1.7 | 4.8 | 0.28 | 1.1 | 103 | 188 |
| anti-CD25 H1L1.4 | 1.8 | 5.8 | 0.33 | -1.0 | 103 | 188 |
| anti-CD25 H1L1.5 | 1.8 | 5.2 | 0.29 | 1.1 | 104 | 188 |
| anti-CD25 H1L1.6 | 1.8 | 5.7 | 0.32 | 1.0 | 98 | 188 |
| anti-CD25 H1L1.7 | 2.0 | 5.4 | 0.28 | 1.2 | 102 | 188 |
| anti-CD25 H1L1.8 | 1.9 | 6.0 | 0.32 | -1.0 | 105 | 188 |
| anti-CD25 H1L1.9 | 1.9 | 5.8 | 0.31 | 1.0 | 98 | 188 |
| anti-CD25 H1L1.10 | 1.9 | 5.2 | 0.28 | 1.1 | 103 | 188 |
| anti-CD25 H1L1.11 | 0.94 | 153.0 | 16.20 | -50.6 | 102 | 188 |
| anti-CD25 H1L1.12 | 1.7 | 92.7 | 5.42 | -16.9 | 103 | 188 |
| anti-CD25 H1L1.13 | 1.7 | 6.0 | 0.35 | -1.1 | 105 | 188 |
| anti-CD25 H1L1.14 | 1.8 | 4.8 | 0.27 | 1.2 | 103 | 188 |
| anti-CD25 H1L1.15 | 1.1 | 79.0 | 7.45 | -23.3 | 103 | 188 |
| anti-CD25 H1L1.16 | 1.6 | 4.2 | 0.26 | 1.2 | 103 | 188 |
| anti-CD25 H1L1.17 | 1.7 | 8.4 | 0.50 | -1.6 | 103 | 188 |
| anti-CD25 H1L1.18 | 1.5 | 13.2 | 0.90 | -2.8 | 103 | 188 |
| anti-CD25 H1L1.19 | 0.66 | 80.5 | 12.20 | -38.1 | 103 | 188 |

Figure 5.

Sequences of CDR and interface positions of anti-CD25 combination variants

| | Heavy chain | | | | | | | | | | | Light chain | | | | | | | | | | | | | | | | | | |
|---|---|---|---|---|---|---|---|---|---|---|---|---|---|---|---|---|---|---|---|---|---|---|---|---|---|---|---|---|---|---|
| | CDR1 | | CDR2 | | | | | | | | | | CDR1 | | | | | | | | CDR2 | | | | | | | CDR3 | | |
| Variant | 31 | 33 | 50 | 53 | 54 | 56 | 58 | 60 | 69 | 71 | 73 | 1 | 27 | 29 | 31 | 33 | 34 | 36 | 43 | 45 | 50 | 51 | 54 | 56 | 58 | 71 | 79 | 89 | 93 | 94 |
| anti-CD25 H0L0 | S | R | Y | S | T | Y | E | N | L | A | K | Q | S | I | - | R | H | F | S | K | T | T | L | S | V | Y | E | H | T | Y |
| anti-CD25 H1L1 | S | R | Y | S | T | Y | E | N | I | A | K | Q | S | I | - | M | H | F | S | Q | T | T | L | S | V | Y | Q | H | T | Y |
| daclizumab | S | R | Y | S | T | Y | E | N | I | A | E | D | S | I | - | M | H | Y | A | K | T | T | L | S | V | F | Q | H | T | Y |
| IGHV1-2*02 / IGKV3-11*01 | G | Y | W | N | S | G | N | A | M | R | T | E | Q | V | S | L | A | Y | A | R | D | A | R | T | I | F | E | Q | N | W |
| *VH Combination variants* | | | | | | | | | | | | | | | | | | | | | | | | | | | | | | |
| anti-CD25 H1.12L1 | G | R | W | N | S | G | N | A | M | R | T | Q | S | I | - | M | H | F | S | Q | T | T | L | S | V | Y | Q | H | T | Y |
| anti-CD25 H1.14L1 | G | R | Y | N | S | G | N | A | M | R | T | Q | S | I | - | M | H | F | S | Q | T | T | L | S | V | Y | Q | H | T | Y |
| anti-CD25 H1.22L1 | S | R | W | N | S | G | N | A | I | R | T | Q | S | I | - | M | H | F | S | Q | T | T | L | S | V | Y | Q | H | T | Y |
| anti-CD25 H1.23L1 | S | R | W | N | S | G | N | A | M | R | T | Q | S | I | - | M | H | F | S | Q | T | T | L | S | V | Y | Q | H | T | Y |
| *VL Combination variants* | | | | | | | | | | | | | | | | | | | | | | | | | | | | | | |
| anti-CD25 H1L1.20 | S | R | Y | S | T | Y | E | N | I | A | K | E | Q | V | - | L | H | Y | A | R | T | T | R | T | I | F | E | H | T | Y |
| anti-CD25 H1L1.43 | S | R | Y | S | T | Y | E | N | I | A | K | E | Q | V | - | L | H | Y | A | R | T | T | R | T | I | Y | Q | H | T | Y |
| anti-CD25 H1L1.48 | S | R | Y | S | T | Y | E | N | I | A | K | E | Q | V | - | M | H | Y | A | R | T | T | R | T | I | F | E | H | T | Y |
| anti-CD25 H1L1.56 | S | R | Y | S | T | Y | E | N | I | A | K | Q | Q | V | - | L | H | F | S | Q | T | T | R | T | I | F | E | H | T | Y |
| *VH/VL Combination variants* | | | | | | | | | | | | | | | | | | | | | | | | | | | | | | |
| anti-CD25 H1.12L1.20 | G | R | W | N | S | G | N | A | M | R | T | E | Q | V | - | L | H | Y | A | R | T | T | R | T | I | F | E | H | T | Y |
| anti-CD25 H1.12L1.43 | G | R | W | N | S | G | N | A | M | R | T | E | Q | V | - | L | H | Y | A | R | T | T | R | T | I | Y | Q | H | T | Y |
| anti-CD25 H1.12L1.48 | G | R | W | N | S | G | N | A | M | R | T | E | Q | V | - | M | H | Y | A | R | T | T | R | T | I | F | E | H | T | Y |
| anti-CD25 H1.12L1.56 | G | R | W | N | S | G | N | A | M | R | T | Q | Q | V | - | L | H | F | S | Q | T | T | R | T | I | F | E | H | T | Y |
| anti-CD25 H1.14L1.20 | G | R | Y | S | S | G | N | A | M | R | T | E | Q | V | - | L | H | Y | A | R | T | T | R | T | I | F | E | H | T | Y |
| anti-CD25 H1.14L1.43 | G | R | Y | N | S | G | N | A | M | R | T | E | Q | V | - | L | H | Y | A | R | T | T | R | T | I | Y | Q | H | T | Y |
| anti-CD25 H1.14L1.48 | G | R | Y | N | S | G | N | A | M | R | T | E | Q | V | - | M | H | Y | A | R | T | T | R | T | I | F | E | H | T | Y |
| anti-CD25 H1.14L1.56 | G | R | Y | N | S | G | N | A | M | R | T | Q | Q | V | - | L | H | F | S | Q | T | T | R | T | I | F | E | H | T | Y |
| anti-CD25 H1.22L1.20 | S | R | W | N | S | G | N | A | I | R | T | E | Q | V | - | L | H | Y | A | R | T | T | R | T | I | F | E | H | T | Y |
| anti-CD25 H1.22L1.43 | S | R | W | N | S | G | N | A | I | R | T | E | Q | V | - | L | H | Y | A | R | T | T | R | T | I | Y | Q | H | T | Y |
| anti-CD25 H1.22L1.48 | S | R | W | N | S | G | N | A | I | R | T | E | Q | V | - | M | H | Y | A | R | T | T | R | T | I | F | E | H | T | Y |
| anti-CD25 H1.22L1.56 | S | R | W | N | S | G | N | A | I | R | T | Q | Q | V | - | L | H | F | S | Q | T | T | R | T | I | F | E | H | T | Y |
| anti-CD25 H1.23L1.20 | S | R | W | N | S | G | N | A | M | R | T | E | Q | V | - | L | H | Y | A | R | T | T | R | T | I | F | E | H | T | Y |
| anti-CD25 H1.23L1.43 | S | R | W | N | S | G | N | A | M | R | T | E | Q | V | - | L | H | Y | A | R | T | T | R | T | I | Y | Q | H | T | Y |
| anti-CD25 H1.23L1.48 | S | R | W | N | S | G | N | A | M | R | T | E | Q | V | - | M | H | Y | A | R | T | T | R | T | I | F | E | H | T | Y |
| anti-CD25 H1.23L1.56 | S | R | W | N | S | G | N | A | M | R | T | Q | Q | V | - | L | H | F | S | Q | T | T | R | T | I | F | E | H | T | Y |

Figure 5 continued

Binding data and humanness scores of anti-CD25 combination variants

| Variant | $k_{on}$ ($10^6 M^{-1}s^{-1}$) | $k_{off}$ ($10^{-4}s^{-1}$) | $K_d$ (nM) | Fold change in $K_d$ vs. H0L0 | Human 9-mers | IDs |
|---|---|---|---|---|---|---|
| anti-CD25 H0L0 | 0.67 | 1.8 | 0.26 | | 12 | 155 |
| anti-CD25 H1L1 | 0.65 | 5.8 | 0.88 | -3.4 | 103 | 187 |
| daclizumab | 0.57 | 2.4 | 0.41 | | 94 | 184 |
| IGHV1-2*02 / IGKV3-11*01 | | | | | | |
| _VH Combination variants_ | | | | | | |
| anti-CD25 H1.12L1 | 1.1 | 1.2 | 0.11 | 2.3 | 131 | 197 |
| anti-CD25 H1.14L1 | 0.77 | 2.8 | 0.36 | -1.4 | 122 | 196 |
| anti-CD25 H1.22L1 | 0.98 | 1.7 | 0.18 | 1.5 | 128 | 195 |
| anti-CD25 H1.23L1 | 0.95 | 1.9 | 0.20 | 1.3 | 131 | 196 |
| _VL Combination variants_ | | | | | | |
| anti-CD25 H1L1.20 | 0.43 | 4.8 | 1.10 | -4.2 | 117 | 199 |
| anti-CD25 H1L1.43 | 0.41 | 5.3 | 1.30 | -5.0 | 117 | 197 |
| anti-CD25 H1L1.48 | 0.50 | 3.1 | 0.63 | -2.4 | 117 | 198 |
| anti-CD25 H1L1.56 | 0.54 | 7.0 | 1.30 | -5.0 | 114 | 195 |
| _VH/VL Combination variants_ | | | | | | |
| anti-CD25 H1.12L1.20 | 0.75 | 1.3 | 0.17 | 1.5 | 145 | 209 |
| anti-CD25 H1.12L1.43 | 0.72 | 1.4 | 0.19 | 1.4 | 145 | 207 |
| anti-CD25 H1.12L1.48 | 0.80 | 1.2 | 0.15 | 1.7 | 145 | 208 |
| anti-CD25 H1.12L1.56 | 0.85 | 1.8 | 0.21 | 1.2 | 142 | 205 |
| anti-CD25 H1.14L1.20 | 0.58 | 2.9 | 0.49 | -1.9 | 136 | 208 |
| anti-CD25 H1.14L1.43 | 0.67 | 2.2 | 0.32 | -1.3 | 136 | 206 |
| anti-CD25 H1.14L1.48 | 0.79 | 1.7 | 0.21 | 1.2 | 136 | 207 |
| anti-CD25 H1.14L1.56 | 1.0 | 1.7 | 0.16 | 1.6 | 133 | 204 |
| anti-CD25 H1.22L1.20 | 0.72 | 1.8 | 0.24 | 1.1 | 142 | 207 |
| anti-CD25 H1.22L1.43 | 0.64 | 1.9 | 0.30 | -1.1 | 142 | 205 |
| anti-CD25 H1.22L1.48 | 0.78 | 1.4 | 0.17 | 1.5 | 142 | 206 |
| anti-CD25 H1.22L1.56 | 0.97 | 2.2 | 0.22 | 1.2 | 139 | 203 |
| anti-CD25 H1.23L1.20 | 0.71 | 1.6 | 0.22 | 1.2 | 145 | 208 |
| anti-CD25 H1.23L1.43 | 0.73 | 1.2 | 0.16 | 1.6 | 145 | 206 |
| anti-CD25 H1.23L1.48 | 0.75 | 1.8 | 0.23 | 1.1 | 145 | 207 |
| anti-CD25 H1.23L1.56 | 0.95 | 2.0 | 0.21 | 1.2 | 142 | 204 |

Figure 6.
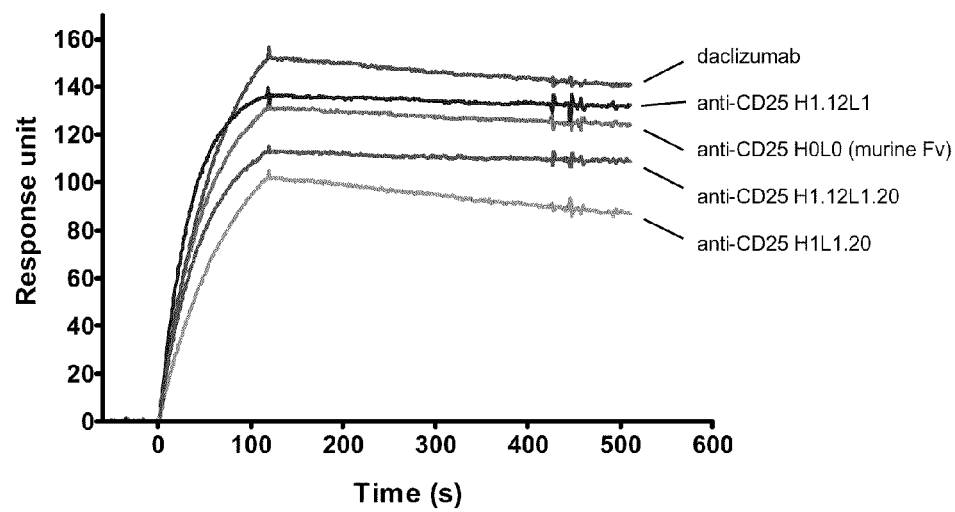
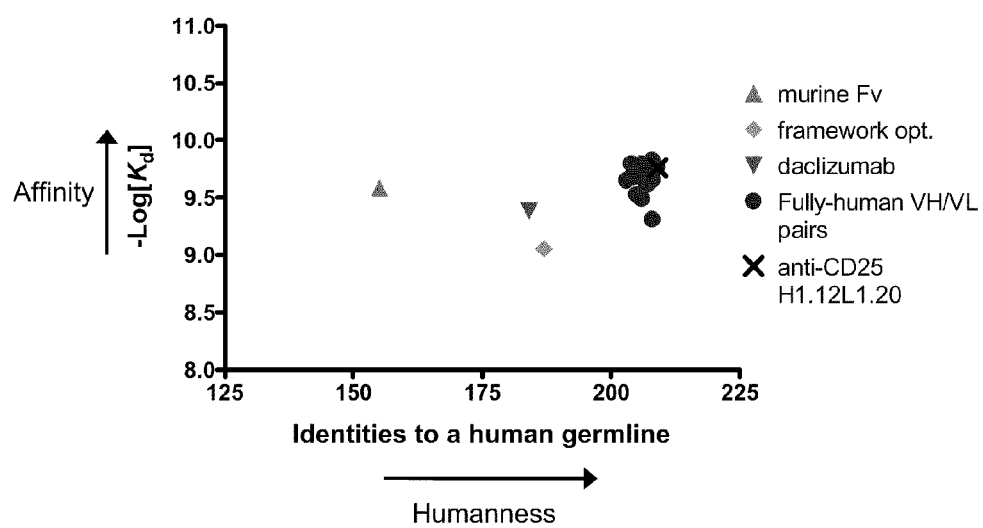

Figure 10.
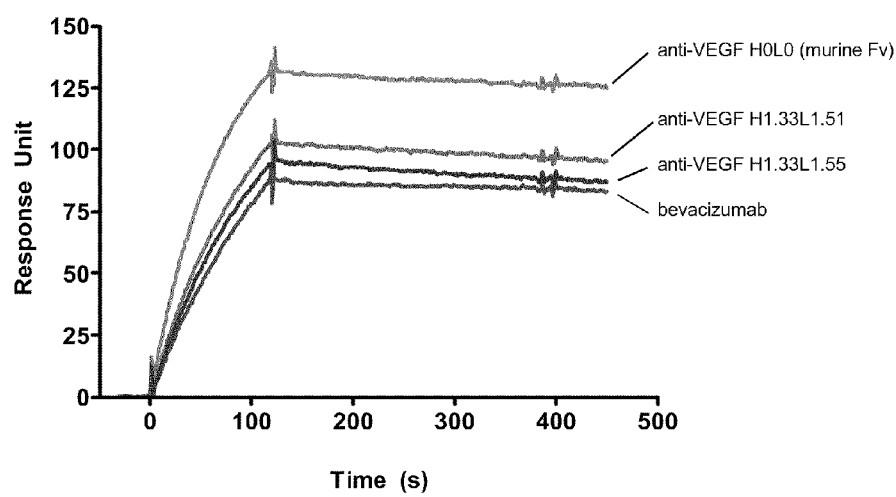
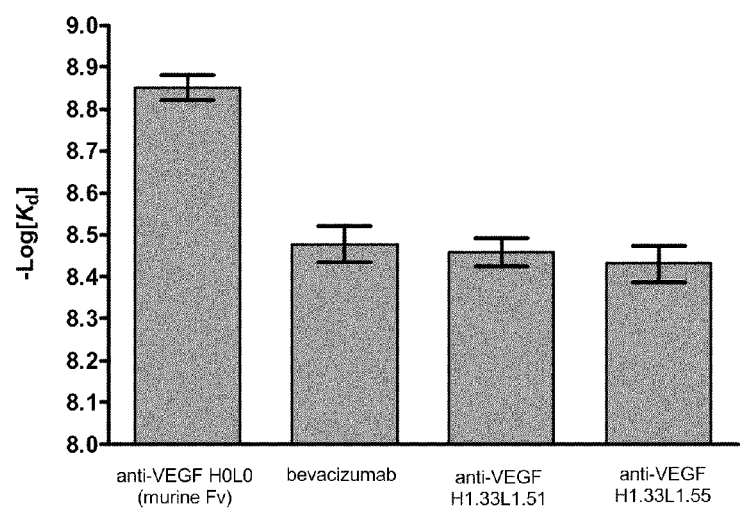

Figure 11.

Sequences of CDR and interface positions, binding data, and humanness scores of anti-VEGF variant Fabs

| Variant | Heavy chain | | | | | | | | | | Light chain | | | | | | | | | | | | | | | $k_{on}$ $(10^4 M^{-1} s^{-1})$ | $k_{off}$ $(10^{-4} s^{-1})$ | $K_d$ (nM) | Fold change in $K_d$ vs. HOL0 | Human 9-mers (%) | ID (%) |
|---|---|---|---|---|---|---|---|---|---|---|---|---|---|---|---|---|---|---|---|---|---|---|---|---|---|---|---|---|---|---|---|
| | FR1 | CDR1 | | | CDR2 | | | FR3 | | | FR2 | | | | CDR2 | | | | | | FR3 | | | CDR3 | | | | | | | | |
| | 2 | 31 | 33 | 53 | 56 | 61 | 91 | | | | 43 | 44 | 46 | 50 | 51 | 53 | 55 | 56 | 71 | 73 | 83 | 92 | 93 | 94 | | | | | | | |
| anti-VEGF H0L0 | I | N | G | Y | E | A | F | | | | T | V | V | F | T | S | H | S | Y | L | I | S | T | V | 13.4±0.6 | 1.7±0.2 | 1.4±0.2 | | 25 | 164 |
| anti-VEGF H1L1 | I | N | G | Y | E | A | F | | | | T | V | V | F | T | S | H | S | Y | L | F | S | T | V | | | | | 118 | 195 |
| bevacizumab | V | N | G | Y | E | A | Y | | | | A | P | V | F | T | S | H | S | F | L | F | S | T | V | 6.4±0.3 | 2.1±0.3 | 3.4±0.7 | -2.4 | 103 | 184 |
| IGHV7-4-1*02 / IGKV1-33*01 | V | S | A | N | N | Q | Y | | | | A | P | L | D | A | N | E | T | F | F | I | D | N | L | | | | | | |
| VH/VL combination variants | | | | | | | | | | | | | | | | | | | | | | | | | | | | | | |
| anti-VEGF H1.33L1.51 | V | N | G | Y | E | A | Y | | | | A | P | V | F | T | S | H | S | Y | L | F | D | N | L | 8.3±0.4 | 2.9±0.3 | 3.5±0.5 | -2.5 | 147 | 204 |
| anti-VEGF H1.33L1.55 | V | N | G | Y | E | A | Y | | | | A | P | V | F | A | N | E | T | Y | L | F | D | N | L | 8.0±0.6 | 2.8±0.4 | 3.8±0.7 | -2.7 | 152 | 208 |

Binding data and humanness scores from anti-VEGF single variants were used to design a library of combination variants that would maximize humanness scores and maintain antigen affinity. Binding to VEGF was measured with BIAcore, and shaded residues indicate differences between each variant and anti-VEGF H1L1. Percent human 9-mers and percent identity to the closest human germline V and J regions for each $V_H$ and $V_L$ pair is also shown.

Figure 12.

Sequence properties and final affinity results for engineered mAbs

| | | | VH | | | | | | | |
|---|---|---|---|---|---|---|---|---|---|---|
| | CDR1 | | CDR2 | | | CDR3 | | | Total VH mutations | Total percent VH CDR humanness |
| Engineered mAb | No. mutations | Percent changed | Final CDR humanness | No. mutations | Percent changed | Final CDR humanness | No. mutations | Percent changed | Final CDR humanness | | |
| anti-CD25 H1.12L1.20 | 1 | 20.0% | 80.0% | 8 | 47.1% | 100.0% | 0 | 0.0% | N/A | 9 | 95.5% |
| anti-VEGF H1.33L1.55 | 0 | 0.0% | 60.0% | 5 | 29.4% | 94.1% | 0 | 0.0% | N/A | 5 | 86.4% |
| anti-TNF H1.103L1.33 | 0 | 0.0% | 20.0% | 4 | 21.1% | 84.2% | 0 | 0.0% | N/A | 4 | 70.8% |

| | | | VL | | | | | | | |
|---|---|---|---|---|---|---|---|---|---|---|
| | CDR1 | | CDR2 | | | CDR3 | | | Total VH mutations | Total percent VL CDR humanness |
| Engineered mAb | No. mutations | Percent changed | Final CDR humanness | No. mutations | Percent changed | Final CDR humanness | No. mutations | Percent changed | Final CDR humanness | | |
| anti-CD25 H1.12L1.20 | 4 | 40.0% | 81.8% | 2 | 28.6% | 83.3% | 0 | 0.0% | 55.6% | 6 | 70.4% |
| anti-VEGF H1.33L1.55 | 1 | 10.0% | 100.0% | 4 | 57.1% | 85.7% | 3 | 33.3% | 100.0% | 8 | 96.3% |
| anti-TNF H1.103L1.33 | 2 | 18.2% | 90.0% | 1 | 14.3% | 85.7% | 0 | 0.0% | 55.6% | 3 | 76.9% |

| Engineered mAb | Total CDR mutations | Total percent CDR humanness | Fold affinity change relative to H0L0 |
|---|---|---|---|
| anti-CD25 H1.12L1.20 | 15 | 81.6% | + 1.5 fold |
| anti-VEGF H1.33L1.55 | 13 | 91.8% | - 2.7 fold |
| anti-TNF H1.103L1.33 | 7 | 74.0% | - 1.3 fold |

Figure 14.

| Antibody | Antigen | Type of Fv | Status |
|---|---|---|---|
| rituximab | CD20 | murine | approved |
| cetuximab | EGFR | murine | approved |
| infliximab | TNFα | murine | approved |
| abciximab | GP IIa/IIIb receptor | murine | approved |
| basiliximab | CD25 | murine | approved |
| ibritumomab | CD20 | murine | approved |
| tositumomab | CD20 | murine | approved |
| muromonab | CD3 | murine | approved |
| satumomab | TAG72 | murine | approved |
| arcitumomab | CEA | murine | approved |
| alemtuzumab | CD52 | humanized | approved |
| bevacizumab | VEGF | humanized | approved |
| certolizumab | TNFα | humanized | approved |
| daclizumab | CD25 | humanized | approved |
| eculizumab | C5 | humanized | approved |
| efalizumab | CD11a | humanized | approved |
| gemtuzumab | CD33 | humanized | approved |
| motavizumab | RSV | humanized[a] | approved |
| natalizumab | α4β7 integrin | humanized | approved |
| omalizumab | IgE | humanized | approved |
| palivizumab | RSV | humanized | approved |
| ranibizumab | VEGF | humanized[b] | approved |
| tocilizumab | IL-6R | humanized | approved |
| trastuzumab | HER2/neu | humanized | approved |
| adalimumab | TNFa | fully-human[c] | approved |
| panitumumab | EGFR | fully-human[d] | approved |
| denosumab | RANKL | fully-human[d] | clinical trials |
| gantenerumab | Abeta peptide | fully-human[c] | clinical trials |
| golimumab | TNFα | fully-human[d] | clinical trials |
| ipilimumab | CTLA-4 | fully-human[d] | clinical trials |
| lucatumumab | CD40 | fully-human[d] | clinical trials |
| anti-CD25 H1.12_L1.20 | CD25 | XmAb fully-human | pre-clinical |
| anti-VEGF H1.33_L1.55 | VEGF | XmAb fully-human | pre-clinical |
| anti-TNF H1.103_L1.33 | TNFa | XmAb fully-human | pre-clinical |

*V-segment and J-segment germlines are listed
a: motavizumab is an affinity enhanced version of palivizumab
b: ranibizumab is an affinity enhanced version of bevacizumab
c: phage display technology using human mAb libraries
d: transgenic mouse technology

Figure 14 continued

| Antibody | IDs to closest human germline Fv | Fv length | % ID to closest human germline Fv | Human 9-mers | Human 9-mers (%) | Closest germline (VH)* | Closest germline (VL)* |
|---|---|---|---|---|---|---|---|
| rituximab | 152 | 227 | 67.0% | 9 | 4.3% | 1-3 / IGHJ2 | 1-9 / IGKJ2 |
| cetuximab | 141 | 226 | 62.4% | 11 | 5.2% | 2-26 / IGHJ4 | 6-21 / IGKJ2 |
| infliximab | 155 | 227 | 68.3% | 18 | 8.5% | 3-73 / IGHJ4 | 6-21 / IGKJ2 |
| abciximab | 151 | 226 | 66.8% | 5 | 2.4% | 1-3 / IGHJ6 | 1-8 / IGKJ2 |
| basiliximab | 146 | 221 | 66.1% | 12 | 5.9% | 1-3 / IGHJ6 | 3-11 / IGKJ2 |
| ibritumomab | 152 | 227 | 67.0% | 9 | 4.3% | 1-3 / IGHJ2 | 1-9 / IGKJ2 |
| tositumomab | 152 | 228 | 66.7% | 11 | 5.2% | 1-3 / IGHJ2 | 3-11 / IGKJ2 |
| muromonab | 151 | 225 | 67.1% | 7 | 3.3% | 1-46 / IGHJ6 | 3-11 / IGKJ2 |
| satumomab | 150 | 221 | 67.9% | 8 | 3.9% | 1-3 / IGHJ1 | 1-39 / IGKJ2 |
| arcitumomab | 159 | 227 | 70.0% | 26 | 12.3% | 3-72 / IGHJ4 | 3-11 / IGKJ2 |
| alemtuzumab | 180 | 228 | 78.9% | 72 | 34.0% | 4-30-4 / IGHJ4 | 1-33 / IGKJ1 |
| bevacizumab | 184 | 230 | 80.0% | 103 | 48.1% | 3-23 / IGHJ2 | 1-16 / IGKJ1 |
| certolizumab | 181 | 225 | 80.4% | 93 | 44.5% | 3-23 / IGHJ6 | 1-16 / IGKJ1 |
| daclizumab | 184 | 222 | 82.9% | 94 | 45.6% | 1-46 / IGHJ6 | 1-5 / IGKJ1 |
| eculizumab | 185 | 229 | 80.8% | 100 | 46.9% | 1-46 / IGHJ2 | 1-39 / IGKJ1 |
| efalizumab | 185 | 228 | 81.1% | 106 | 50.0% | 3-7 / IGHJ4 | 1-9 / IGKJ1 |
| gemtuzumab | 184 | 227 | 81.1% | 100 | 47.4% | 1-3 / IGHJ4 | 1-39 / IGKJ1 |
| motavizumab | 187 | 226 | 82.7% | 89 | 42.4% | 2-5 / IGHJ6 | 1-5 / IGKJ4 |
| natalizumab | 184 | 229 | 80.3% | 85 | 39.9% | 1-3 / IGHJ6 | 1-33 / IGKJ1 |
| omalizumab | 188 | 232 | 81.0% | 112 | 51.9% | 3-66 / IGHJ1 | 1-39 / IGKJ1 |
| palivizumab | 186 | 226 | 82.3% | 89 | 42.4% | 2-5 / IGHJ2 | 1-5 / IGKJ2 |
| ranibizumab | 182 | 230 | 79.1% | 103 | 48.1% | 3-23 / IGHJ2 | 1-16 / IGKJ1 |
| tocilizumab | 177 | 226 | 78.3% | 68 | 32.4% | 2-5 / IGHJ4 | 1-39 / IGKJ1 |
| trastuzumab | 186 | 227 | 81.9% | 96 | 45.5% | 3-66 / IGHJ4 | 1-39 / IGKJ1 |
| adalimumab | 207 | 228 | 90.8% | 152 | 71.7% | 3-9 / IGHJ4 | 1-27 / IGKJ1 |
| panitumumab | 205 | 226 | 90.7% | 119 | 56.7% | 4-61 / IGHJ3 | 1-33 / IGKJ4 |
| denosumab | 213 | 230 | 92.6% | 155 | 72.4% | 3-23 / IGHJ5 | 3-20 / IGKJ1 |
| gantenerumab | 202 | 233 | 86.7% | 152 | 70.0% | 3-23 / IGHJ4 | 3D-7 / IGKJ1 |
| golimumab | 218 | 233 | 93.6% | 150 | 69.1% | 3-30 / IGHJ6 | 3-11 / IGKJ3 |
| ipilimumab | 213 | 226 | 94.2% | 147 | 70.0% | 3-30 / IGHJ4 | 3-20 / IGKJ1 |
| lucatumumab | 210 | 232 | 90.5% | 132 | 61.1% | 3-30 / IGHJ4 | 2-29 / IGKJ3 |
| anti-CD25 H1.12_L1.20 | 209 | 222 | 94.1% | 145 | 70.4% | 1-2 / IGHJ4 | 3-11 / IGKJ2 |
| anti-VEGF H1.33_L1.55 | 208 | 230 | 90.4% | 152 | 71.0% | 7-4-1 / IGHJ2 | 1-33 / IGKJ1 |
| anti-TNF H1.103_L1.33 | 204 | 227 | 89.9% | 123 | 58.3% | 3-73 / IGHJ4 | 6-21 / IGKJ2 |

*V-segment and J-segment germlines are listed

Figure 15

Rituximab VH SEQ ID No. 265

QVQLQQPGAELVKPGASVKMSCKASGYTFTSYNMHWVKQTPGRGLEWIGAIYPGNG
DTSYNQKFKGKATLTADKSSSTAYMQLSSLTSEDSAVYYCARSTYYGGDWYFNVWG
AGTTVTVSA

Rituximab VL SEQ ID No. 166

QIVLSQSPAILSASPGEKVTMTCRASSSVSYIHWFQQKPGSSPKPWIYATSNLASGVPV
RFSGSGSGTSYSLTISRVEAEDAATYYCQQWTSNPPTFGGGTKLEIK

Cetuximab VH SEQ ID No. 167

QVQLKQSGPGLVQPSQSLSITCTVSGFSLTNYGVHWVRQSPGKGLEWLGVIWSGGN
TDYNTPFTSRLSINKDNSKSQVFFKMNSLQSNDTAIYYCARALTYYDYEFAYWGQGTL
VTVSA

Cetuximab VL SEQ ID No. 168

DILLTQSPVILSVSPGERVSFSCRASQSIGTNIHWYQQRTNGSPRLLIKYASESISGIPSR
FSGSGSGTDFTLSINSVESEDIADYYCQQNNNWPTTFGAGTKLELK

Infliximab VH SEQ ID No. 169

EVKLEESGGGLVQPGGSMKLSCVASGFIFSNHWMNWVRQSPEKGLEWVAEIRSKSIN
SATHYAESVKGRFTISRDDSKSAVYLQMTDLRTEDTGVYYCSRNYYGSTYDYWGQGT
TLTVSS

Infliximab VL SEQ ID No. 170

DILLTQSPAILSVSPGERVSFSCRASQFVGSSIHWYQQRTNGSPRLLIKYASESMSGIP
SRFSGSGSGTDFTLSINTVESEDIADYYCQQSHSWPFTFGSGTNLEVK

Abciximab VH SEQ ID No. 171

EVQLQQSGAELVKPGASVKLSCTASGFNIKDTYVHWVKQRPEQGLEWIGRIDPANGY
TKYDPKFQGKATITADTSSNTAYLQLSSLTSEDTAVYYCVRPLYDYYAMDYWGQGTSV
TVSS

Abciximab VL SEQ ID No. 172

DILMTQSPSSMSVSLGDTVSITCHASQGISSNIGWLQQKPGKSFMGLIYYGTNLVDGVP
SRFSGSGSGADYSLTISSLDSEDFADYYCVQYAQLPYTFGGGTKLEIK

Figure 15 (cont.)

Basiliximab VH SEQ ID No. 173

EVQLQQSGTVLARPGASVKMSCKASGYSFT<u>RYWMH</u>WIKQRPGQGLEWIG<u>AIYPGNS
DTSYNQKFEG</u>KAKLTAVTSASTAYMELSSLTHEDSAVYYCSR<u>DYGYYFDF</u>WGQGTTL
TVSS

Basiliximab VL SEQ ID No. 174

QIVSTQSPAIMSASPGEKVTMTC<u>SASSSRSYMQ</u>WYQQKPGTSPKRWIY<u>DTSKLAS</u>GV
PARFSGSGSGTSYSLTISSMEAEDAATYYC<u>HQRSSYT</u>FGGGTKLEIK

Ibritumomab VH SEQ ID No. 175

QVQLQQPGAELVKPGASVKMSCKASGYTFT<u>SYNMH</u>WVKQTPGRGLEWIG<u>AIYPGNG
DTSYNQKFKG</u>KATLTADKSSSTAYMQLSSLTSEDSAVYYCAR<u>STYYGGDWYFNV</u>WG
AGTTVTVSA

Ibritumomab VL SEQ ID No. 176

QIVLSQSPAILSASPGEKVTMTC<u>RASSSVSYIH</u>WFQQKPGSSPKPWIY<u>ATSNLAS</u>GVPV
RFSGSGSGTSYSLTISRVEAEDAATYYC<u>QQWTSNPPT</u>FGGGTKLEIK

Tositumomab VH SEQ ID No. 177

QAYLQQSGAELVRPGASVKMSCKASGYTFT<u>SYNMH</u>WVKQTPRQGLEWIG<u>AIYPGNG
DTSYNQKFKG</u>KATLTVDKSSSTAYMQLSSLTSEDSAVYFCAR<u>VVYYSNSYWYFDV</u>WG
TGTTVTVSG

Tositumomab VL SEQ ID No. 178

QIVLSQSPAILSASPGEKVTMTC<u>RASSSVSYMH</u>WYQQKPGSSPKPWIY<u>APSNLAS</u>GVP
ARFSGSGSGTSYSLTISRVEAEDAATYYC<u>QQWSFNPPT</u>FGAGTKLELK

Muromonab VH SEQ ID No. 179

QVQLQQSGAELARPGASVKMSCKASGYTFT<u>RYTMH</u>WVKQRPGQGLEWIG<u>YINPSRG
YTNYNQKFKD</u>KATLTTDKSSSTAYMQLSSLTSEDSAVYYCAR<u>YYDDHYCLDY</u>WGQGT
TLTVSS

Muromonab VL SEQ ID No. 180

QIVLTQSPAIMSASPGEKVTMTC<u>SASSSVSYMN</u>WYQQKSGTSPKRWIY<u>DTSKLAS</u>GV
PAHFRGSGSGTSYSLTISGMEAEDAATYYC<u>QQWSSNPFT</u>FGSGTKLEIN

Figure 15 (cont.)

Satumomab VH SEQ ID No. 181

QVQLQQSDAELVKPGASVKISCKASGYTFTDHAIHWAKQKPEQGLEWIGYISPGNDDI
KYNEKFKGKATLTADKSSSTAYMQLNSLTSEDSAVYFCKRSYYGHWGQGTTLTVSS

Satumomab VL SEQ ID No. 182

DIQMTQSPASLSVSVGETVTITCRASENIYSNLAWYQQKQGKSPQLLVYAATNLADGV
PSRFSGSGSGTQYSLKINSLQSEDFGSYYCQHFWGTPYTFGGGTRLEIK

Arcitumomab VH SEQ ID No. 183

EVKLVESGGGLVQPGGSLRLSCATSGFTFTDYYMNWVRQPPGKALEWLGFIGNKAN
GYTTEYSASVKGRFTISRDKSQSILYLQMNTLRAEDSATYYCTRDRGLRFYFDYWGQG
TTLTVSS

Arcitumomab VL SEQ ID No. 184

QTVLSQSPAILSASPGEKVTMTCRASSSVTYIHWYQQKPGSSPKSWIYATSNLASGVP
ARFSGSGSGTSYSLTISRVEAEDAATYYCQHWSSKPPTFGGGTKLEIK

Alemtuzumab VH SEQ ID No. 185

QVQLQESGPGLVRPSQTLSLTCTVSGFTFTDFYMNWVRQPPGRGLEWIGFIRDKAKG
YTTEYNPSVKGRVTMLVDTSKNQFSLRLSSVTAADTAVYYCAREGHTAAPFDYWGQG
SLVTVSS

Alemtuzumab VL SEQ ID No. 186

DIQMTQSPSSLSASVGDRVTITCKASQNIDKYLNWYQQKPGKAPKLLIYNTNNLQTGVP
SRFSGSGSGTDFTFTISSLQPEDIATYYCLQHISRPRTFGQGTKVEIK

Bevacizumab VH SEQ ID No. 187

EVQLVESGGGLVQPGGSLRLSCAASGYTFTNYGMNWVRQAPGKGLEWVGWINTYT
GEPTYAADFKRRFTFSLDTSKSTAYLQMNSLRAEDTAVYYCAKYPHYYGSSHWYFDV
WGQGTLVTVSS

Bevacizumab VL SEQ ID No. 188

DIQMTQSPSSLSASVGDRVTITCSASQDISNYLNWYQQKPGKAPKVLIYFTSSLHSGVP
SRFSGSGSGTDFTLTISSLQPEDFATYYCQQYSTVPWTFGQGTKVEIK

Figure 15 (cont.)

Certolizumab VH SEQ ID No. 189

EVQLVESGGGLVQPGGSLRLSCAASGYVFT<u>DYGMN</u>WVRQAPGKGLEWMG<u>WINTYIG
EPIYADSVKG</u>RFTFSLDTSKSTAYLQMNSLRAEDTAVYYCAR<u>GYRSYAMDY</u>WGQGTL
VTVSS

Certolizumab VL SEQ ID No. 190

DIQMTQSPSSLSASVGDRVTITC<u>KASQNVGTNVA</u>WYQQKPGKAPKALIY<u>SASFLYS</u>GV
PYRFSGSGSGTDFTLTISSLQPEDFATYYC<u>QQYNIYPLT</u>FGQGTKVEIK

Daclizumab VH SEQ ID No. 191

QVQLVQSGAEVKKPGSSVKVSCKASGYTFT<u>SYRMH</u>WVRQAPGQGLEWIG<u>YINPSTG
YTEYNQKFKD</u>KATITADESTNTAYMELSSLRSEDTAVYYCAR<u>GGGVFDY</u>WGQGTLVT
VSS

Daclizumab VL SEQ ID No. 192

DIQMTQSPSTLSASVGDRVTITC<u>SASSSISYMH</u>WYQQKPGKAPKLLIY<u>TTSNLAS</u>GVPA
RFSGSGSGTEFTLTISSLQPDDFATYYC<u>HQRSTYPLT</u>FGQGTKVEVK

Eculizumab VH SEQ ID No. 193

QVQLVQSGAEVKKPGASVKVSCKASGYIFS<u>NYWIQ</u>WVRQAPGQGLEWMG<u>EILPGSG
STEYTENFKD</u>RVTMTRDTSTSTVYMELSSLRSEDTAVYYCAR<u>YFFGSSPNWYFDV</u>WG
QGTLVTVSS

Eculizumab VL SEQ ID No. 194

DIQMTQSPSSLSASVGDRVTITC<u>GASENIYGALN</u>WYQRKPGKAPKLLIY<u>GATNLAD</u>GVP
SRFSGSGSGTDYTLTISSLQPEDFATYYC<u>QNVLNTPLT</u>FGQGTKVEIK

Efalizumab VH SEQ ID No. 195

EVQLVESGGGLVQPGGSLRLSCAASGYSFT<u>GHWMN</u>WVRQAPGKGLEWVGM<u>IHPSD
SETRYNQKFKD</u>RFTISVDKSKNTLYLQMNSLRAEDTAVYYCAR<u>GIYFYGTTYFDY</u>WGQ
GTLVTVSS

Efalizumab VL SEQ ID No. 196

DIQMTQSPSSLSASVGDRVTITC<u>RASKTISKYLA</u>WYQQKPGKAPKLLIY<u>SGSTLQS</u>GVP
SRFSGSGSGTDFTLTISSLQPEDFAFYYC<u>QQHNEYPLT</u>FGQGTKVEIK

Figure 15 (cont.)

Gemtuzumab VH SEQ ID No. 197

QVQLVQSGAEVKKPGSSVKVSCKASGYTFT<u>DYNMH</u>WVRQAPGQGLEWIG<u>YIYPYNG
GTGYNQKFKS</u>KATITADESTNTAYMELSSLRSEDTAVYYCAR<u>GRPAMDY</u>WGQGTLVT
VSS

Gemtuzumab VL SEQ ID No. 198

DIQMTQSPSSLSASVGDRVTITC<u>RASESVDNYGISFMN</u>WFQQKPGGAPKLLIY<u>AASNQ
GS</u>GVPSRFSGSGSGTDFTLTISSLQPDDFATYYC<u>QQSKEVPWT</u>FGQGTKVEIK

Motavizumab VH SEQ ID No. 199

QVTLRESGPALVKPTQTLTLTCTFSGFSL<u>STAGMSVG</u>WIRQPPGKALEWLA<u>DIWWDD
KKHYNPSLKD</u>RLTISKDTSKNQVVLKVTNMDPADTATYYCAR<u>DMIFNFYFDV</u>WGQGTT
VTVSS

Motavizumab VL SEQ ID No. 200

DIQMTQSPSTLSASVGDRVTITC<u>SASSRVGYMH</u>WYQQKPGKAPKLLIY<u>DTSKLAS</u>GVP
SRFSGSGSGTEFTLTISSLQPDDFATYYC<u>FQGSGYPFT</u>FGGGTKVEIK

Natalizumab VH SEQ ID No. 201

QVQLVQSGAEVKKPGASVKVSCKASGFNIK<u>DTYIH</u>WVRQAPGQRLEWMG<u>RIDPANGY
TKYDPKFQG</u>RVTITADTSASTAYMELSSLRSEDTAVYYCAR<u>EGYYGNYGVYAMDY</u>WG
QGTLVTVSS

Natalizumab VL SEQ ID No. 202

DIQMTQSPSSLSASVGDRVTITC<u>KTSQDINKYMA</u>WYQQTPGKAPRLLIH<u>YTSALQP</u>GIP
SRFSGSGSGRDYTFTISSLQPEDIATYYC<u>LQYDNLWT</u>FGQGTKVEIK

Omalizumab VH SEQ ID No. 203

EVQLVESGGGLVQPGGSLRLSCAVSGYSIT<u>SGYSWN</u>WIRQAPGKGLEWVA<u>SITYDGS
TNYADSVKG</u>RFTISRDDSKNTFYLQMNSLRAEDTAVYYCAR<u>GSHYFGHWHFAV</u>WGQ
GTLVTVSS

Omalizumab VL SEQ ID No. 204

DIQLTQSPSSLSASVGDRVTITC<u>RASQSVDYDGDSYMN</u>WYQQKPGKAPKLLIY<u>AASYL
ES</u>GVPSRFSGSGSGTDFTLTISSLQPEDFATYYC<u>QQSHEDPYT</u>FGQGTKVEIK

Figure 15 (cont.)

Palivizumab VH SEQ ID No. 205

QVTLRESGPALVKPTQTLTLTCTFSGFSLSTSGMSVGWIRQPPGKALEWLADIWWDD
KKDYNPSLKSRLTISKDTSKNQVVLKVTNMDPADTATYYCARSMITNWYFDVWGAGTT
VTVSS

Palivizumab VL SEQ ID No. 206

DIQMTQSPSTLSASVGDRVTITCKCQLSVGYMHWYQQKPGKAPKLLIYDTSKLASGVP
SRFSGSGSGTEFTLTISSLQPDDFATYYCFQGSGYPFTFGGGTKLEIK

Ranibizumab VH SEQ ID No. 207

EVQLVESGGGLVQPGGSLRLSCAASGYDFTHYGMNWVRQAPGKGLEWVGWINTYT
GEPTYAADFKRRFTFSLDTSKSTAYLQMNSLRAEDTAVYYCAKYPYYYGTSHWYFDV
WGQGTLVTVSS

Ranibizumab VL SEQ ID No. 208

DIQLTQSPSSLSASVGDRVTITCSASQDISNYLNWYQQKPGKAPKVLIYFTSSLHSGVP
SRFSGSGSGTDFTLTISSLQPEDFATYYCQQYSTVPWTFGQGTKVEIK

Tocilizumab VH SEQ ID No. 209

QVTLRESGPALVRPTQTLTLTCTFSGFSLSTSGMTVGWIRQPPGEALEWLAHIWWND
DKYYNPALGKRLAVSKDTSKNQVVLSMNTVGPGDTATYYCARMEDYDEAMDYWGQ
GILVTVSS

Tocilizumab VL SEQ ID No. 210

DIQMTQSPSSLSASVGDRVTITCRASENIYSNLAWYQQKPGKAPKLLIYAATYLADGVP
SRFSGSGSGTDYTFTISSLQPEDIATYYCQRFWGTPPFGQGTKVEIK

Trastuzumab VH SEQ ID No. 211

EVQLVESGGGLVQPGGSLRLSCAASGFNIKDTYIHWVRQAPGKGLEWVARIYPTNGY
TRYADSVKGRFTISADTSKNTAYLQMNSLRAEDTAVYYCSRWGGDGFYAMDYWGQG
TLVTVSS

Trastuzumab VL SEQ ID No. 212

DIQMTQSPSSLSASVGDRVTITCRASQDVNTAVAWYQQKPGKAPKLLIYSASFLYSGV
PSRFSGSRSGTDFTLTISSLQPEDFATYYCQQHYTTPPTFGQGTKVEIK

Figure 16

Heavy chains:

>murine anti-CD25 VH (H0) (SEQ ID NO:1)
QVQLQQSGAELAKPGASVKMSCKASGYTFTSYRMHWVKQRPGQGLEWIGYINPS
TGYTEYNQKFKDKATLTADKSSSTAYMQLSSLTFEDSAVYYCARGGGVFDYWGQG
TTLTVSS >framework-optimized anti-CD25 (H1) (SEQ ID NO:2)
QVQLVQSGAEVKKPGASVKVSCKASGYTFTSYRMHWVRQAPGQGLEWMGYINPS
TGYTEYNQKFQGRVTITADKSISTAYMELSRLRSDDTAVYYCARGGGVFDYWGQG
TLVTVSS >anti-CD25 H1.1 variable region (SEQ ID NO:3)
QVQLVQSGAEVKKPGASVKVSCKASGYTFTSYRMHWVRQAPGQGLEWMGYINPS
TGYTEYNQKFQGRVTITRDKSISTAYMELSRLRSDDTAVYYCARGGGVFDYWGQG
TLVTVSS >anti-CD25 H1.2 variable region (SEQ ID NO:4)
QVQLVQSGAEVKKPGASVKVSCKASGYTFTSYRMHWVRQAPGQGLEWMGYINPS
TGYTNYNQKFQGRVTITADKSISTAYMELSRLRSDDTAVYYCARGGGVFDYWGQG
TLVTVSS >anti-CD25 H1.3 variable region (SEQ ID NO:5)
QVQLVQSGAEVKKPGASVKVSCKASGYTFTSYRMHWVRQAPGQGLEWMGYINPS
TGYTEYNQKFQGRVTMTADKSISTAYMELSRLRSDDTAVYYCARGGGVFDYWGQ
GTLVTVSS >anti-CD25 H1.4 variable region (SEQ ID NO:6)
QVQLVQSGAEVKKPGASVKVSCKASGYTFTSYRMHWVRQAPGQGLEWMGYINPS
TGYTEYNQKFQGRVTITADTSISTAYMELSRLRSDDTAVYYCARGGGVFDYWGQG
TLVTVSS >anti-CD25 H1.5 variable region (SEQ ID NO:7)
QVQLVQSGAEVKKPGASVKVSCKASGYTFTSYRMHWVRQAPGQGLEWMGYINPS
TGYTEYAQKFQGRVTITADKSISTAYMELSRLRSDDTAVYYCARGGGVFDYWGQG
TLVTVSS >anti-CD25 H1.6 variable region (SEQ ID NO:8)
QVQLVQSGAEVKKPGASVKVSCKASGYTFTSYYMHWVRQAPGQGLEWMGYINPS
TGYTEYNQKFQGRVTITADKSISTAYMELSRLRSDDTAVYYCARGGGVFDYWGQG
TLVTVSS >anti-CD25 H1.7 variable region (SEQ ID NO:9)
QVQLVQSGAEVKKPGASVKVSCKAGGYTFTSYRMHWVRQAPGQGLEWMGYINPS
TGYTEYNQKFQGRVTITADKSISTAYMELSRLRSDDTAVYYCARGGGVFDYWGQG
TLVTVSS >anti-CD25 H1.8 variable region (SEQ ID NO:10)
QVQLVQSGAEVKKPGASVKVSCKASGYTFTSYRMHWVRQAPGQGLEWMGWINP
STGYTEYNQKFQGRVTITADKSISTAYMELSRLRSDDTAVYYCARGGGVFDYWGQ
GTLVTVSS

Figure 16 (cont.)

>anti-CD25 H1.9 variable region (SEQ ID NO:11)
QVQLVQSGAEVKKPGASVKVSCKASGYTFTSYRMHWVRQAPGQGLEWMGYINPS
TGYTEYNQKFQGRVTITADKSISTAYMELSRLRSDDTAVYYCARGGGVFDYWGQG
TLVTVSS >anti-CD25 H1.10 variable region (SEQ ID NO:12)
QVQLVQSGAEVKKPGASVKVSCKASGYTFTSYRMHWVRQAPGQGLEWMGYINPN
TGYTEYNQKFQGRVTITADKSISTAYMELSRLRSDDTAVYYCARGGGVFDYWGQG
TLVTVSS >anti-CD25 H1.11 variable region (SEQ ID NO:13)
QVQLVQSGAEVKKPGASVKVSCKASGYTFTSYRMHWVRQAPGQGLEWMGYINPS
SGYTEYNQKFQGRVTITADKSISTAYMELSRLRSDDTAVYYCARGGGVFDYWGQG
TLVTVSS >anti-CD25 H1.12 variable region (SEQ ID NO:14)
QVQLVQSGAEVKKPGASVKVSCKASGYTFTGYRMHWVRQAPGQGLEWMGWINP
NSGGTNYAQKFQGRVTMTRDTSISTAYMELSRLRSDDTAVYYCARGGGVFDYWG
QGTLVTVSS >anti-CD25 H1.14 variable region (SEQ ID NO:15)
QVQLVQSGAEVKKPGASVKVSCKASGYTFTGYRMHWVRQAPGQGLEWMGYINP
NSGGTNYAQKFQGRVTMTRDTSISTAYMELSRLRSDDTAVYYCARGGGVFDYWG
QGTLVTVSS >anti-CD25 H1.22 variable region (SEQ ID NO:16)
QVQLVQSGAEVKKPGASVKVSCKASGYTFTSYRMHWVRQAPGQGLEWMGWINP
NSGGTNYAQKFQGRVTITRDTSISTAYMELSRLRSDDTAVYYCARGGGVFDYWGQ
GTLVTVSS >anti-CD25 H1.23 variable region (SEQ ID NO:17)
QVQLVQSGAEVKKPGASVKVSCKASGYTFTSYRMHWVRQAPGQGLEWMGWINP
NSGGTNYAQKFQGRVTMTRDTSISTAYMELSRLRSDDTAVYYCARGGGVFDYWG
QGTLVTVSS >murine anti-VEGF VH (H0) (SEQ ID NO:18)
EIQLVQSGPELKQPGETVRISCKASGYTFTNYGMNWVKQAPGKGLKWMGWINTYT
GEPTYAADFKRRFTFSLETSASTAYLQISNLKNDDTATYFCAKYPHYYGSSHWYFD
VWGAGTTVTVSS >framework-optimized anti-VEGF (H1) (SEQ ID NO:19)
QIQLVQSGSELKKPGASVKVSCKASGYTFTNYGMNWVRQAPGQGLEWMGWINTY
TGEPTYAAGFTGRFVFSLDTSVSTAYLQISSLKAEDTAVYFCAKYPHYYGSSHWYF
DVWGAGTLVTVSS >anti-VEGF H1.1 variable region (SEQ ID NO:20)
QVQLVQSGSELKKPGASVKVSCKASGYTFTNYGMNWVRQAPGQGLEWMGWINT
YTGEPTYAAGFTGRFVFSLDTSVSTAYLQISSLKAEDTAVYFCAKYPHYYGSSHWY
FDVWGAGTLVTVSS

Figure 16 (cont.)

>anti-VEGF H1.2 variable region (SEQ ID NO:21)
QIQLVQSGSELKKPGASVKVSCKASGYTFTSYGMNWVRQAPGQGLEWMGWINTY
TGEPTYAAGFTGRFVFSLDTSVSTAYLQISSLKAEDTAVYFCAKYPHYYGSSHWYF
DVWGAGTLVTVSS >anti-VEGF H1.3 variable region (SEQ ID NO:22)
QIQLVQSGSELKKPGASVKVSCKASGYTFTNYAMNWVRQAPGQGLEWMGWINTY
TGEPTYAAGFTGRFVFSLDTSVSTAYLQISSLKAEDTAVYFCAKYPHYYGSSHWYF
DVWGAGTLVTVSS >anti-VEGF H1.4 variable region (SEQ ID NO:23)
QIQLVQSGSELKKPGASVKVSCKASGYTFTNYGMNWVRQAPGQGLEWMGWINTN
TGEPTYAAGFTGRFVFSLDTSVSTAYLQISSLKAEDTAVYFCAKYPHYYGSSHWYF
DVWGAGTLVTVSS >anti-VEGF H1.5 variable region (SEQ ID NO:24)
QIQLVQSGSELKKPGASVKVSCKASGYTFTNYGMNWVRQAPGQGLEWMGWINTY
TGNPTYAAGFTGRFVFSLDTSVSTAYLQISSLKAEDTAVYFCAKYPHYYGSSHWYF
DVWGAGTLVTVSS >anti-VEGF H1.6 variable region (SEQ ID NO:25)
QIQLVQSGSELKKPGASVKVSCKASGYTFTNYGMNWVRQAPGQGLEWMGWINTY
TGEPTYAQGFTGRFVFSLDTSVSTAYLQISSLKAEDTAVYFCAKYPHYYGSSHWYF
DVWGAGTLVTVSS >anti-VEGF H1.7 variable region (SEQ ID NO:26)
QIQLVQSGSELKKPGASVKVSCKASGYTFTNYGMNWVRQAPGQGLEWMGWINTY
TGEPTYAAGFTGRFVFSLDTSVSTAYLQISSLKAEDTAVYYCAKYPHYYGSSHWYF
DVWGAGTLVTVSS >anti-VEGF H1.8 variable region (SEQ ID NO:27)
QIQLVQSGSELKKPGASVKVSCKASGYTFTGYGMNWVRQAPGQGLEWMGWINTY
TGEPTYAAGFTGRFVFSLDTSVSTAYLQISSLKAEDTAVYFCAKYPHYYGSSHWYF
DVWGAGTLVTVSS >anti-VEGF H1.9 variable region (SEQ ID NO:28)
QIQLVQSGSELKKPGASVKVSCKASGYTFTNYSMNWVRQAPGQGLEWMGWINTY
TGEPTYAAGFTGRFVFSLDTSVSTAYLQISSLKAEDTAVYFCAKYPHYYGSSHWYF
DVWGAGTLVTVSS >anti-VEGF H1.10 variable region (SEQ ID NO:29)
QIQLVQSGSELKKPGASVKVSCKASGYTFTTYGMNWVRQAPGQGLEWMGWINTY
TGEPTYAAGFTGRFVFSLDTSVSTAYLQISSLKAEDTAVYFCAKYPHYYGSSHWYF
DVWGAGTLVTVSS >anti-VEGF H1.11 variable region (SEQ ID NO:30)
QIQLVQSGSELKKPGASVKVSCKASGYTFTYYGMNWVRQAPGQGLEWMGWINTY
TGEPTYAAGFTGRFVFSLDTSVSTAYLQISSLKAEDTAVYFCAKYPHYYGSSHWYF
DVWGAGTLVTVSS

Figure 16 (cont.)

>anti-VEGF H1.12 variable region (SEQ ID NO:31)
QIQLVQSGSELKKPGASVKVSCKASGYTFTDYGMNWVRQAPGQGLEWMGWINTY
TGEPTYAAGFTGRFVFSLDTSVSTAYLQISSLKAEDTAVYFCAKYPHYYGSSHWYF
DVWGAGTLVTVSS >anti-VEGF H1.13 variable region (SEQ ID NO:32)
QIQLVQSGSELKKPGASVKVSCKASGYTFTNYDMNWVRQAPGQGLEWMGWINTY
TGEPTYAAGFTGRFVFSLDTSVSTAYLQISSLKAEDTAVYFCAKYPHYYGSSHWYF
DVWGAGTLVTVSS >anti-VEGF H1.32 variable region (SEQ ID NO:33)
QVQLVQSGSELKKPGASVKVSCKASGYTFTSYAMNWVRQAPGQGLEWMGWINTY
TGEPTYAAGFTGRFVFSLDTSVSTAYLQISSLKAEDTAVYYCAKYPHYYGSSHWYF
DVWGAGTLVTVSS >anti-VEGF H1.33 variable region (SEQ ID NO:34)
QVQLVQSGSELKKPGASVKVSCKASGYTFTNYGMNWVRQAPGQGLEWMGWINT
YTGNPTYAQGFTGRFVFSLDTSVSTAYLQISSLKAEDTAVYYCAKYPHYYGSSHWY
FDVWGAGTLVTVSS >anti-VEGF H1.34 variable region (SEQ ID NO:35)
QVQLVQSGSELKKPGASVKVSCKASGYTFTSYAMNWVRQAPGQGLEWMGWINTY
TGNPTYAQGFTGRFVFSLDTSVSTAYLQISSLKAEDTAVYFCAKYPHYYGSSHWYF
DVWGAGTLVTVSS >anti-VEGF H1.35 variable region (SEQ ID NO:36)
QIQLVQSGSELKKPGASVKVSCKASGYTFTSYAMNWVRQAPGQGLEWMGWINTY
TGNPTYAQGFTGRFVFSLDTSVSTAYLQISSLKAEDTAVYYCAKYPHYYGSSHWYF
DVWGAGTLVTVSS >anti-VEGF H1.36 variable region (SEQ ID NO:37)
QVQLVQSGSELKKPGASVKVSCKASGYTFTSYAMNWVRQAPGQGLEWMGWINTY
TGNPTYAQGFTGRFVFSLDTSVSTAYLQISSLKAEDTAVYYCAKYPHYYGSSHWYF
DVWGAGTLVTVSS >anti-VEGF H1.37 variable region (SEQ ID NO:38)
QVQLVQSGSELKKPGASVKVSCKASGYTFTSYAMNWVRQAPGQGLEWMGWINTY
TGNPTYAAGFTGRFVFSLDTSVSTAYLQISSLKAEDTAVYYCAKYPHYYGSSHWYF
DVWGAGTLVTVSS >anti-VEGF H1.38 variable region (SEQ ID NO:39)
QVQLVQSGSELKKPGASVKVSCKASGYTFTSYAMNWVRQAPGQGLEWMGWINTY
TGEPTYAQGFTGRFVFSLDTSVSTAYLQISSLKAEDTAVYYCAKYPHYYGSSHWYF
DVWGAGTLVTVSS >anti-VEGF H1.39 variable region (SEQ ID NO:40)
QVQLVQSGSELKKPGASVKVSCKASGYTFTYYAMNWVRQAPGQGLEWMGWINTY
TGEPTYAAGFTGRFVFSLDTSVSTAYLQISSLKAEDTAVYYCAKYPHYYGSSHWYF
DVWGAGTLVTVSS

Figure 16 (cont.)

>anti-VEGF H1.40 variable region (SEQ ID NO:41)
QVQLVQSGSELKKPGASVKVSCKASGYTFTYYAMNWVRQAPGQGLEWMGWINTY
TGNPTYAQGFTGRFVFSLDTSVSTAYLQISSLKAEDTAVYFCAKYPHYYGSSHWYF
DVWGAGTLVTVSS >anti-VEGF H1.41 variable region (SEQ ID NO:42)
QVQLVQSGSELKKPGASVKVSCKASGYTFTYYAMNWVRQAPGQGLEWMGWINTY
TGNPTYAQGFTGRFVFSLDTSVSTAYLQISSLKAEDTAVYYCAKYPHYYGSSHWYF
DVWGAGTLVTVSS >anti-TNF H0 variable region (A2; infliximab) (SEQ ID NO. 213)
EVKLEESGGGLVQPGGSMKLSCVASGFIFSNHWMNWVRQSPEKGLEWVAEIRSK
SINSATHYAESVKGRFTISRDDSKSAVYLQMTDLRTEDTGVYYCSRNYYGSTYDYW
GQGTTLTVSS >framework-optimized anti-TNF variable region (H1) (SEQ ID NO. 214)
EVQLVESGGGLVQPGGSLKLSCAASGFIFSNHWMNWVRQASGKGLEWVGEIRSK
SINSATHYAESVKGRFTISRDDSKSIVYLQMNSLKTEDTAVYYCSRNYYGSTYDYW
GQGTLVTVSS >anti-TNF H1.1 variable region (SEQ ID NO. 215)
EVQLVESGGGLVQPGGSLKLSCAASGFTFSNHWMNWVRQASGKGLEWVGEIRSK
SINSATHYAESVKGRFTISRDDSKSIVYLQMNSLKTEDTAVYYCSRNYYGSTYDYW
GQGTLVTVSS >anti-TNF H1.2 variable region (SEQ ID NO. 216)
EVQLVESGGGLVQPGGSLKLSCAASGFIFSGHWMNWVRQASGKGLEWVGEIRSK
SINSATHYAESVKGRFTISRDDSKSIVYLQMNSLKTEDTAVYYCSRNYYGSTYDYW
GQGTLVTVSS >anti-TNF H1.3 variable region (SEQ ID NO. 217)
EVQLVESGGGLVQPGGSLKLSCAASGFIFSNSWMNWVRQASGKGLEWVGEIRSK
SINSATHYAESVKGRFTISRDDSKSIVYLQMNSLKTEDTAVYYCSRNYYGSTYDYW
GQGTLVTVSS >anti-TNF H1.4 variable region (SEQ ID NO. 218)
EVQLVESGGGLVQPGGSLKLSCAASGFIFSNHAMNWVRQASGKGLEWVGEIRSKS
INSATHYAESVKGRFTISRDDSKSIVYLQMNSLKTEDTAVYYCSRNYYGSTYDYWG
QGTLVTVSS >anti-TNF H1.5 variable region (SEQ ID NO. 219)
EVQLVESGGGLVQPGGSLKLSCAASGFIFSNHWMHWVRQASGKGLEWVGEIRSK
SINSATHYAESVKGRFTISRDDSKSIVYLQMNSLKTEDTAVYYCSRNYYGSTYDYW
GQGTLVTVSS >anti-TNF H1.6 variable region (SEQ ID NO. 220)
EVQLVESGGGLVQPGGSLKLSCAASGFIFSNHWMNWVRQASGKGLEWVGRIRSK
SINSATHYAESVKGRFTISRDDSKSIVYLQMNSLKTEDTAVYYCSRNYYGSTYDYW
GQGTLVTVSS

Figure 16 (cont.)

>anti-TNF H1.7 variable region (SEQ ID NO. 221)
EVQLVESGGGLVQPGGSLKLSCAASGFIFSNHWMNWVRQASGKGLEWVGEIRSK
AINSATHYAESVKGRFTISRDDSKSIVYLQMNSLKTEDTAVYYCSRNYYGSTYDYW
GQGTLVTVSS >anti-TNF H1.8 variable region (SEQ ID NO. 222)
EVQLVESGGGLVQPGGSLKLSCAASGFIFSNHWMNWVRQASGKGLEWVGEIRSK
SNNSATHYAESVKGRFTISRDDSKSIVYLQMNSLKTEDTAVYYCSRNYYGSTYDYW
GQGTLVTVSS >anti-TNF H1.9 variable region (SEQ ID NO. 223)
EVQLVESGGGLVQPGGSLKLSCAASGFIFSNHWMNWVRQASGKGLEWVGEIRSK
SISSATHYAESVKGRFTISRDDSKSIVYLQMNSLKTEDTAVYYCSRNYYGSTYDYW
GQGTLVTVSS >anti-TNF H1.10 variable region (SEQ ID NO. 224)
EVQLVESGGGLVQPGGSLKLSCAASGFIFSNHWMNWVRQASGKGLEWVGEIRSK
SINYATHYAESVKGRFTISRDDSKSIVYLQMNSLKTEDTAVYYCSRNYYGSTYDYW
GQGTLVTVSS >anti-TNF H1.11 variable region (SEQ ID NO. 266)
EVQLVESGGGLVQPGGSLKLSCAASGFIFSNHWMNWVRQASGKGLEWVGEIRSK
SINSATAYAESVKGRFTISRDDSKSIVYLQMNSLKTEDTAVYYCSRNYYGSTYDYW
GQGTLVTVSS >anti-TNF H1.12 variable region (SEQ ID NO. 225)
EVQLVESGGGLVQPGGSLKLSCAASGFIFSNHWMNWVRQASGKGLEWVGEIRSK
SINSATHYAASVKGRFTISRDDSKSIVYLQMNSLKTEDTAVYYCSRNYYGSTYDYW
GQGTLVTVSS >anti-TNF H1.13 variable region (SEQ ID NO. 226)
EVQLVESGGGLVQPGGSLKLSCAASGFIFSNHWMNWVRQASGKGLEWVGEIRSK
SINSATHYAESVKGRFTISRDDSKNIVYLQMNSLKTEDTAVYYCSRNYYGSTYDYW
GQGTLVTVSS >anti-TNF H1.14 variable region (SEQ ID NO. 227)
EVQLVESGGGLVQPGGSLKLSCAASGFIFSNHWMNWVRQASGKGLEWVGEIRSK
SINSATHYAESVKGRFTISRDDSKSTVYLQMNSLKTEDTAVYYCSRNYYGSTYDYW
GQGTLVTVSS >anti-TNF H1.15 variable region (SEQ ID NO. 228)
EVQLVESGGGLVQPGGSLKLSCAASGFIFSNHWMNWVRQASGKGLEWVGEIRSK
SINSATHYAESVKGRFTISRDDSKSIAYLQMNSLKTEDTAVYYCSRNYYGSTYDYW
GQGTLVTVSS >anti-TNF H1.16 variable region (SEQ ID NO. 229)
EVQLVESGGGLVQPGGSLKLSCAASGFIFSNHWMNWVRQASGKGLEWVGEIRSK
SINSATHYAESVKGRFTISRDDSKSIVYLQMNSLKTEDTAVYYCTRNYYGSTYDYW
GQGTLVTVSS

Figure 16 (cont.)

>anti-TNF H1.45 variable region (SEQ ID NO. 230)
EVQLVESGGGLVQPGGSLKLSCAASGFIFSNHWMNWVRQASGKGLEWVGEIRSK
AINYATHYAESVKGRFTISRDDSKSIVYLQMNSLKTEDTAVYYCSRNYYGSTYDYW
GQGTLVTVSS >anti-TNF H1.67 variable region (SEQ ID NO. 231)
EVQLVESGGGLVQPGGSLKLSCAASGFTFSNHWMNWVRQASGKGLEWVGEIRSK
AISYATHYAASVKGRFTISRDDSKNTAYLQMNSLKTEDTAVYYCSRNYYGSTYDYW
GQGTLVTVSS >anti-TNF H1.101 variable region (SEQ ID NO. 232)
EVQLVESGGGLVQPGGSLKLSCAASGFIFSNHWMNWVRQASGKGLEWVGEIRSK
AINYATHYAESVKGRFTISRDDSKSTAYLQMNSLKTEDTAVYYCSRNYYGSTYDYW
GQGTLVTVSS >anti-TNF H1.103 variable region (SEQ ID NO. 233)
EVQLVESGGGLVQPGGSLKLSCAASGFIFSNHWMNWVRQASGKGLEWVGEIRSK
ANNYATHYAASVKGRFTISRDDSKNTAYLQMNSLKTEDTAVYYCSRNYYGSTYDY
WGQGTLVTVSS Light chains:

>murine anti-CD25 VL (L0) (SEQ ID NO:43)
QIVLTQSPAIMSASPGEKVTITCSASSSISYMHWFQQKPGTSPKLWIYTTSNLASGV
PARFSGSGSGTSYSLTISRMEAEDAATYYCHQRSTYPLTFGSGTKLELK >framework-optimized anti-CD25 (L1) (SEQ ID NO:44)
QIVLTQSPATLSLSPGERATLSCRASSSISYMHWFQQKPGQSPQLLIYTTSNLASGV
PARFSGSGSGTDYTLTISSLQPEDFAVYYCHQRSTYPLTFGSGTKLEIK >anti-CD25 L1.1 variable region (SEQ ID NO:45)
QIVLTQSPATLSLSPGERATLSCRASSSISYMHWFQQKPGQSPQLLIYTTSNLASGV
PARFSGSGSGTDYTLTISSLQPEDFAVYYCQQRSTYPLTFGSGTKLEIK >anti-CD25 L1.2 variable region (SEQ ID NO:46)
QIVLTQSPATLSLSPGERATLSCRASSSVSYMHWFQQKPGQSPQLLIYTTSNLASG
VPARFSGSGSGTDYTLTISSLQPEDFAVYYCHQRSTYPLTFGSGTKLEIK >anti-CD25 L1.3 variable region (SEQ ID NO:47)
QIVLTQSPATLSLSPGERATLSCRASSSISYMHWFQQKPGQSPQLLIYTTSNRASGV
PARFSGSGSGTDYTLTISSLQPEDFAVYYCHQRSTYPLTFGSGTKLEIK >anti-CD25 L1.4 variable region (SEQ ID NO:48)
QIVLTQSPATLSLSPGERATLSCRASSSISYLHWFQQKPGQSPQLLIYTTSNLASGV
PARFSGSGSGTDYTLTISSLQPEDFAVYYCHQRSTYPLTFGSGTKLEIK >anti-CD25 L1.5 variable region (SEQ ID NO:49)
EIVLTQSPATLSLSPGERATLSCRASSSISYMHWFQQKPGQSPQLLIYTTSNLASGV
PARFSGSGSGTDYTLTISSLQPEDFAVYYCHQRSTYPLTFGSGTKLEIK

Figure 16 (cont.)

>anti-CD25 L1.6 variable region (SEQ ID NO:50)
QIVLTQSPATLSLSPGERATLSCRASSSISYMHWFQQKPGQSPRLLIYTTSNLASGV
PARFSGSGSGTDYTLTISSLQPEDFAVYYCHQRSTYPLTFGSGTKLEIK >anti-CD25 L1.7 variable region (SEQ ID NO:51)
QIVLTQSPATLSLSPGERATLSCRASSSISYMHWFQQKPGQSPQLLIYTTSNLASGV
PARFSGSGSGTDYTLTISSLEPEDFAVYYCHQRSTYPLTFGSGTKLEIK >anti-CD25 L1.8 variable region (SEQ ID NO:52)
QIVLTQSPATLSLSPGERATLSCRASQSISYMHWFQQKPGQSPQLLIYTTSNLASGV
PARFSGSGSGTDYTLTISSLQPEDFAVYYCHQRSTYPLTFGSGTKLEIK >anti-CD25 L1.9 variable region (SEQ ID NO:53)
QIVLTQSPATLSLSPGERATLSCRASSSISYMHWFQQKPGQAPQLLIYTTSNLASGV
PARFSGSGSGTDYTLTISSLQPEDFAVYYCHQRSTYPLTFGSGTKLEIK >anti-CD25 L1.10 variable region (SEQ ID NO:54)
QIVLTQSPATLSLSPGERATLSCRASSSISYMHWFQQKPGQSPQLLIYTTSNLATGV
PARFSGSGSGTDYTLTISSLQPEDFAVYYCHQRSTYPLTFGSGTKLEIK >anti-CD25 L1.11 variable region (SEQ ID NO:55)
QIVLTQSPATLSLSPGERATLSCRASSSISYMHWFQQKPGQSPQLLIYDTSNLASGV
PARFSGSGSGTDYTLTISSLQPEDFAVYYCHQRSTYPLTFGSGTKLEIK >anti-CD25 L1.12 variable region (SEQ ID NO:56)
QIVLTQSPATLSLSPGERATLSCRASSSISYMHWFQQKPGQSPQLLIYTASNLASGV
PARFSGSGSGTDYTLTISSLQPEDFAVYYCHQRSTYPLTFGSGTKLEIK >anti-CD25 L1.13 variable region (SEQ ID NO:57)
QIVLTQSPATLSLSPGERATLSCRASSSISYMHWFQQKPGQSPQLLIYTTSNLASGIP
ARFSGSGSGTDYTLTISSLQPEDFAVYYCHQRSTYPLTFGSGTKLEIK >anti-CD25 L1.14 variable region (SEQ ID NO:58)
QIVLTQSPATLSLSPGERATLSCRASSSISYMHWFQQKPGQSPQLLIYTTSNLASGV
PARFSGSGSGTDFTLTISSLQPEDFAVYYCHQRSTYPLTFGSGTKLEIK >anti-CD25 L1.15 variable region (SEQ ID NO:59)
QIVLTQSPATLSLSPGERATLSCRASSSISYMAWFQQKPGQSPQLLIYTTSNLASGV
PARFSGSGSGTDYTLTISSLQPEDFAVYYCHQRSTYPLTFGSGTKLEIK >anti-CD25 L1.16 variable region (SEQ ID NO:60)
QIVLTQSPATLSLSPGERATLSCRASSSISYMHWYQQKPGQSPQLLIYTTSNLASGV
PARFSGSGSGTDYTLTISSLQPEDFAVYYCHQRSTYPLTFGSGTKLEIK >anti-CD25 L1.17 variable region (SEQ ID NO:61)
QIVLTQSPATLSLSPGERATLSCRASSSISYMHWFQQKPGQSPQLLIYTTSNLASGV
PARFSGSGSGTDYTLTISSLQPEDFAVYYCHQRSNYPLTFGSGTKLEIK >anti-CD25 L1.18 variable region (SEQ ID NO:62)
QIVLTQSPATLSLSPGERATLSCRASSSISYMHWFQQKPGQSPQLLIYTTSNLASGV
PARFSGSGSGTDYTLTISSLQPEDFAVYYCHQRSTWPLTFGSGTKLEIK

Figure 16 (cont.)

>anti-CD25 L1.19 variable region (SEQ ID NO:63)
QIVLTQSPATLSLSPGERATLSCRASSSISSYMHWFQQKPGQSPQLLIYTTSNLASG
VPARFSGSGSGTDYTLTISSLQPEDFAVYYCHQRSTYPLTFGSGTKLEIK >anti-CD25 L1.20 variable region (SEQ ID NO:64)
EIVLTQSPATLSLSPGERATLSCRASQSVSYLHWYQQKPGQAPRLLIYTTSNRATGI
PARFSGSGSGTDFTLTISSLEPEDFAVYYCHQRSTYPLTFGSGTKLEIK >anti-CD25 L1.43 variable region (SEQ ID NO:65)
EIVLTQSPATLSLSPGERATLSCRASQSVSYLHWYQQKPGQAPRLLIYTTSNRATGI
PARFSGSGSGTDYTLTISSLQPEDFAVYYCHQRSTYPLTFGSGTKLEIK >anti-CD25 L1.48 variable region (SEQ ID NO:66)
EIVLTQSPATLSLSPGERATLSCRASQSVSYMHWYQQKPGQAPRLLIYTTSNRATGI
PARFSGSGSGTDFTLTISSLEPEDFAVYYCHQRSTYPLTFGSGTKLEIK >anti-CD25 L1.56 variable region (SEQ ID NO:67)
QIVLTQSPATLSLSPGERATLSCRASQSVSYLHWFQQKPGQSPQLLIYTTSNRATGI
PARFSGSGSGTDFTLTISSLEPEDFAVYYCHQRSTYPLTFGSGTKLEIK >murine anti-VEGF VL (L0) (SEQ ID NO:68)
DIQMTQTTSSLSASLGDRVIISCSASQDISNYLNWYQQKPDGTVKVLIYFTSSLHSGV
PSRFSGSGSGTDYSLTISNLEPEDIATYYCQQYSTVPWTFGGGTKLEIK >framework-optimized anti-VEGF (L1) (SEQ ID NO:69)
DIQMTQSPSSLSASVGDRVTITCQASQDISNYLNWYQQKPGKTVKVLIYFTSSLHSG
VPSRFSGSGSGTDYTLTISSLQPEDFATYYCQQYSTVPWTFGGGTKLEIK >anti-VEGF L1.1 variable region (SEQ ID NO:70)
DIQMTQSPSSLSASVGDRVTITCQASQDISNYLNWYQQKPGKAVKVLIYFTSSLHSG
VPSRFSGSGSGTDYTLTISSLQPEDFATYYCQQYSTVPWTFGGGTKLEIK >anti-VEGF L1.2 variable region (SEQ ID NO:71)
DIQMTQSPSSLSASVGDRVTITCQASQDISNYLNWYQQKPGKTPKVLIYFTSSLHSG
VPSRFSGSGSGTDYTLTISSLQPEDFATYYCQQYSTVPWTFGGGTKLEIK >anti-VEGF L1.3 variable region (SEQ ID NO:72)
DIQMTQSPSSLSASVGDRVTITCQASQDISNYLNWYQQKPGKTVKLLIYFTSSLHSG
VPSRFSGSGSGTDYTLTISSLQPEDFATYYCQQYSTVPWTFGGGTKLEIK >anti-VEGF L1.4 variable region (SEQ ID NO:73)
DIQMTQSPSSLSASVGDRVTITCQASQDISNYLNWYQQKPGKTVKVLIYDTSSLHSG
VPSRFSGSGSGTDYTLTISSLQPEDFATYYCQQYSTVPWTFGGGTKLEIK >anti-VEGF L1.5 variable region (SEQ ID NO:74)
DIQMTQSPSSLSASVGDRVTITCQASQDISNYLNWYQQKPGKTVKVLIYFASSLHSG
VPSRFSGSGSGTDYTLTISSLQPEDFATYYCQQYSTVPWTFGGGTKLEIK >anti-VEGF L1.6 variable region (SEQ ID NO:75)
DIQMTQSPSSLSASVGDRVTITCQASQDISNYLNWYQQKPGKTVKVLIYFTSN
LHSGVPSRFSGSGSGTDYTLTISSLQPEDFATYYCQQYSTVPWTFGGGTKLEIK

Figure 16 (cont.)

>anti-VEGF L1.7 variable region (SEQ ID NO:76)
DIQMTQSPSSLSASVGDRVTITCQASQDISNYLNWYQQKPGKTVKVLIYFTSSLESG
VPSRFSGSGSGTDYTLTISSLQPEDFATYYCQQYSTVPWTFGGGTKLEIK >anti-VEGF L1.8 variable region (SEQ ID NO:77)
DIQMTQSPSSLSASVGDRVTITCQASQDISNYLNWYQQKPGKTVKVLIYFTSSLHTG
VPSRFSGSGSGTDYTLTISSLQPEDFATYYCQQYSTVPWTFGGGTKLEIK >anti-VEGF L1.9 variable region (SEQ ID NO:78)
DIQMTQSPSSLSASVGDRVTITCQASQDISNYLNWYQQKPGKTVKVLIYFTSSLHSG
VPSRFSGSGSGTDFTLTISSLQPEDFATYYCQQYSTVPWTFGGGTKLEIK >anti-VEGF L1.10 variable region (SEQ ID NO:79)
DIQMTQSPSSLSASVGDRVTITCQASQDISNYLNWYQQKPGKTVKVLIYFTSSLHSG
VPSRFSGSGSGTDYTFTISSLQPEDFATYYCQQYSTVPWTFGGGTKLEIK >anti-VEGF L1.11 variable region (SEQ ID NO:80)
DIQMTQSPSSLSASVGDRVTITCQASQDISNYLNWYQQKPGKTVKVLIYFTSSLHSG
VPSRFSGSGSGTDYTLTISSLQPEDIATYYCQQYSTVPWTFGGGTKLEIK >anti-VEGF L1.12 variable region (SEQ ID NO:81)
DIQMTQSPSSLSASVGDRVTITCQASQDISNYLNWYQQKPGKTVKVLIYFTSSLHSG
VPSRFSGSGSGTDYTLTISSLQPEDFATYYCQQYDTVPWTFGGGTKLEIK >anti-VEGF L1.13 variable region (SEQ ID NO:82)
DIQMTQSPSSLSASVGDRVTITCQASQDISNYLNWYQQKPGKTVKVLIYFTSSLHSG
VPSRFSGSGSGTDYTLTISSLQPEDFATYYCQQYSNVPWTFGGGTKLEIK >anti-VEGF L1.14 variable region (SEQ ID NO:83)
DIQMTQSPSSLSASVGDRVTITCQASQDISNYLNWYQQKPGKTVKVLIYFTSSLHSG
VPSRFSGSGSGTDYTLTISSLQPEDFATYYCQQYSTLPWTFGGGTKLEIK >anti-VEGF L1.15 variable region (SEQ ID NO:84)
DIQMTQSPSSLSASVGDRVTITCQASQDISNYLNWYQQKPGKTVKVLIYFTSSLQSG
VPSRFSGSGSGTDYTLTISSLQPEDFATYYCQQYSTVPWTFGGGTKLEIK >anti-VEGF L1.16 variable region (SEQ ID NO:85)
DIQMTQSPSSLSASVGDRVTITCQASQDISNYLNWYQQKPGKTVKVLIYFTSSLHSG
VPSRFSGSGSGTDYTLTISSLQPEDFATYYCQQYNTVPWTFGGGTKLEIK >anti-VEGF L1.17 variable region (SEQ ID NO:86)
DIQMTQSPSSLSASVGDRVTITCQASQDISNYLNWYQQKPGKTVKVLIYFTSSLHSG
VPSRFSGSGSGTDYTLTISSLQPEDFATYYCQQYYTVPWTFGGGTKLEIK >anti-VEGF L1.18 variable region (SEQ ID NO:87)
DIQMTQSPSSLSASVGDRVTITCQASQDISNYLNWYQQKPGKVVKVLIYFTSSLHSG
VPSRFSGSGSGTDYTLTISSLQPEDFATYYCQQYSTVPWTFGGGTKLEIK
Figure 16 (cont.)

>anti-VEGF L1.19 variable region (SEQ ID NO:88)
DIQMTQSPSSLSASVGDRVTITCQASQDISNYLNWYQQKPGKTVKVLIYFTSSLFSG
VPSRFSGSGSGTDYTLTISSLQPEDFATYYCQQYSTVPWTFGGGTKLEIK

Figure 16 (cont.)

>anti-VEGF L1.20 variable region (SEQ ID NO:89)
DIQMTQSPSSLSASVGDRVTITCQASQDISNYLNWYQQKPGKTVKVLIYFTSSLISG
VPSRFSGSGSGTDYTLTISSLQPEDFATYYCQQYSTVPWTFGGGTKLEIK >anti-VEGF L1.50 variable region (SEQ ID NO:90)
DIQMTQSPSSLSASVGDRVTITCQASQDISNYLNWYQQKPGKAPKVLIYFTSSLHSG
VPSRFSGSGSGTDFTFTISSLQPEDIATYYCQQYSTVPWTFGGGTKLEIK >anti-VEGF L1.51 variable region (SEQ ID NO:91)
DIQMTQSPSSLSASVGDRVTITCQASQDISNYLNWYQQKPGKAPKVLIYFTSSLHSG
VPSRFSGSGSGTDYTLTISSLQPEDFATYYCQQYDNLPWTFGGGTKLEIK >anti-VEGF L1.52 variable region (SEQ ID NO:92)
DIQMTQSPSSLSASVGDRVTITCQASQDISNYLNWYQQKPGKAPKVLIYFASNLETG
VPSRFSGSGSGTDYTLTISSLQPEDFATYYCQQYSTVPWTFGGGTKLEIK >anti-VEGF L1.53 variable region (SEQ ID NO:93)
DIQMTQSPSSLSASVGDRVTITCQASQDISNYLNWYQQKPGKAPKVLIYFTSSLHSG
VPSRFSGSGSGTDFTFTISSLQPEDIATYYCQQYDNLPWTFGGGTKLEIK >anti-VEGF L1.54 variable region (SEQ ID NO:94)
DIQMTQSPSSLSASVGDRVTITCQASQDISNYLNWYQQKPGKAPKVLIYFASNLETG
VPSRFSGSGSGTDFTFTISSLQPEDIATYYCQQYSTVPWTFGGGTKLEIK >anti-VEGF L1.55 variable region (SEQ ID NO:95)
DIQMTQSPSSLSASVGDRVTITCQASQDISNYLNWYQQKPGKAPKVLIYFASNLETG
VPSRFSGSGSGTDYTLTISSLQPEDFATYYCQQYDNLPWTFGGGTKLEIK >anti-VEGF L1.56 variable region (SEQ ID NO:96)
DIQMTQSPSSLSASVGDRVTITCQASQDISNYLNWYQQKPGKAPKVLIYFASNLETG
VPSRFSGSGSGTDFTFTISSLQPEDIATYYCQQYDNLPWTFGGGTKLEIK >anti-VEGF L1.57 variable region (SEQ ID NO:97)
DIQMTQSPSSLSASVGDRVTITCQASQDISNYLNWYQQKPGKAPKVLIYDTSSLHSG
VPSRFSGSGSGTDFTFTISSLQPEDIATYYCQQYDNLPWTFGGGTKLEIK >anti-VEGF L1.58 variable region (SEQ ID NO:98)
DIQMTQSPSSLSASVGDRVTITCQASQDISNYLNWYQQKPGKAPKVLIYDASNLETG
VPSRFSGSGSGTDFTFTISSLQPEDIATYYCQQYSTVPWTFGGGTKLEIK >anti-VEGF L1.59 variable region (SEQ ID NO:99)
DIQMTQSPSSLSASVGDRVTITCQASQDISNYLNWYQQKPGKAPKVLIYDASNLETG
VPSRFSGSGSGTDYTLTISSLQPEDFATYYCQQYDNLPWTFGGGTKLEIK >anti-VEGF L1.60 variable region (SEQ ID NO:100)
DIQMTQSPSSLSASVGDRVTITCQASQDISNYLNWYQQKPGKAPKVLIYDASNLETG
VPSRFSGSGSGTDFTFTISSLQPEDIATYYCQQYDNLPWTFGGGTKLEIK >anti-VEGF L1.61 variable region (SEQ ID NO:101)
DIQMTQSPSSLSASVGDRVTITCQASQDISNYLNWYQQKPGKAPKVLIYFASNLESG
VPSRFSGSGSGTDFTFTISSLQPEDIATYYCQQYSTVPWTFGGGTKLEIK

Figure 16 (cont.)

>anti-VEGF L1.62 variable region (SEQ ID NO:102)
DIQMTQSPSSLSASVGDRVTITCQASQDISNYLNWYQQKPGKAPKVLIYFTSNLETG
VPSRFSGSGSGTDFTFTISSLQPEDIATYYCQQYSTVPWTFGGGTKLEIK >anti-VEGF L1.63 variable region (SEQ ID NO:103)
DIQMTQSPSSLSASVGDRVTITCQASQDISNYLNWYQQKPGKAPKVLIYFASNLESG
VPSRFSGSGSGTDFTFTISSLQPEDIATYYCQQYDNLPWTFGGGTKLEIK >anti-VEGF L1.64 variable region (SEQ ID NO:104)
DIQMTQSPSSLSASVGDRVTITCQASQDISNYLNWYQQKPGKAPKVLIYFTSNLETG
VPSRFSGSGSGTDFTFTISSLQPEDIATYYCQQYDNLPWTFGGGTKLEIK >murine anti-TNF VL (L0) (A2; infliximab) (SEQ ID NO. 234)
DILLTQSPAILSVSPGERVSFSCRASQFVGSSIHWYQQRTNGSPRLLIKYASESMSGI
PSRFSGSGSGTDFTLSINTVESEDIADYYCQQSHSWPFTFGSGTNLEVK >framework-optimized anti-TNF (L1) variable region light chain (SEQ ID NO. 235)
DILLTQSPDFQSVTPKEKVTITCRASQFVGSSIHWYQQKPDQSPKLLIKYASESMSGI
PSRFSGSGSGTDFTLTINSLEAEDAATYYCQQSHSWPFTFGSGTKLEIK >anti-TNF L1.1 variable region light chain (SEQ ID NO. 236)
EILLTQSPDFQSVTPKEKVTITCRASQFVGSSIHWYQQKPDQSPKLLIKYASESMSGI
PSRFSGSGSGTDFTLTINSLEAEDAATYYCQQSHSWPFTFGSGTKLEIK >anti-TNF L1.2 variable region light chain (SEQ ID NO. 237)
DIVLTQSPDFQSVTPKEKVTITCRASQFVGSSIHWYQQKPDQSPKLLIKYASESMSGI
PSRFSGSGSGTDFTLTINSLEAEDAATYYCQQSHSWPFTFGSGTKLEIK >anti-TNF L1.3 variable region light chain (SEQ ID NO. 238)
DILLTQSPDFQSVTPKEKVTITCRASQSVGSSIHWYQQKPDQSPKLLIKYASESMSGI
PSRFSGSGSGTDFTLTINSLEAEDAATYYCQQSHSWPFTFGSGTKLEIK >anti-TNF L1.4 variable region light chain (SEQ ID NO. 239)
DILLTQSPDFQSVTPKEKVTITCRASQFIGSSIHWYQQKPDQSPKLLIKYASESMSGI
PSRFSGSGSGTDFTLTINSLEAEDAATYYCQQSHSWPFTFGSGTKLEIK >anti-TNF L1.5 variable region light chain (SEQ ID NO. 240)
DILLTQSPDFQSVTPKEKVTITCRASQFVGSSLHWYQQKPDQSPKLLIKYASESMSG
IPSRFSGSGSGTDFTLTINSLEAEDAATYYCQQSHSWPFTFGSGTKLEIK >anti-TNF L1.6 variable region light chain (SEQ ID NO. 241)
DILLTQSPDFQSVTPKEKVTITCRASQFVGSSIHWYQQKPDQSPKLLIKYASQSMSGI
PSRFSGSGSGTDFTLTINSLEAEDAATYYCQQSHSWPFTFGSGTKLEIK >anti-TNF L1.7 variable region light chain (SEQ ID NO. 242)
DILLTQSPDFQSVTPKEKVTITCRASQFVGSSIHWYQQKPDQSPKLLIKYASESFSGI
PSRFSGSGSGTDFTLTINSLEAEDAATYYCQQSHSWPFTFGSGTKLEIK >anti-TNF L1.8 variable region light chain (SEQ ID NO. 243)
DILLTQSPDFQSVTPKEKVTITCRASQFVGSSIHWYQQKPDQSPKLLIKYASESMSG
VPSRFSGSGSGTDFTLTINSLEAEDAATYYCQQSHSWPFTFGSGTKLEIK

Figure 16 (cont.)

>anti-TNF L1.9 variable region light chain (SEQ ID NO. 244)
DILLTQSPDFQSVTPKEKVTITCRASQFVGSSIHWYQQKPDQSPKLLIKYASESMSGI
PSRFSGSGSGTDFTLTINSLEAEDAATYYCHQSHSWPFTFGSGTKLEIK >anti-TNF L1.10 variable region light chain (SEQ ID NO. 245)
DILLTQSPDFQSVTPKEKVTITCRASQFVGSSIHWYQQKPDQSPKLLIKYASESMSGI
PSRFSGSGSGTDFTLTINSLEAEDAATYYCQQSSSWPFTFGSGTKLEIK >anti-TNF L1.11 variable region light chain (SEQ ID NO. 246)
DILLTQSPDFQSVTPKEKVTITCRASQFVGSSIHWYQQKPDQSPKLLIKYASESMSGI
PSRFSGSGSGTDFTLTINSLEAEDAATYYCQQSHSLPFTFGSGTKLEIK >anti-TNF L1.12 variable region light chain (SEQ ID NO. 247)
DILLTQSPDFQSVTPKEKVTITCRASQFVGSSIHWYQQKPDQSPKLLIKYASESASGI
PSRFSGSGSGTDFTLTINSLEAEDAATYYCQQSHSWPFTFGSGTKLEIK >anti-TNF L1.13 variable region light chain (SEQ ID NO. 248)
DILLTQSPDFQSVTPKEKVTITCRASQFVGSSIHWYQQKPDQSPKLLIKYASESQSGI
PSRFSGSGSGTDFTLTINSLEAEDAATYYCQQSHSWPFTFGSGTKLEIK >anti-TNF L1.14 variable region light chain (SEQ ID NO. 249)
DILLTQSPDFQSVTPKEKVTITCRASQFVGSSIHWYQQKPDQSPKLLIKYASESMSGI
PSRFSGSGSGTDFTLTINSLEAEDAATYYCQQSYSWPFTFGSGTKLEIK >anti-TNF L1.15 variable region light chain (SEQ ID NO. 250)
DILLTQSPDFQSVTPKEKVTITCRASQFVGSSIHWYQQKPDQSPKLLIKYASESMSGI
PSRFSGSGSGTDFTLTINSLEAEDAATYYCQQSHSTPFTFGSGTKLEIK >anti-TNF L1.30 variable region light chain (SEQ ID NO. 251)
EIVLTQSPDFQSVTPKEKVTITCRASQFVGSSIHWYQQKPDQSPKLLIKYASESFSG
VPSRFSGSGSGTDFTLTINSLEAEDAATYYCQQSHSWPFTFGSGTKLEIK >anti-TNF L1.33 variable region light chain (SEQ ID NO. 252)
EIVLTQSPDFQSVTPKEKVTITCRASQFIGSSLHWYQQKPDQSPKLLIKYASESFSGV
PSRFSGSGSGTDFTLTINSLEAEDAATYYCQQSHSWPFTFGSGTKLEIK Heavy chain CDRs:

>anti-CD25 heavy chain CDR1 (SEQ ID NO:105)
GYRMH

>anti-CD25 heavy chain CDR1 (SEQ ID NO:106)
SYRMH

>anti-CD25 heavy chain CDR2 (SEQ ID NO:107)
WINPNSGGTNYAQKFQG

>anti-CD25 heavy chain CDR2 (SEQ ID NO:108)
YINPNSGGTNYAQKFQG

Figure 16 (cont.)

>anti-CD25 heavy chain CDR2 (SEQ ID NO:109)
YINPSTGYTEYNQKFQG

>anti-CD25 heavy chain CDR3 (SEQ ID NO:110)
GGGVFDY

>anti-VEGF heavy chain CDR1 (SEQ ID NO:111)
NYGMN

>anti-VEGF heavy chain CDR1 (SEQ ID NO:112)
SYAMN

>anti-VEGF heavy chain CDR1 (SEQ ID NO:113)
YYAMN

>anti-VEGF heavy chain CDR2 (SEQ ID NO:114)
WINTYTGEPTYAAGFTG

>anti-VEGF heavy chain CDR2 (SEQ ID NO:115)
WINTNTGNPTYAQGFTG

>anti-VEGF heavy chain CDR2 (SEQ ID NO:116)
WINTYTGNPTYAQGFTG

>anti-VEGF heavy chain CDR3 (SEQ ID NO:117)
YPHYYGSSHWYFDV

>anti-TNF heavy chain CDR1(SEQ ID NO. 253)
NHWMN

>anti-TNF heavy chain CDR2 (SEQ ID NO. 254)
EIRSKSINSATHYAESVKG

>anti-TNF heavy chain CDR2 (SEQ ID NO. 255)
EIRSKAINYATHYAESVKG

>anti-TNF heavy chain CDR2 (SEQ ID NO. 256)
EIRSKAISYATHYAASVKG

>anti-TNF heavy chain CDR2 (SEQ ID NO. 257)
EIRSKANNYATHYAASVKG

>anti-TNF heavy chain CDR3 (SEQ ID NO. 258)
NYYGSTYDY

Light chain CDRs:

>anti-CD25 light chain CDR1 (SEQ ID NO:118)
RASQSVSYLH

Figure 16 (cont.)

>anti-CD25 light chain CDR1 (SEQ ID NO:119)
SASSSISYMH

>anti-CD25 light chain CDR1 (SEQ ID NO:120)
RASSSISYMH

>anti-CD25 light chain CDR1 (SEQ ID NO:121)
RASQSVSYMH

>anti-CD25 light chain CDR2 (SEQ ID NO:122)
TTSNLAS

>anti-CD25 light chain CDR2 (SEQ ID NO:123)
TTSNRAT

>anti-CD25 light chain CDR3 (SEQ ID NO:124)
HQRSTYPLT

>anti-VEGF light chain CDR1 (SEQ ID NO:125)
QASQDISNYLN

>anti-VEGF light chain CDR2 (SEQ ID NO:126)
FASNLET

>anti-VEGF light chain CDR2 (SEQ ID NO:127)
FTSSLHS

>anti-VEGF light chain CDR2 (SEQ ID NO:128)
DTSSLHS

>anti-VEGF light chain CDR2 (SEQ ID NO:129)
DASNLET

>anti-VEGF light chain CDR2 (SEQ ID NO:130)
FASNLES

>anti-VEGF light chain CDR2 (SEQ ID NO:131)
FTSNLET

>anti-VEGF light chain CDR3 (SEQ ID NO:132)
QQYSTVPWT

>anti-VEGF light chain CDR3 (SEQ ID NO:133)
QQYDNLPWT

>anti-TNF light chain CDR1 (SEQ ID NO. 259)
RASQFVGSSIH

>anti-TNF light chain CDR1 (SEQ ID NO. 260)
RASQFVGSSIH

Figure 16 (cont.)

>anti-TNF light chain CDR1 (SEQ ID NO. 261)
RASQFIGSSLH

>anti-TNF light chain CDR2 (SEQ ID NO. 262)
YASESMS

>anti-TNF light chain CDR2 (SEQ ID NO. 263)
YASESFS

>anti-TNF light chain CDR3 (SEQ ID NO. 264)
QQSHSWPFT

HUMAN EQUIVALENT MONOCLONAL ANTIBODIES ENGINEERED FROM NONHUMAN VARIABLE REGIONS

This application claims the benefit under 35 U.S.C. §119 (e) to 61/046,399, filed Apr. 18, 2008; 61/115,449, filed Nov. 17, 2008; and, 61/120,675, filed Dec. 8, 2008 all of which are expressly incorporated by reference in their entirety.

FIELD OF THE INVENTION

The present invention is directed to the creation of human equivalent CDRs and antibodies containing them.

BACKGROUND OF THE INVENTION

Monoclonal antibodies (mAbs) have become an important class of therapeutics, and there are currently approved mAbs available to treat patients suffering from various types of cancers and autoimmune disorders. The hybridoma approach (Kohler and Milstein, 1975, *Nature* 256:495-497) remains the most prevalent way to generate mAbs with high affinity and specificity to a target of interest. However, mAbs generated in this way are of non-human origin (usually murine) and are highly immunogenic when administered to human patients.

Several methods have been introduced in order to decrease the potential risk of immunogenicity with antibodies isolated from hybridomas, namely chimerization and humanization. Creation of chimeric antibodies, composed of murine variable regions and human constant regions (Morrison, et al., 1984, *Proc Natl Acad Sci USA* 81:6851-6855), was the first such method. However, since a significant portion of the antibody remains non-human, these mAbs still pose a risk of eliciting an immune response. A logical next step was the humanization, or engineering of the variable regions of these mAbs to contain more human sequence content. It was found that the murine complementarity-determining regions (CDRs), which are the principle components of the antibody that confer antigen specificity, could be "grafted" onto human frameworks (FRs) to create an antibody with higher human sequence content. This process, known as CDR-grafting (Jones, et al., 1986, *Nature* 321:522-525), was the first described method of antibody humanization. Since then, several methods of humanization have been described including resurfacing (Roguska, et al., 1994, *Proc Natl Acad Sci USA* 91:969-973), specificity-determining residue (SDR) grafting (Kashmiri, et al., 2005, *Methods* 36:25-34), superhumanization (Hwang, et al., 2005, *Methods* 36:35-42), human string content optimization (Lazar, et al., 2007, *Mol Immunol* 44:1986-1998), and framework shuffling (Dall'Acqua, et al., 2005, *Methods* 36:43-60; Damschroder, et al., 2007, *Mol Immunol* 44:3049-3060). The underlying assumption of all these methods is that the greater global sequence identity of the humanized sequence to a natural human sequence results in a lower risk of immunogenicity. However, due to the perceived risk of losing antigen affinity, none of these methods substantially engineer the CDRs, and as such none of these humanization methods reach the global sequence identity levels of human antibodies as they still contain mostly non-human CDRs.

More recently, "fully-human" mAbs generated from recombinant human antibody libraries (Griffiths, et al., 1994, *Embo J* 13:3245-3260; Knappik, et al., 2000, *J Mol Biol* 296:57-86) or transgenic mice comprising human germline configuration immunoglobulin gene sequences (Lonberg, 2005, *Nat Biotechnol* 23:1117-1125; Green, et al., 1994, *Nat Genet* 7:13-21; Lonberg, et al., 1994, *Nature* 368:856-859) have emerged as alternatives to murine generated and subsequently humanized mAbs. These mAbs have both high affinity as well as high human sequence content. Yet there remain a large number of murine antibodies with well-characterized and desirable properties. Moreover, hybridoma technology remains an accessible, efficient, and effective method for generating high quality mAbs. Thus, there is a need for efficient methods to combine the ease of creating high affinity and specificity non-human mAbs from hybridomas with the high human sequence content and expected low immunogenicity of fully-human mAbs. The current invention addresses this need.

BRIEF SUMMARY OF THE INVENTION

The invention disclosed herein provides a novel method for engineering human equivalent antibody variable regions from non-human variable regions, and in some cases, from variable regions in antibodies produced in transgenic mice and/or humans, if the antibodies are immunogenetic.

In one aspect, the invention provides a method of producing an immunoglobulin which specifically binds to an antigen, the method comprising: a) comparing a parent antibody variable region amino acid sequence comprising less than 85% identity in V- and J-segments to a human germline V- and J-segment against a collection of human germline V- and J-segment amino acid sequences; b) scoring the collection of human germline V- and J-segments based on the number of identities to the parent antibody variable region amino acid sequence; c) selecting the human germline V- and J-segments with the highest score in step (b); d) constructing variant immunoglobulin(s) comprising the parent antibody variable region amino acid sequence in (a) and an amino acid substitution selected from the human germline V- and J-segment in step (c) at a position in which the amino acids in the parent antibody variable region and human germine V- and J-segment differ; e) measuring antigen binding of the variant immunoglobulin(s) in step (d) to obtain affinity constants; f) selecting the variants in step (e) which have an affinity constant that is no less than two-fold of that of the parent antibody variable region immunoglobulin; h) combining the variants in step (f) to create an antibody variable region sequence comprising greater than 85% identity in V- and J-segments to a human germine V- and J-segment.

In some aspects, the identity of the heavy chain is at least about 90%, or at least about 95%. In additional aspects, the identity of the light chain is at least about 90% or at least about 95%.

In additional aspects, the plurality of the at least four amino with an identity to the parent antibody acids are outside the heavy chain CDR3.

In some aspects, the plurality of the at least four amino acids with an identity to the parent antibody are within CDR1 or CDR2 of the heavy chain or the light chain.

In an additional aspect, one or more of the variant antibodies generated using these methods retains at least all the affinity for the antigen of the parent antibody Fv domain. In some aspects, the variant antibodies have no less than about a two fold decrease in affinity binding, and in some embodiments, the variant antibodies have no less than about a three fold decrease.

In some aspects, the method is performed on an antibody comprising a parent antibody Fv domain, wherein the parent antibody Fv domain comprises residues 1-94 and 100-113 of a heavy chain Fv domain and residues 1-107 of a light chain Fv domain, wherein the numbering is according to the system of Kabat et al. In this aspect, the parent antibody Fv domain comprises complimentarity determining regions (CDRs) derived from non-human germline sequences. After the method is done, the identity of residues 1-94 of the heavy chain of the variant antibody Fv domain to a human V-region germline and residues 100-113 of the heavy chain of the variant antibody Fv domain to a human J-region germline is at least 85%. In addition, the identity of residues 1-95 of the light chain of the variant antibody Fv domain to a human V-region germline and residues 96-107 of the light chain of the variant antibody Fv domain to a human J-region germline is at least 85% and wherein the variant antibody Fv domain comprises at least four amino acids with an identity to the parent antibody Fv domain but not an identity to the human germline sequence. Some embodiments utilize more than 4 different amino acids, including from about 4 to 15, 4 to 10, 5 to 10 and 5 to 8, with all combinations of ranges possible.

It is an object of the present invention to provide protein variants of a parent protein that are engineered using the methods described herein. In a preferred embodiment, the parent protein is an immunoglobulin.

It is an object of the present invention to provide experimental methods for screening and testing the protein variants of the present invention.

The present invention provides isolated nucleic acids encoding the protein variants described herein. The present invention provides vectors comprising the nucleic acids, optionally, operably linked to control sequences. The present invention provides host cells containing the vectors, and methods for producing and optionally recovering the protein variants.

The present invention provides compositions comprising the protein variants described herein, and a physiologically or pharmaceutically acceptable carrier or diluent.

The present invention provides novel antibodies and Fc fusions that comprise the protein variants disclosed herein. The novel antibodies and Fc fusions may find use in a therapeutic product.

The present invention provides therapeutic treatment and diagnostic uses for the protein variants disclosed herein.

BRIEF DESCRIPTION OF THE DRAWINGS

The following drawings further illustrate aspects of the invention, and are not meant to constrain the present invention to any particular application or theory of operation.

FIG. 3. Sequences of CDR and $V_H/V_L$ interface positions, antigen binding data, and humanness scores for anti-CD25 variants. Anti-CD25 H0L0 is the chimeric form of the anti-TAC antibody and anti-CD25 H1L1 is the framework optimized variable region antibody. Positions in framework optimized anti-CD25 H1L1 which differ from the closest identity human germline sequences were changed to the corresponding germline amino acid and binding to CD25 was measured with Biacore. Shaded residues indicate differences between each variant and anti-CD25 H1L1. The number of total human 9-mers and identities to the closest human germline for each $V_H$ and $V_L$ pair is also shown.

FIG. 5. Sequences of CDR and $V_H/V_L$ interface positions, antigen binding data, and humanness scores for anti-CD25 combination variants. Anti-CD25 H0L0 is the chimeric form of the anti-TAC antibody and anti-CD25 H1L1 is the framework optimized variable region antibody. Binding data and humanness scores from the anti-CD25 single variants were used to design a library of combination variants that would maximize humanness scores and maintain antigen affinity. Binding to CD25 was measured with Biacore, and shaded residues indicate differences between each variant and anti-CD25 H1L1. The number of total human 9-mers and identities to the closest human germline V and J regions for each $V_H$ and $V_L$ pair is also shown. Fold change in the dissociation constant ($K_d$) for human equivalent anti-CD25 combination variants compared to the chimeric antibody anti-CD25 H0L0 is listed.

FIG. 6. Biacore binding data for anti-CD25 variants binding to CD25. The top panel shows binding data for 25 nM CD25 binding to anti-CD25 H0L0, anti-CD25H1.12L1, anti-CD25 H1L1.20, anti-CD25 H1.12L1.20, and daclizumab immobilized on Protein A on a CM5 chip. The bottom panel shows a plot of affinity vs. humanness for anti-CD25 H0L0 (murine Fv), anti-CD25 H1 L1 (framework optimized), engineered human equivalent anti-CD25 $V_H/V_L$ pairs, and human equivalent anti-CD25 H1.12_L1.20.

FIG. 10. Biacore binding data for anti-VEGF Fab variants binding to VEGF. The top panel shows binding data for 100 nM of anti-VEGF H0L0 (murine Fv), anti-VEGF H1.33L1.51, anti-VEGF H1.33L1.55, and bevacizumab binding to immobilized VEGF on a CM5 chip. The bottom panel shows a bar graph of the dissociation constants of these variants.

FIG. 11. Sequences of CDR and interface positions, binding data, and humanness scores of anti-VEGF variant Fabs. Binding data and humanness scores from anti-VEGF single variants were used to design a library of combination variants that would maximize humanness scores and maintain antigen affinity. Binding to VEGF was measured with Biacore, and shaded residues indicate differences between each variant and anti-VEGF H1L1. The number of total human 9-mers and identities to the closest human germline V and J regions for each $V_H$ and $V_L$ pair is also shown. Fold change in the dissociation constant $(K_d)$ for human equivalent anti-VEGF combination variants compared to the chimeric antibody anti-VEGF H0L0 is listed.

FIG. 12. Sequence properties and final affinity results for engineered mAbs. Number of CDR mutations, percent of CDR changed, final CDR humanness, and fold affinity change relative to H0L0 are listed for the three engineered mAbs anti-CD25H1.12L1.20, anti-VEGF H1.33L1.55, and anti-TNF H1.103L1.33. VH-CDR3 is not included in the total percent CDR humanness calculations. Number of mutations are relative to the H0L0 mAbs with murine Fv.

FIG. 14. Listing of humanness scores for the approved and marketed murine, chimeric, and humanized monoclonal antibodies as well as several fully-human monoclonal antibodies in clinical development. The fully-human antibodies anti-CD25H1.12L1.20, anti-VEGF H1.33L1.55, and anti-TNF H1.103L1.33 engineered in this invention are shown to be comparable to the fully-human antibodies from transgenic mice and human phage display technologies.

FIG. 15. (SEQ ID NO: 166-212 and SEQ ID NO: 265) Heavy chain and light chain variable region sequences for antibodies listed in FIG. 14 with murine and humanized variable regions that may benefit from the fully-human engineering method FIG. 16. (SEQ ID NO: 1-42; SEQ ID NO 213-224; SEQ ID NO: 266; SEQ ID NO: 225-233; SEQ ID NO: 43-104; SEQ ID NO: 234-252; SEQ ID NO 105-117; SEQ ID NO: 253-258; SEQ ID NO: 118-133; SEQ ID NO: 259-264). Sequences of the invention

DETAILED DESCRIPTION OF THE INVENTION

Definitions

Figure 1:
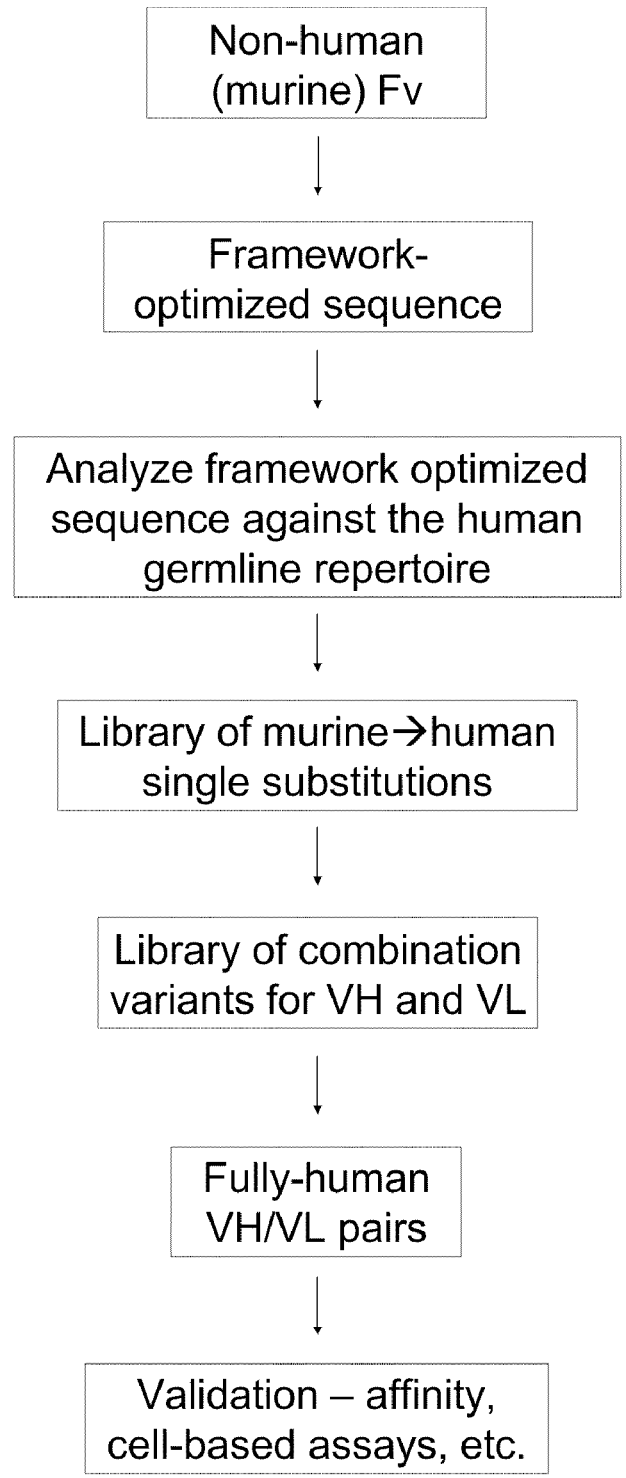
FIG. 1. Diagram illustrating the process of the invention in which murine antibody variable region sequences are engineered to be similar to sequences of human equivalent antibody variable regions.

In order that the invention may be more completely understood, several definitions are set forth below. Such definitions are meant to encompass grammatical equivalents.

By "affinity" as used herein is meant the propensity of one chemical species to separate or dissociate reversibly from another chemical species. In the present invention, the two chemical species most typically are represented by a protein and its ligand, more specifically an antibody and its target antigen. Affinity herein is measured by the equilibrium constant of dissociation $(K_d$ or Kd$)$ that defines the binding between the two chemical species. The $K_d$ defines how tightly the species bind one another. The smaller the dissociation constant, the more tightly bound the ligand is, or the higher the affinity between ligand and protein. For example, an antigen with a nanomolar (nM) dissociation constant binds more tightly to a particular antibody than a ligand with a micromolar (µM) dissociation constant. By "greater affinity" or "improved affinity" or "enhanced affinity" or "better affinity" than a parent polypeptide, as used herein is meant that a protein variant binds to its ligand with a significantly higher equilibrium constant of association $(K_A$ or Ka$)$ or lower equilibrium constant of dissociation $(K_d$ or Kd$)$ than the parent protein when the amounts of variant and parent polypeptide in the binding assay are essentially the same. For example, in the context of antibodies, a variant antibody may have greater affinity to the antigen that its parent antibody, for example when the CDRs are humanized, as described herein. Alternatively, and Fc polypeptide may have greater affinity to an Fc receptor, for example, when the Fc variant has greater affinity to one or more Fcγ receptors or the FcRn receptor. IN general, the binding affinity is determined, for example, by the binding methods disclosed herein, including but not limited to Biacore™ assays, by one skilled in the art. Accordingly, by "reduced affinity" as compared to a parent protein as used herein is meant that aprotein variant binds its ligand with significantly lower $K_a$ or higher $K_d$ than the parent protein. Again, in the context of antibodies, this can be either to the target antigen, or to a receptor such as an Fc receptor. Greater or reduced affinity can also be defined relative to an absolute level of affinity. For example, greater or enhanced affinity may mean having a $K_d$ lower than about 10 nM, for example between about 1 nM-about 10 nM, between about 0.1-about 10 nM, or less than about 0.1 nM.

By "amino acid" and "amino acid identity" as used herein is meant one of the 20 naturally occurring amino acids or any non-natural analogues that may be present at a specific, defined position.

By "amino acid modification" herein is meant an amino acid substitution, insertion, and/or deletion in a polypeptide sequence. The preferred amino acid modification herein is a substitution. By "amino acid modification" herein is meant an amino acid substitution, insertion, and/or deletion in a polypeptide sequence. By "amino acid substitution" or "substitution" herein is meant the replacement of an amino acid at a given position in a protein sequence with another amino acid. For example, the substitution Y50W refers to a variant of a parent polypeptide, in which the tyrosine at position 50 is replaced with tryptophan. By "amino acid insertion" or "insertion" as used herein is meant the addition of an amino acid at a particular position in a parent polypeptide sequence, usually denoted herein and in the incorporated documents by a "^" after the residue where the insertion occurs. By "amino acid deletion" or "deletion" as used herein is meant the removal of an amino acid at a particular position in a parent polypeptide sequence, usually denoted herein and in the incorporated documents by a "#" after the residue to be deleted.

By "antibody" herein is meant a protein consisting of one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (υ), delta (δ), gamma (γ), sigma (σ), and alpha (α) which encode the IgM, IgD, IgG (IgG1, IgG2, IgG3, and IgG4), IgE, and IgA (IgA1 and IgA2) isotypes respectively. Antibody herein is meant to include full length antibodies and antibody fragments, and may refer to a natural antibody from any organism, an engineered antibody, or an antibody generated recombinantly for experimental, therapeutic, or other purposes. Antibodies include, include, but not limited full length antibodies, antibody fragments, single chain antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

In one embodiment, the antibody is an antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment, which consists of a single variable domain, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site, (viii) bispecific single chain Fv dimers, and (ix) "diabodies" or "triabodies", multivalent or multispecific fragments constructed by gene fusion. The antibody fragments may be modified. For example, the molecules may be stabilized by the incorporation of disulphide bridges linking the VH and VL domains. Examples of antibody formats and architectures are described in Holliger & Hudson, 2006, Nature Biotechnology 23(9):1126-1136, and Carter 2006, Nature Reviews Immunology 6:343-357 and references cited therein, all expressly incorporated by reference.

In one embodiment, an antibody disclosed herein may be a multispecific antibody, and notably a bispecific antibody, also sometimes referred to as "diabodies". These are antibodies that bind to two (or more) different antigens. Diabodies can be manufactured in a variety of ways known in the art, e.g., prepared chemically or from hybrid hybridomas. In one embodiment, the antibody is a minibody. Minibodies are minimized antibody-like proteins comprising a scFv joined to a CH3 domain. In some cases, the scFv can be joined to the Fc region, and may include some or all of the hinge region. For a description of multispecific antibodies see Holliger & Hudson, 2006, Nature Biotechnology 23(9):1126-1136 and references cited therein, all expressly incorporated by reference.

By "constant region" of an antibody as defined herein is meant the region of the antibody that is encoded by one of the light or heavy chain immunoglobulin constant region genes. By "constant light chain" or "light chain constant region" as used herein is meant the region of an antibody encoded by the kappa (Cκ) or lambda (Cλ) light chains. The constant light chain typically comprises a single domain, and as defined herein refers to positions 108-214 of Cκ, or Cλ, wherein numbering is according to the EU index. By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU index.

By "corresponding" or "equivalent" residues as meant herein are residues that represent similar or homologous sequence and/or structural environments between a first and second protein, or between a first protein and set of multiple proteins. In order to establish homology, the amino acid sequence of a first protein is directly compared to the sequence of a second protein. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first protein are defined. Alignment of conserved residues preferably should conserve 100% of such residues. However, alignment of greater than 75% or as little as 50% of conserved residues is also adequate to define equivalent residues. Corresponding residues may also be defined by determining structural homology between a first and second protein that is at the level of tertiary structure for proteins whose structures have been determined. In this case, equivalent residues are defined as those for which the atomic coordinates of two or more of the main chain atoms of a particular amino acid residue of the proteins (N on N, CA on CA, C on C and O on O) are within 0.13 nm and preferably 0.1 nm of each other after alignment. Alignment is achieved after the best model has been oriented and positioned to give the maximum overlap of atomic coordinates of non-hydrogen protein atoms of the proteins.

By "CDR" as used herein is meant a Complementarity Determining Region of an antibody variable domain. Systematic identification of residues included in the CDRs have been developed by Kabat (Kabat et al., 1991, Sequences of Proteins of Immunological Interest, 5th Ed., United States Public Health Service, National Institutes of Health, Bethesda) and alternately by Chothia (Chothia & Lesk, 1987, J. Mol. Biol. 196: 901-917; Chothia et al., 1989, Nature 342: 877-883; Al-Lazikani et al., 1997, J. Mol. Biol. 273: 927-948). For the purposes of the present invention, CDRs are defined as a slightly smaller set of residues than the CDRs defined by Chothia. VL CDRs are herein defined to include residues at positions 27-32 (CDR1), 50-56 (CDR2), and 91-97 (CDR3), wherein the numbering is according to Chothia. Because the VL CDRs as defined by Chothia and Kabat are identical, the numbering of these VL CDR positions is also according to Kabat. VH CDRs are herein defined to include residues at positions 27-33 (CDR1), 52-56 (CDR2), and 95-102 (CDR3), wherein the numbering is according to Chothia. These VH CDR positions correspond to Kabat positions 27-35 (CDR1), 52-56 (CDR2), and 95-102 (CDR3).

By "Fab" or "Fab region" as used herein is meant the polypeptide that comprises the VH, $CH_1$, VL, and CL immunoglobulin domains. Fab may refer to this region in isolation, or this region in the context of a full length antibody, antibody fragment or Fab fusion protein, or any other antibody embodiments as outlined herein.

By "Fv" or "Fv fragment" or "Fv region" as used herein is meant a polypeptide that comprises the VL and VH domains of a single antibody.

By "framework" as used herein is meant the region of an antibody variable domain exclusive of those regions defined as CDRs. Each antibody variable domain framework can be further subdivided into the contiguous regions separated by the CDRs (FR1, FR2, FR3 and FR4).

By "germline" as used herein is meant the set of sequences that compose the natural genetic repertoire of antibodies, and its associated alleles.

By "host" as used herein is meant a family, genus, species or subspecies, group of individuals or even a single individual. A host group of individuals can be selected for based upon a variety of criteria, such as MHC allele composition, etc. In a preferred embodiment, a host is canine, murine, primate, or human. In the most preferred embodiment, a host is human. In the context of protein production, a "host cell" is the cell in which the protein is produced, and includes a wide variety of possible hosts, as outlined below, including, but not limited to, mammalian cells, yeast cells, fungal cells, bacterial cells (including *E. coli*), etc.

By "host string" or "host sequence" as used herein is meant a string or sequence that either encodes any part of a naturally occurring host protein (in the case of a nucleic acid sequence) or is any part of a naturally occurring host protein amino acid sequence. In general, as generally outlined in US Publication No. 20080167449, hereby incorporated by reference in its entirety, and particularly for the definitions and methods, a host string is a contiguous sequence of some number of amino acids identical to a naturally occurring protein. In the context of the present invention, the "host string" frequently refers to a partial contiguous sequence of a germline sequence.

By "humanized" antibody as used herein is meant an antibody comprising a human framework region and one or more CDR's from a non-human (usually mouse or rat) antibody. The non-human antibody providing the CDR's is called the "donor" and the human immunoglobulin providing the framework is called the "acceptor". One says that the donor antibody has been "humanized", by the process of "humanization".

By "human equivalent CDR" or "human-like CDR" herein is meant at least one CDR, generally a non-human CDR, that has at least one amino acid substitution that brings the identity of the CDR region closer to at least one CDR of a naturally occurring germline sequence.

By "identity" as used herein is meant the number of residues in a first sequence that are identical to the residues in a second sequence after alignment of the sequences to achieve the maximum identity.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, as illustrated in FIG. 1, Fc comprises immunoglobulin domains Cgamma2 and Cgamma3 (C$\gamma$2 and C$\gamma$3) and the hinge between Cgamma1 (C$\gamma$1) and Cgamma2 (C$\gamma$2). Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

By "Fc fusion" as used herein is meant a protein wherein one or more polypeptides or small molecules is operably linked to an Fc region or a derivative thereof. Fc fusion is herein meant to be synonymous with the terms "immunoadhesin", "Ig fusion", "Ig chimera", and "receptor globulin" (sometimes with dashes) as used in the prior art (Chamow et al., 1996, *Trends Biotechnol* 14:52-60; Ashkenazi et al., 1997, *Curr Opin Immunol* 9:195-200. incorporated by reference). An Fc fusion combines the Fc region of an immunoglobulin with a fusion partner, which in general can be any protein or small molecule. The role of the non-Fc part of an Fc fusion, i.e. the fusion partner, may be to mediate target binding, and thus it is functionally analogous to the variable regions of an antibody.

By "Fc gamma receptor" or "Fc$\gamma$R" as used herein is meant any member of the family of proteins that bind the IgG antibody Fc region and are substantially encoded by the Fc$\gamma$R genes. In humans this family includes but is not limited to Fc$\gamma$RI (CD64), including isoforms Fc$\gamma$RIa, Fc$\gamma$RIb, and Fc$\gamma$RIc; Fc$\gamma$RII (CD32), including isoforms Fc$\gamma$RIIa (including allotypes H131 and R131), Fc$\gamma$RIIb (including Fc$\gamma$RIIb-1 and Fc$\gamma$RIIb-2), and Fc$\gamma$RIIc; and Fc$\gamma$RIII (CD16), including isoforms Fc$\gamma$RIIIa (including allotypes V158 and F158) and Fc$\gamma$RIIIb (including allotypes Fc$\gamma$RIIIb-NA1 and Fc$\gamma$RIIIb-NA2), as well as any undiscovered human Fc$\gamma$Rs or Fc$\gamma$R isoforms or allotypes. An Fc$\gamma$R may be from any organism, including but not limited to humans, mice, rats, rabbits, and monkeys. Mouse Fc$\gamma$Rs include but are not limited to Fc$\gamma$RI (CD64), Fc$\gamma$RII (CD32), Fc$\gamma$RIII (CD16), and Fc$\gamma$RIII-2 (CD16-2), as well as any undiscovered mouse Fc$\gamma$Rs or Fc$\gamma$R isoforms or allotypes.

By "Fc ligand" or "effector ligand" as used herein is meant a molecule, preferably a polypeptide, from any organism that binds to the Fc region of an antibody to form an Fc/Fc ligand complex. Binding of an Fc ligand to Fc preferably elicits or more effector functions. Fc ligands include but are not limited to Fc receptors, Fc$\gamma$Rs, Fc$\alpha$Rs, Fc$\epsilon$Rs, FcRn, C1q, C3, mannan binding lectin, mannose receptor, staphylococcal protein A, streptococcal protein G, and viral Fc$\gamma$R. Fc ligands also include Fc receptor homologs (FcRH), which are a family of Fc receptors that are homologous to the Fc$\gamma$Rs (Davis et al., 2002, *Immunological Reviews* 190:123-136, incorporated by reference). Fc ligands may include undiscovered molecules that bind Fc.

By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoglobulin (Ig) domain" herein is meant a region of an immunoglobulin that exists as a distinct structural entity as ascertained by one skilled in the art of protein structure. Ig domains typically have a characteristic $\beta$-sandwich folding topology. The known Ig domains in the IgG class of antibodies are $V_H$, C$\gamma$1, C$\gamma$2, C$\gamma$3, $V_L$, and $C_L$.

By "full length antibody" as used herein is meant the structure that constitutes the natural biological form of an antibody, including variable and constant regions. For example, in most mammals, including humans and mice, the full length antibody of the IgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, C$\gamma$1, C$\gamma$2, and C$\gamma$3. In some mammals, for example in camels and llamas, IgG antibodies may consist of only two heavy chains, each heavy chain comprising a variable domain attached to the Fc region.

By "humanlike antibody" or "high human antibody" as used herein is meant an antibody whose variable heavy and light chains have sequences that are greater than about 85% identical to at least one sequence in a human germline immunoglobulin gene sequence, or sequences that have greater than 52% of their 9-mers that are a perfect match with at least one 9-mer in a human germline immunoglobulin gene sequence.

By "immune epitope" or "epitope" herein is meant a linear sequence of amino acids that is located in a protein of interest. Epitopes may be analyzed for their potential for immunogenicity. Epitopes may be any length, preferably 9-mers.

By "immunogenicity" herein is meant the ability of a protein to elicit an immune response, including but not limited to production of neutralizing and non-neutralizing antibodies, formation of immune complexes, complement activation, mast cell activation, inflammation, and anaphylaxis.

By "immunoglobulin (Ig)" herein is meant a protein consisting of one or more proteins substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoglobulin (Ig) domain" herein is meant a region of an immunoglobulin that exists as a distinct structural entity as ascertained by one skilled in the art of protein structure. Ig domains typically have a characteristic β-sandwich folding topology. The known Ig domains in the IgG class of antibodies are $V_H$, Cγ1, Cγ2, Cγ3, $V_L$, and $C_L$.

By "IgG" or "IgG immunoglobulin" as used herein is meant a polypeptide belonging to the class of antibodies that are substantially encoded by a recognized immunoglobulin gamma gene. In humans this class comprises the subclasses or isotypes IgG1, IgG2, IgG3, and IgG4. By "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM, IgD, and IgE. Included in the definition of "IgG" are IgG fusions, where the IgG fusion contains sequences from two or more IgG molecules. For example, IgG1/2 fusions find use in a number of applications and are described in US Publication Nos. US Publication Nos. 2004/0132101, 2005/0054832, 2006/0024298, 2006/0121032, 2006/0235208, 2007/01481702007/0275460, herein incorporated by reference in their entirety. Also included in the definition of IgG molecules are other variant IgGs, such as IgG1 variants that include amino acid substitutions in the Fc region, as described in US Publication Nos. 2004/0132101, 2005/0054832, 2006/0024298, 2006/0121032, 2006/0235208, 2007/01481702007/0275460, PCT US04/077250, herein incorporated by reference in their entirety.

By "natural sequence" or "natural protein" as used herein is meant a protein that has been determined to exist absent any experimental modifications. Also included are sequences that can be predicted to exist in nature based on experimentally determined sequences. An example of such a predicted sequence is an antibody that can be predicted to exist based on the established patterns of germline recombination. In this case the large size of the predicted antibody repertoire makes the actual experimental determination of all mature recombined antibodies not practical.

By "parent" or "parent protein" as used herein is meant a protein that is subsequently modified to generate a variant. The parent protein may be a naturally occurring protein, or a variant or engineered version of a naturally occurring protein. Parent protein may refer to the protein itself, compositions that comprise the parent protein, or the amino acid sequence that encodes it. Accordingly, by "parent antibody" as used herein is meant an antibody that is subsequently modified to generate a variant antibody. Accordingly, by "parent sequence" as used herein is meant the sequence that encodes the parent protein or parent antibody. Accordingly, by "Parent CDR" as used herein is meant a CDR that is modified to generate a variant, e.g. a humanized CDR, and by "Parent antibody" as used herein is meant an antibody that is modified to generate a variant antibody, in some cases within at least one CDR region.

By "position" as used herein is meant a location in the sequence of a protein. Positions may be numbered sequentially, or according to an established format, for example Kabat, Chothia, and/or the EU index as in Kabat.

By "protein" herein is meant at least two covalently attached amino acids, which includes proteins, polypeptides, oligopeptides and peptides. The protein may be made up of naturally occurring amino acids and peptide bonds, or synthetic peptidomimetic structures.

By "reduced immunogenicity" herein is meant a decreased ability to activate the immune system, when compared to the parent protein. For example, a protein variant can be said to have "reduced immunogenicity" if it elicits neutralizing or non-neutralizing antibodies in lower titer or in fewer patients than the parent protein. A protein variant also can be said to have "reduced immunogenicity" if it shows decreased binding to one or more MHC alleles or if it induces T cell activation in a decreased fraction of patients relative to the parent protein.

By "residue" as used herein is meant a position in a protein and its associated amino acid identity. For example, serine 31 (also referred to as Ser31, also referred to as S31) is a residue in the WT anti-TAC VH region.

By "scoring function" herein is meant any equation or method for evaluating the fitness of one or more amino acid modifications in a protein. The scoring function may involve a physical or chemical energy term, or may involve knowledge-, statistical-, sequence-based energy terms, and the like.

By "string" as used herein is meant a contiguous sequence that encodes any part of a protein. Strings may comprise any 2 or more linear residues, with the number of contiguous residues being defined by the "window" or "window size". Window sizes of 2-20 are preferred, with 7-13 more preferred, with 9 most preferred.

By "target antigen" as used herein is meant the molecule that is bound specifically by the variable region of a given antibody. A target antigen may be a protein, carbohydrate, lipid, or other chemical compound. An antibody is said to be "specific" for a given target antigen based on having affinity for the target antigen.

By "target cell" as used herein is meant a cell that expresses a target antigen.

By "variable region" as used herein is meant the region of an antibody that comprises one or more Ig domains substantially encoded by any of the VL (including Vκ and Vλ) and/or $V_H$ genes that make up the light chain (including kappa and lambda) and heavy chain immunoglobulin genetic loci respectively. A light or heavy chain variable region (VL and VH) consists of a "framework" or "FR" region interrupted by three hypervariable regions referred to as "complementarity determining regions" or "CDRs". The extent of the framework region and CDRs have been precisely defined, for example as in Kabat (see "Sequences of Proteins of Immunological Interest," E. Kabat et al., U.S. Department of Health and Human Services, (1983)), and as in Chothia. The framework regions of an antibody, that is the combined framework regions of the constituent light and heavy chains, serves to position and align the CDRs, which are primarily responsible for binding to an antigen.

By "variant protein" or "protein variant", or "variant" as used herein is meant a protein that differs from a parent protein by virtue of at least one amino acid modification, including substitutions, insertions and/or deletions. In some cases, variant proteins contain a plurality of amino acid modifications; for example, as described herein, a variant antibody may contain one or more humanized CDRs, and/or a variant that adds or removes a glycosylation or conjugation site (including toxins and polymers such as PEG (including PEG derivatives)), and/or variants that confer altered binding to one or more Fc receptors, including, but not limited to, FcγR1, FcγRIIa, FcγRIIb, FcγRIIIa, FcRn, etc. Protein variant may refer to the protein itself, a composition comprising the protein, or the amino sequence that encodes it. Accordingly, by "immunoglobulin variant" as used herein is meant an immunoglobulin that differs from a parent immunoglobulin by virtue of at least one amino acid modification. Accordingly, by "antibody variant" or "variant antibody" as used herein is meant an antibody that differs from a parent antibody by virtue of at least one amino acid modification. By "CDR variant" herein is meant a CDR that differs from a parent CDR as described herein.

By "wild type or WT" herein is meant an amino acid sequence or a nucleotide sequence that is found in nature and includes allelic variations. A WT protein has an amino acid sequence or a nucleotide sequence that has not been intentionally modified. For example, wild type germline sequences are known and are used as the basis for the humanization of the CDRs as described herein.

Overview

The present invention is directed to the "humanization" of CDR sequences. As is known in the art, there are many therapeutic antibodies that utilize non-human CDRs, particularly murine and particularly mouse CDRs, that are used in conjunction with human framework regions. Alternatively, even "human" antibodies such as produced in transgenic mice may differ from human germine CDR sequences.

The present invention is directed to methods utilizing a starting set of parent CDRs (although as will be appreciated by those in the art, it is also possible to do a single CDR or any combination of CDRs, sequentially or simultaneously) that are non-optimized for "human-ness", and then creating amino acid substitutions based on comparisons with one or more human germline sequences. That is, by making amino acid substitutions in one or more of CDRs that correspond to amino acids in a human germline sequence, the CDR is "humanized" and becomes more "humanlike". In general, this is done separately with the variable light chain (e.g. the 3 light chain CDRs) and the variable heavy chain (e.g. the 3 heavy chain CDRs); that is, the light chain is substituted to be more similar to one germline sequence and the heavy chain is independently substituted to be more similar to another germline sequence, which is most frequently a different germline sequence (although it can be to the same germine sequence). This is referred to herein as "globalized CDR humanization". In addition, this can be done locally, e.g. CDR-by-CDR, with any particular CDR being substituted to be more similar to a first germline sequence, a second to a second, etc. This is called "localized CDR humanization", as described herein.

As is more fully described below, the substitutions may be done one at a time or as multiple variants. Generally a library of variants is created, and then the variants are tested for binding to the target antigen, and variants that retain binding can be combined as well.

As more fully described below, the invention generally relates to variable regions comprising humanized CDRs that are at least about 80-85-90-95% identical to a corresponding human germline CDR sequence, with at least about 85% identity finding particular use, and/or that retain at least about 10-30% of the affinity of the parent CDRs. As noted herein, this identity number is either a global sequence identity, e.g. the three light chain CDRs and the framework region of the light chain, compared to a parent light chain germline sequence and/or the heavy chain CDRs and the framework region of the heavy chain, compared to a parent heavy chain germline sequence.

In addition, these humanized CDRs (whether there is one humanized CDR or more) can be combined with naturally occurring framework regions (including Fc regions), or with variant regions, including variants that confer stability or serum half-life (e.g. FcRn variants) and/or alterations in FcγR binding, as is generally described in US Publication Nos. 2004/0132101, 2005/0054832, 2006/0024298, 2006/0121032, 2006/0235208, 2007/01481702007/0275460, PCT US04/077250, incorporated by reference. In addition, polypeptides comprising the humanized CDRs, such as antibodies, can also be used in combination with engineered glycoform technologies, conjugation technologies (e.g. toxin conjugation), etc.

Antibodies

Antibodies are immunological proteins that bind a specific antigen. In most mammals, including humans and mice, antibodies are constructed from paired heavy and light polypeptide chains. The light and heavy chain variable regions show significant sequence diversity between antibodies, and are responsible for binding the target antigen. Each chain is made up of individual immunoglobulin (Ig) domains, and thus the generic term immunoglobulin is used for such proteins.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. IgA has several subclasses, including but not limited to IgA1 and IgA2. Thus, "isotype" as used herein is meant any of the classes and subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

Each of the light and heavy chains are made up of two distinct regions, referred to as the variable and constant regions. The IgG heavy chain is composed of four immunoglobulin domains linked from N- to C-terminus in the order VH-CH1-CH2-CH3, referring to the heavy chain variable domain, heavy chain constant domain 1, heavy chain constant domain 2, and heavy chain constant domain 3 respectively (also referred to as VH-Cγ1-Cγ2-Cγ3, referring to the heavy chain variable domain, constant gamma 1 domain, constant gamma 2 domain, and constant gamma 3 domain respectively). The IgG light chain is composed of two immunoglobulin domains linked from N- to C-terminus in the order VL-CL, referring to the light chain variable domain and the light chain constant domain respectively. The constant regions show less sequence diversity, and are responsible for binding a number of natural proteins to elicit important biochemical events. The distinguishing features between these antibody classes are their constant regions, although subtler differences may exist in the variable region.

The variable region of an antibody contains the antigen binding determinants of the molecule, and thus determines the specificity of an antibody for its target antigen. The variable region is so named because it is the most distinct in sequence from other antibodies within the same class. The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. There are 6 CDRs total, three each per heavy and light chain, designated VH CDR1, VH CDR2, VH CDR3, VL CDR1, VL CDR2, and VL CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen. Sequence and structural features of antibody variable regions are disclosed, for example, in Morea et al., 1997, Biophys Chem 68:9-16; Morea et al., 2000, Methods 20:267-279, hereby entirely incorporated by reference, and the conserved features of antibodies are disclosed, for example, in Maynard et al., 2000, Annu Rev Biomed Eng 2:339-376, hereby entirely incorporated by reference.

The carboxy-terminal portion of each chain defines a constant region primarily responsible for effector function. In the IgG subclass of immunoglobulins, there are several immunoglobulin domains in the heavy chain. By "immunoglobulin (Ig) domain" herein is meant a region of an immunoglobulin having a distinct tertiary structure. Of interest in embodiments described herein are the heavy chain domains, including, the constant heavy (CH) domains and the hinge region. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH$_3$" refers to positions 341-447 according to the EU index as in Kabat.

The antibodies disclosed herein may be substantially encoded by immunoglobulin genes belonging to any of the antibody classes. In certain embodiments, the antibodies disclosed herein comprise sequences belonging to the IgG class of antibodies, including IgG1, IgG2, IgG3, or IgG4. In alternate embodiments, antibodies disclosed herein comprise sequences belonging to the IgA (including subclasses IgA1 and IgA2), IgD, IgE, IgG, or IgM classes of antibodies.

The parent antibodies of the invention, that is the antibodies from which the antibodies of the invention were derived, may be substantially encoded by genes from any organism, e.g., mammals (including, but not limited to humans, rodents (including but not limited to mice and rats), lagomorpha (including but not limited to rabbits and hares), camelidae (including but not limited to camels, llamas, and dromedaries), and non-human primates, including but not limited to Prosimians, Platyrrhini (New World monkeys), Cercopithecoidea (Old World monkeys), and Hominoidea including the Gibbons and Lesser and Great Apes. In a certain embodiments, the parent antibodies may be substantially human. The parent antibody need not be naturally occurring. For example, the parent antibody may be an engineered antibody, including but not limited to nonhuman and chimeric antibodies. The parent antibody may be an engineered variant of an antibody that is substantially encoded by one or more natural antibody genes. In one embodiment, the parent antibody has been affinity matured, as is known in the art, or engineered in some other way, such as to alter FcR binding, for example. In some embodiments, the parent antibody is a humanized antibody, containing non-human (e.g. murine) CDRs with the remainder of the molecule comprising human sequences. In some embodiments, the parent antibody has had its framework regions optimized, with non-human CDRs.

The antibodies of the present invention may comprise sequences belonging to the IgG (including IgG1, IgG2, IgG3, IgG4 and fusions of any combination), IgA (including subclasses IgA1 and IgA2), IgD, IgE, IgG, IgM (and fusions of any combination) classes of antibodies, with the IgG class being preferred. The less immunogenic antibodies of the present invention may be full length antibodies, or antibody fragments. Constant regions need not be present, but if they are, they will likely be substantially identical to human immunoglobulin constant regions.

As is well known in the art, antibody polymorphisms exist in the human population. Gm polymorphism is determined by the IGHG1, IGHG2 and IGHG3 genes which have alleles encoding allotypic antigenic determinants referred to as G1m, G2m, and G3m allotypes for markers of the human IgG1, IgG2 and IgG3 molecules (no Gm allotypes have been found on the gamma 4 chain). Markers may be classified into 'allotypes' and 'isoallotypes'. These are distinguished on different serological bases dependent upon the strong sequence homologies between isotypes. Allotypes are antigenic determinants specified by allelic forms of the Ig genes. Allotypes represent slight differences in the amino acid sequences of heavy or light chains of different individuals. Even a single amino acid difference can give rise to an allotypic determinant, although in many cases there are several amino acid substitutions that have occurred. Allotypes are sequence differences between alleles of a subclass whereby the antisera recognize only the allelic differences. An isoallotype is an allele in one isotype which produces an epitope which is shared with a non-polymorphic homologous region of one or more other isotypes and because of this the antisera will react with both the relevant allotypes and the relevant homologous isotypes (Clark, 1997, IgG effector mechanisms, Chem Immunol. 65:88-110; Gorman & Clark, 1990, Semin Immunol 2(6):457-66, both hereby entirely incorporated by reference).

Allelic forms of human antibodies have been well-characterized (WHO Review of the notation for the allotypic and related markers of human immunoglobulins. J Immunogen 1976, 3: 357-362; WHO Review of the notation for the allotypic and related markers of human immunoglobulins. 1976, Eur. J. Immunol. 6, 599-601; Loghem E van, 1986, Allotypic markers, Monogr Allergy 19: 40-51, all hereby entirely incorporated by reference). Additionally, other polymorphisms have been characterized (Kim et al., 2001, J. Mol. Evol. 54:1-9, hereby entirely incorporated by reference). At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-211, both hereby entirely incorporated by reference). Allotypes that are inherited in fixed combinations are called Gm haplotypes. The antibodies disclosed herein may be substantially encoded by any allotype, isoallotype, or haplotype of any immunoglobulin gene.

The variable region of an antibody, as is well known in the art, can compose sequences from a variety of species. In some embodiments, the antibody variable region can be from a nonhuman source, including but not limited to mice, rats, rabbits, camels, llamas, and monkeys. In some embodiments, the scaffold components can be a mixture from different species. As such, an antibody disclosed herein may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse or other nonhuman species and the constant region(s) from a human.

"Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. "Backmutation" of selected acceptor framework residues to the corresponding donor residues is often required to regain affinity that is lost in the initial grafted construct (U.S. Pat. No. 5,693,762, incorporated entirely by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization or other methods of reducing the immunogenicity of nonhuman antibody variable regions may include resurfacing methods, as described for example in Roguska et al., 1994, Proc. Natl. Acad. Sci. USA 91:969-973. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, that is, to increase the affinity of the variable region for its target antigen. Other humanization methods may involve the grafting of only parts of the CDRs, including but not limited to methods described in U.S. Ser. No. 09/810,502; Tan et al., 2002, J. Immunol. 169:1119-1125; De Pascalis et al., 2002, J. Immunol. 169:3076-3084. Structure-based methods may be employed for humanization and affinity maturation, for example as described in U.S. Ser. No. 10/153,159 and related applications, all incorporated entirely by reference. In certain variations, the immunogenicity of the antibody is reduced using a method described in U.S. Ser. No. 11/004,590, entitled "Methods of Generating Variant Proteins with Increased Host String Content and Compositions Thereof", filed on Dec. 3, 2004, incorporated entirely by reference.

The engineered antibodies of the invention are human equivalent antibodies. Historically, fully human antibodies have been obtained using transgenic mice (Bruggemann et al., 1997, Curr Opin Biotechnol 8:455-458) or human antibody libraries coupled with selection methods (Griffiths et al., 1998, Curr Opin Biotechnol 9:102-108). However, the present invention describes a novel method for engineering human equivalent antibodies from nonhuman parent antibodies. For the purposes of the present invention, "a humanlike antibody" or "human equivalent antibody" is defined as: an antibody whose variable heavy and light chains have sequences that are greater than about 85% identical to at least one sequence in a human germline immunoglobulin gene sequence; an antibody whose individual CDRs have greater than about 50-60-70-80-90% identity to at least one CDR of a human germline sequence (with greater than about 80% finding use in a number of applications); or sequences that have greater than 52% of their 9-mers that are a perfect match with at least one 9-mer in a human germline immunoglobulin gene sequence.

Engineering of Human Equivalent Antibodies

Current engineering methods for reducing the immunogenicity of antibodies (e.g. humanization) with non-human variable regions do not succeed in creating antibodies with global sequence identity levels comparable to human antibodies. The principal reason for this is that none of the current methods substantially engineer the CDRs due to the perceived risk of losing antigen affinity. Methods that have ventured into the CDRs, such as SDR-grafting (Kashmiri, et al., 2005, *Methods* 36:25-34; Gonzales, et al., 2004, *Mol Immunol* 41:863-872), have either failed to change the CDRs significantly enough to yield human equivalent levels of global sequence identity or have resulted in variants having a significant decrease in affinity. The present invention is based on the discovery that with precise engineering of the antibody variable region, including the CDRs, it is possible to engineer an antibody with a non-human variable region to have humanness or "human equivalent" levels comparable to fully-human antibodies, and importantly, to maintain antigen affinity to within 3-fold of the of the parent antibody. The method (outlined in FIG. 1) consists of five main steps: (1) the optional generation of a framework-optimized template sequence; (2) identification of the closest matching human germline sequence for the (optionally) framework-optimized $V_H$ and $V_L$; (3) generation and screening of a variant library consisting of all possible single mutations designed to increase the local and/or global sequence identity of the framework-optimized sequence to the closest human germline sequence while maintaining antigen affinity; (4) generation and screening of variants consisting of combinations of neutral or affinity enhancing single mutations for $V_H$ and $V_L$; and (5) expression and screening of the highest affinity $V_H$ and $V_L$ chains paired together to generate the final human equivalent mAb. In other embodiments, the framework sequences need not be optimized. In other embodiments, either with or without framework optimization, the variant library can contain less than every possible single mutation and/or double or higher numbers of mutations as well.

When framework optimization is done, the method proceeds as follows. After selection of the non-human parent Fv, the first step in the process is to engineer the framework regions for high human sequence content. This framework-optimized mAb is engineered using a method such as that described in U.S. Ser. No. 11/004,590, entitled "Methods of Generating Variant Proteins with Increased Host String Content and Compositions Thereof", filed on Dec. 6, 2004, incorporated herein by reference in it's entirety, and in particular for the methods of framework optimization. Other methods of reducing potential immunogenicity using antibody engineering, such as CDR-grafting (Jones, et al., 1986, *Nature* 321: 522-525), resurfacing (Roguska, et al., 1994, *Proc Natl Acad Sci USA* 91:969-973; Roguska, et al., 1996, *Protein Eng* 9:895-904), SDR-grafting (Kashmiri, et al., 2005, *Methods* 36:25-34; Gonzales, et al., 2004, *Mol Immunol* 41:863-872), superhumanization (Hwang, et al., 2005, *Methods* 36:35-42), and framework shuffling (Dall'Acqua, et al., 2005, *Methods* 36:43-60; Damschroder, et al., 2007, *Mol Immunol* 44:3049-3060) may be used, provided the final framework-optimized mAb has high human sequence content in the framework regions and the antibody maintains antigen affinity equivalent to the original mAb with non-human Fv.

Following the optional creation of the framework-optimized mAb, the next step in the engineering process is to analyze the sequence of this mAb (or, in the case where no framework optimization occurs, against the starting parent sequence) against the human germline repertoire. The set of human sequences used is an aligned set of human germline immunoglobulin sequences. The human germline repertoire for immunoglobulin heavy chain variable regions and immunoglobulin light chain kappa variable regions has been reported (Matsuda et al., 1998, *J Exp Med* 188: 2151-2162; Zachau, 2000, Biol Chem 381:951-954; Pallares et al., 1999, *Exp Clin Immunogenet* 16(1): 36-60; Barbie & Lefranc, 1998, *Exp Clin Immunogenet* 15(3): 171-83). For many of the genes in the human immunoglobulin germline, several different alleles have been identified. Although the polymorphisms detected in many of the alleles do not change the amino acid sequence of the gene, in a great number of cases the sequence is changed. In choosing a set of sequences to use in the method described herein, different sets of sequences may be chosen. In general, the set may be a single sequence with the best starting identity to the parent sequence, a number of sequences, etc.

The framework-optimized heavy and light chains are aligned with the human germline V- and J-segments and the germlines ranked based on the number of mutations away from the framework-optimized sequence, the conservativeness of each mutation, and/or the proximity of each mutation to CDRs. That is, in some embodiments, the germline is chosen based on the absolute smallest number of mutations between the germline and the parent molecule, or based on the smallest number of mutations within the set of CDRs or within single CDRs. Similarly, the germline with the highest identity may have non-conservative mutations (based on a BLOSUM matrix, for example), with germlines with lower identity having higher conservativeness, with the latter being a good choice in some cases. Similarly, the distance of the mutations to the CDRs may be important: for example, if one germline has a framework with 30 differences, 20 of them located at a distance from each CDR and 10 close, and another germline has 30 differences but 20 are close and 10 are farther, it may be desirable in some situations to pick the former.

By using these criteria to select the germline to engineer the parent antibody towards, the probability of achieving a human equivalent mAb with a minimal loss in antigen affinity is increased. Variants with single mutations representing each of the differences in sequence between the framework-optimized mAb and the closest germline V- and J-segments are constructed and screened using standard techniques. For instance, if the framework-optimized mAb had a serine at position 31 in the heavy chain, but the closest germline had a tyrosine at position 31, then a variant of the framework-optimized mAb with tyrosine at position 31 would be constructed and screened for antigen binding. This procedure is performed for all such differences in the two sequences and the data tabulated. Most mutations will be in the CDRs, but a few may be in framework regions that are known to be proximal to the CDRs or located in the VH/VL interface.

In the next step, single mutations that resulted in comparable affinity to the framework-optimized Fv are explored in combination. Combinations of heavy chain variants are paired with the framework-optimized light chain and combinations of light chain variants are paired with the framework-optimized heavy chain. Because the additivity of single variants is difficult to predict, it is important to try several possible combinations of variants that have different levels of diversity and human sequence content. However, depending on the number of single variants, the number of possible combination variants can be large. Thus, an approach to limit the number of combination variants by balancing human sequence content and diversity of the library can be useful. A computational approach to designing such diverse libraries, such as Combination Design Automation or CDA™ technology is one such method that can be used. Expression and screening of the combination variant library will result in several variants with either human equivalent heavy or light chains with antigen affinity comparable to the framework-optimized mAb. In vitro and/or in vivo assays are used to evaluate the efficacy and potency of the engineered human equivalent antibodies.

Evaluation of Humanness

"Humanness" or "humanlike" or "human equivalent" evaluations can be done in a variety of ways. In one embodiment, global identity scores are used. Global identity is the number of exact sequence matches between the engineered sequence and any one of the human germline $V_H$, $V_K$, $J_H$, and $J_K$ segments (the D segment for the heavy chain is not included). An additional score can be based just on the CDR identities, rather than the entire germline. A further possible score is the number of total "human 9-mers", which is an exact count of 9-mer stretches in the engineered sequence that perfectly match any one of the corresponding stretches of nine amino acids in our set of functional human germline sequences. Finally, the variant antibody can be evaluated on the basis of actual immunogenicity in a host organism as compared to the parent antibody.

As shown in FIG. 11 and FIG. 12, antibodies with murine variable regions (murine and chimeric antibodies) typically have global identities less than 71% and less than 13% human 9-mers. Human equivalent antibodies typically have global identities between about 78% and about 85% (with from about 60, 65, 70, 75, 80, 85, 90 and 95% possible, with all possible combination of ranges) and human 9-mers of between about 32% and about 52% (with from about 30, 35, 40, 45, 50, 55, 60, 65 and 70% possible, with all possible combination of ranges). Fully-human antibodies isolated from human antibody libraries or from transgenic mice comprising human germline immunoglobulin gene sequences typically have global identities greater than 85% and human 9-mers greater than 52%.

Target Antigens

Virtually any binding partner or antigen may be targeted by the antibodies of the present invention. A number biotherapeutic proteins and antibodies that are approved for use, in clinical trials, or in development may thus benefit from the methods of the present invention.

Other Antibody Modifications

The antibodies of the invention may be modified in some way to make them more effective, particularly more effective as therapeutics. A variety of modifications for improving the properties of antibodies are described U.S. Ser. No. 10/672,280; U.S. Ser. No. 10/822,231; U.S. Ser. No. 11/124,620; U.S. Ser. No. 11/396,495; U.S. Ser. No. 11/538,406; U.S. Ser. No. 12/020,443; U.S. Ser. No. 12/156,183; U.S. Ser. No. 11/274,065; U.S. Ser. No. 11/436,266; U.S. Ser. No. 11/932,151; U.S. Ser. No. 12/341,769; Hinton et al., 2004, J. Biol. Chem. 279(8): 6213-6216, Hinton et al. 2006 Journal of Immunology 176:346-356, U.S. Ser. No. 11/102,621; U.S. Ser. No. 10/966,673; Shields et al, Journal of Biological Chemistry, 2001, 276(9):6591-6604; U.S. Ser. No. 11/429,793; Dall Acqua et al. Journal of Immunology, 2002, 169: 5171-5180; U.S. Pat. No. 7,083,784; PCT/US2004/037929; Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; Yamane-Ohnuki et al., 2004, Biotechnol Bioeng 87 (5), 614-622; Li et al., 2006, Nature Biotechnology 24(2):210-215; Nechansky et al., 2007, Mol Immunjol 44(7):1826-8; Cox et al., 2006, Nat Biotechnol 24(12): 1591-7; and Kaneko et al., 2006, Science 313:670-673, all expressly incorporated by reference.

Modifications may include amino acid modifications, glycoform modifications, and chemical modifications. Modifications may improve the antibody's effector function properties, pharmacokinetic properties, solution properties, and/or biological activity. The antibodies of the invention may be conjugated or operably linked to another therapeutic compound. The therapeutic compound may be a cytotoxic agent, a chemotherapeutic agent, a toxin, a radioisotope, a cytokine, or other therapeutically active agent. The antibodies of the invention may be conjugated to a protein or molecule for utilization in tumor pretargeting or prodrug therapy. Other modifications of the antibodies are contemplated herein. For example, the antibody may be linked to one of a variety of nonproteinaceous polymers, for example e.g., polyethylene glycol (PEG).

Production of Antibodies

Also disclosed herein are methods for producing and experimentally testing antibodies. The disclosed methods are not meant to constrain embodiments to any particular application or theory of operation. Rather, the provided methods are meant to illustrate generally that one or more antibodies may be produced and experimentally tested to obtain antibodies. General methods for antibody molecular biology, expression, purification, and screening are described in Antibody Engineering, edited by Duebel & Kontermann, Springer-Verlag, Heidelberg, 2001; and Hayhurst & Georgiou, 2001, Curr Opin Chem Biol 5:683-689; Maynard & Georgiou, 2000, Annu Rev Biomed Eng 2:339-76; Antibodies: A Laboratory Manual by Harlow & Lane, New York: Cold Spring Harbor Laboratory Press, 1988, all incorporated entirely by reference.

In one embodiment disclosed herein, nucleic acids are created that encode the antibodies, and that may then be cloned into host cells, expressed and assayed, if desired. Thus, nucleic acids, and particularly DNA, may be made that encode each protein sequence. These practices are carried out using well-known procedures. For example, a variety of methods that may find use in generating antibodies disclosed herein are described in Molecular Cloning—A Laboratory Manual, 3$^{rd}$ Ed. (Maniatis, Cold Spring Harbor Laboratory Press, New York, 2001), and Current Protocols in Molecular Biology (John Wiley & Sons), both incorporated entirely by reference. As will be appreciated by those skilled in the art, the generation of exact sequences for a library comprising a large number of sequences is potentially expensive and time consuming. By "library" herein is meant a set of variants in any form, including but not limited to a list of nucleic acid or amino acid sequences, a list of nucleic acid or amino acid substitutions at variable positions, a physical library comprising nucleic acids that encode the library sequences, or a physical library comprising the variant proteins, either in purified or unpurified form. Accordingly, there are a variety of techniques that may be used to efficiently generate libraries disclosed herein. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in for generating nucleic acids that encode antibodies.

The antibodies disclosed herein may be produced by culturing a host cell transformed with nucleic acid, e.g., an expression vector, containing nucleic acid encoding the antibodies, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, and yeast. For example, a variety of cell lines that may find use in generating antibodies disclosed herein are described in the ATCC® cell line catalog, available from the American Type Culture Collection.

In one embodiment, the antibodies are expressed in mammalian expression systems, including systems in which the expression constructs are introduced into the mammalian cells using virus such as retrovirus or adenovirus. Any mammalian cells may be used, e.g., human, mouse, rat, hamster, and primate cells. Suitable cells also include known research cells, including but not limited to Jurkat T cells, NIH3T3, CHO, BHK, COS, HEK293, PER C.6, HeLa, Sp2/0, NS0 cells and variants thereof. In an alternate embodiment, library proteins are expressed in bacterial cells. Bacterial expression systems are well known in the art, and include *Escherichia coli* (*E. coli*), *Bacillus subtilis, Streptococcus cremoris,* and *Streptococcus lividans*. In alternate embodiments, antibodies are produced in insect cells (e.g. Sf21/Sf9, *Trichoplusia ni* Bti-Tn5b1-4) or yeast cells (e.g. *S. cerevisiae, Pichia,* etc). In an alternate embodiment, antibodies are expressed in vitro using cell free translation systems. In vitro translation systems derived from both prokaryotic (e.g. *E. coli*) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the antibodies may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode the antibodies disclosed herein may be incorporated into an expression vector in order to express the protein. A variety of expression vectors may be utilized for protein expression. Expression vectors may comprise self-replicating extrachromosomal vectors or vectors which integrate into a host genome. Expression vectors are constructed to be compatible with the host cell type. Thus expression vectors which find use in generating antibodies disclosed herein include but are not limited to those which enable protein expression in mammalian cells, bacteria, insect cells, yeast, and in in vitro systems. As is known in the art, a variety of expression vectors are available, commercially or otherwise, that may find use for expressing antibodies disclosed herein.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the antibody, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

Antibodies may be operably linked to a fusion partner to enable targeting of the expressed protein, purification, screening, display, and the like. Fusion partners may be linked to the antibody sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS. A fusion partner may be a targeting or signal sequence that directs antibody and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example $H_6$ and $H_{10}$ or other tags for use with Immobilized Metal Affinity Chromatography (IMAC) systems (e.g. $Ni^{+2}$ affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an antibody may be purified using a His-tag by immobilizing it to a $Ni^{+2}$ affinity column, and then after purification the same His-tag may be used to immobilize the antibody to a $Ni^{+2}$ coated plate to perform an ELISA or other binding assay (as described below). A fusion partner may enable the use of a selection method to screen antibodies (see below). Fusion partners that enable a variety of selection methods are well-known in the art. For example, by fusing the members of an antibody library to the gene III protein, phage display can be employed (Kay et al., Phage display of peptides and proteins: a laboratory manual, Academic Press, San Diego, Calif., 1996; Lowman et al., 1991, *Biochemistry* 30:10832-10838; Smith, 1985, *Science* 228:1315-1317, incorporated entirely by reference). Fusion partners may enable antibodies to be labeled. Alternatively, a fusion partner may bind to a specific sequence on the expression vector, enabling the fusion partner and associated antibody to be linked covalently or noncovalently with the nucleic acid that encodes them. The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In one embodiment, antibodies are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use for purification of antibodies disclosed herein. For example, the bacterial proteins A and G bind to the Fc region. Likewise, the bacterial protein L binds to the Fab region of some antibodies, as of course does the antibody's target antigen. Purification can often be enabled by a particular fusion partner. For example, antibodies may be purified using glutathione resin if a GST fusion is employed, $Ni^{+2}$ affinity chromatography if a His-tag is employed, or immobilized anti-flag antibody if a flag-tag is used. For general guidance in suitable purification techniques, see, e.g. incorporated entirely by reference Protein Purification: Principles and Practice, $3^{rd}$ Ed., Scopes, Springer-Verlag, NY, 1994, incorporated entirely by reference. The degree of purification necessary will vary depending on the screen or use of the antibodies. In some instances no purification is necessary. For example in one embodiment, if the antibodies are secreted, screening may take place directly from the media. As is well known in the art, some methods of selection do not involve purification of proteins. Thus, for example, if a library of antibodies is made into a phage display library, protein purification may not be performed.

In Vitro Experimentation

Antibodies may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label. The use of fusion partners has been discussed above. By "labeled" herein is meant that the antibodies disclosed herein have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c)

small molecule labels, which may include fluorescent and colorimetric dyes, or molecules such as biotin that enable other labeling methods. Labels may be incorporated into the compound at any position and may be incorporated in vitro or in vivo during protein expression.

In one embodiment, the functional and/or biophysical properties of antibodies are screened in an in vitro assay. In vitro assays may allow a broad dynamic range for screening properties of interest. Properties of antibodies that may be screened include but are not limited to antigen binding (e.g. affinity for the target antigen), stability, solubility, and affinity for Fc ligands, for example FcγRs. Multiple properties may be screened simultaneously or individually. Proteins may be purified or unpurified, depending on the requirements of the assay. In one embodiment, the screen is a qualitative or quantitative binding assay for binding of antibodies to a protein or nonprotein molecule that is known or thought to bind the antibody. In one embodiment, the screen is a binding assay for measuring binding to the target antigen. In an alternate embodiment, the screen is an assay for binding of antibodies to an Fc ligand, including but are not limited to the family of FcγRs, the neonatal receptor FcRn, the complement protein C1q, and the bacterial proteins A and G. Said Fc ligands may be from any organism. In one embodiment, Fc ligands are from humans, mice, rats, rabbits, and/or monkeys. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label of the antibody. Assays may employ a variety of detection methods including but not limited to chromogenic, fluorescent, luminescent, or isotopic labels.

The biophysical properties of antibodies, for example stability and solubility, may be screened using a variety of methods known in the art. Protein stability may be determined by measuring the thermodynamic equilibrium between folded and unfolded states. For example, antibodies disclosed herein may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an antibody may be quantitatively or qualitatively determined using a wide range of methods that are known in the art. Methods which may find use for characterizing the biophysical properties of antibodies disclosed herein include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an antibody could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the antibody's stability and solubility.

In one embodiment, the library is screened using one or more cell-based or in vitro assays. For such assays, antibodies, purified or unpurified, are typically added exogenously such that cells are exposed to individual variants or groups of variants belonging to a library. These assays are typically, but not always, based on the biology of the ability of the antibody to bind to the target antigen and mediate some biochemical event, for example effector functions like cellular lysis, phagocytosis, ligand/receptor binding inhibition, inhibition of growth and/or proliferation, apoptosis and the like. Such assays often involve monitoring the response of cells to antibody, for example cell survival, cell death, cellular phagocytosis, cell lysis, change in cellular morphology, or transcriptional activation such as cellular expression of a natural gene or reporter gene. For example, such assays may measure the ability of antibodies to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, e.g., humans, mice, rat, rabbit, and monkey. Crosslinked or monomeric antibodies may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flourconjugates may enable apoptosis to be measured, and uptake or release of radioactive substrates (e.g. Chromium-51 release assays) or the metabolic reduction of fluorescent dyes such as alamar blue may enable cell growth, proliferation or activation to be monitored. In one embodiment, the DELFIA® EuTDA-based cytotoxicity assay (Perkin Elmer, MA) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an antibody. Cell types for such assays may be prokaryotic or eukaryotic, and a variety of cell lines that are known in the art may be employed. Alternatively, cell-based screens are performed using cells that have been transformed or transfected with nucleic acids encoding the antibodies.

In vitro assays include but are not limited to binding assays, ADCC, CDC, cytotoxicity, proliferation, peroxide/ozone release, chemotaxis of effector cells, inhibition of such assays by reduced effector function antibodies; ranges of activities such as >100× improvement or >100× reduction, blends of receptor activation and the assay outcomes that are expected from such receptor profiles.

In Vivo Experimentation

The biological properties of the antibodies disclosed herein may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. Said animals may be referred to as disease models. In some embodiments, antibodies disclosed herein may be assessed for efficacy in clinically relevant animal models of various human diseases. In many cases, relevant models include various transgenic animals for specific antigens and receptors.

Other organisms, e.g., mammals, may also be used for testing. For example, because of their genetic similarity to humans, monkeys can be suitable therapeutic models, and thus may be used to test the efficacy, toxicity, pharmacokinetics, or other property of the antibodies disclosed herein. In one embodiment, the testing of antibodies may include study of efficacy in primates (e.g. cynomolgus monkey model) to facilitate the evaluation of depletion of specific target cells harboring the target antigen. Additional primate models include but are not limited to use of the rhesus monkey to assess Fc polypeptides in therapeutic studies of autoimmune, transplantation and cancer. Toxicity studies are performed to determine antibody related-effects that cannot be evaluated in standard pharmacology profiles, or occur only after repeated administration of the agent. The pharmacokinetics (PK) of the antibodies disclosed herein may be studied in a variety of animal systems, with the most relevant being non-human primates such as the cynomolgus and rhesus monkeys.

Tests of the antibodies disclosed herein in humans are ultimately required for approval as drugs, and thus of course these experiments are contemplated. Thus the antibodies disclosed herein may be tested in humans to determine their therapeutic efficacy, toxicity, pharmacokinetics, and/or other clinical properties.

Therapeutic Application

The antibodies of the invention may find use in a wide range of protein products. In one embodiment the antibody is a therapeutic, a diagnostic, or a research reagent, preferably a therapeutic. Alternatively, the antibody of the invention may be used for agricultural or industrial uses. In a preferred embodiment, the protein is a therapeutic that is used to treat a disease. By "disease" herein is meant a disorder that may be ameliorated by the administration of a pharmaceutical composition comprising a protein of the present invention. Diseases include but are not limited to autoimmune diseases, immunological diseases, infectious diseases, inflammatory diseases, neurological diseases, and oncological and neoplastic diseases including cancer. In one embodiment, an antibody of the invention is the only therapeutically active agent administered to a patient. Alternatively, the antibody of the invention is administered in combination with one or more other therapeutic agents, including but not limited to cytotoxic agents, chemotherapeutic agents, cytokines, growth inhibitory agents, anti-hormonal agents, kinase inhibitors, anti-angiogenic agents, cardioprotectants, or other therapeutic agents. The antibodies of the invention may be combined with other therapeutic regimens. For example, in one embodiment, the patient to be treated with the protein may also receive radiation therapy and/or undergo surgery.

A "patient" for the purposes disclosed herein includes both humans and other animals, e.g., other mammals. Thus the immunoglobulins disclosed herein have both human therapy and veterinary applications. The term "treatment" or "treating" as disclosed herein is meant to include therapeutic treatment, as well as prophylactic, or suppressive measures for a disease or disorder. Thus, for example, successful administration of an immunoglobulin prior to onset of the disease results in treatment of the disease. As another example, successful administration of an optimized immunoglobulin after clinical manifestation of the disease to combat the symptoms of the disease comprises treatment of the disease. "Treatment" and "treating" also encompasses administration of an optimized immunoglobulin after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

Pharmaceutical compositions are contemplated wherein an antibody of the invention and one or more therapeutically active agents are formulated. The antibodies may find use in a composition that is monoclonal or polyclonal. Formulations are prepared for storage by mixing the protein having the desired degree of purity with optional pharmaceutically acceptable carriers, excipients or stabilizers (Remington's Pharmaceutical Sciences 16th edition, Osol, A. Ed., 1980), in the form of lyophilized formulations or aqueous solutions. The formulations to be used for in vivo administration are preferably sterile. The antibodies disclosed herein may also be formulated as immunoliposomes, or entrapped in microcapsules. The concentration of the protein of the present invention in the formulation may vary from about 0.1 to 100 weight %. In a preferred embodiment, the concentration of the protein is in the range of 0.003 to 1.0 molar. In order to treat a patient, a therapeutically effective dose of the protein of the present invention may be administered. The exact dose will depend on the purpose of the treatment, and will be ascertainable by one skilled in the art using known techniques. Dosages may range from 0.01 to 100 mg/kg of body weight or greater, for example 0.1, 1, 10, or 50 mg/kg of body weight, with 1 to 10 mg/kg being preferred. Administration of the pharmaceutical composition comprising an antibody of the invention, preferably in the form of a sterile aqueous solution, may be done in a variety of ways, including, but not limited to, orally, subcutaneously, intravenously, intranasally, intraotically, transdermally, topically, intraperitoneally, intramuscularly, intrapulmonary, inhalably, vaginally, parenterally, rectally, or intraocularly. As is known in the art, the pharmaceutical composition may be formulated accordingly depending upon the manner of introduction.

EXAMPLES

Examples are provided below to illustrate the present invention. These examples are not meant to constrain the present invention to any particular application or theory of operation.

Example 1

Engineering of a Human Equivalent Anti-CD25 Monoclonal Antibody

An outline of the process of engineering a human equivalent anti-CD25 mAb from a murine anti-CD25 Fv is shown in FIG. 1. The murine anti-CD25 mAb anti-TAC (Uchiyama, et al., 1981, *J Immunol* 126:1393-1397) was chosen as a starting point for engineering of a high affinity human equivalent anti-CD25 mAb. This mAb is the precursor of daclizumab, a humanized and marketed anti-CD25 mAb used for prevention of rejection in organ transplantation. Even though this mAb was humanized by CDR-grafting (Queen, et al., 1989, *Proc Natl Acad Sci USA* 86:10029-10033), approximately 14% of adults and 34% of pediatric patients receiving this drug develop a low-level immune response (Roche, 2005, Zenapax prescribing information), thus engineering a human equivalent mAb from the murine anti-TAC variable region seemed like an excellent test case for our methodology. The murine anti-TAC Fv was engineered into a "framework optimized" anti-CD25 mAb (anti-CD25 H1L1) by reducing the immunogenicity of the variable region using a method described in U.S. Ser. No. 11/004,590, entitled "Methods of Generating Variant Proteins with Increased Host String Content and Compositions Thereof", filed on Dec. 6, 2004. This method utilizes the homology present in human germline sequences and essentially makes murine to human mutations in order to increase the human string content of the Fv. Positions that are not within or proximal to the CDRs and $V_H/V_L$ interface are optimized in this step, and the relative humanness of the resulting Fv is comparable to mAbs humanized using CDR-grafting and other humanization techniques. Framework optimized heavy chain H1 and light chain L1 were constructed by gene synthesis, and IgG1 format antibodies were expressed transiently in 293E cells, purified by Protein A chromatography, and evaluated by SDS-PAGE and SEC. Antigen affinity of anti-CD25 H1L1 was compared to that of chimeric anti-CD25 H0L0 by Biacore.

For kinetic analysis of anti-CD25 antibodies, Protein A was coupled to an activated CM5 biosensor chip and 10-25 nM of anti-CD25 antibody injected at a flow rate of 5-10 μL/min for 1 min. Binding was measured by injection of two-fold serial dilutions of CD25 (0 nM to 50 nM; R&D systems) in buffer at 25° C. with a flow rate of 25-30 μL/min for 2 min followed by a dissociation phase of 4-5 min. Association rates ($k_{on}$) and dissociation rates ($k_{off}$) were calculated using a simple one-to-one Langmuir binding model (BIAcore Evaluation Software version 3.2). The equilibrium dissociation constant ($K_d$) was calculated as the ratio of $k_{off}/k_{on}$). $K_d$ values ranged from 0.3-1.1 nM for anti-CD25 H1L1 and 0.09-0.3 nM for anti-CD25 H0L0, and data from four separate Biacore runs consistently showed that anti-CD25 H1L1 has ~3.5-fold reduced affinity compared to anti-CD25 H0L0 even though absolute $K_d$ values varied somewhat between the separate runs.

Figure 2:
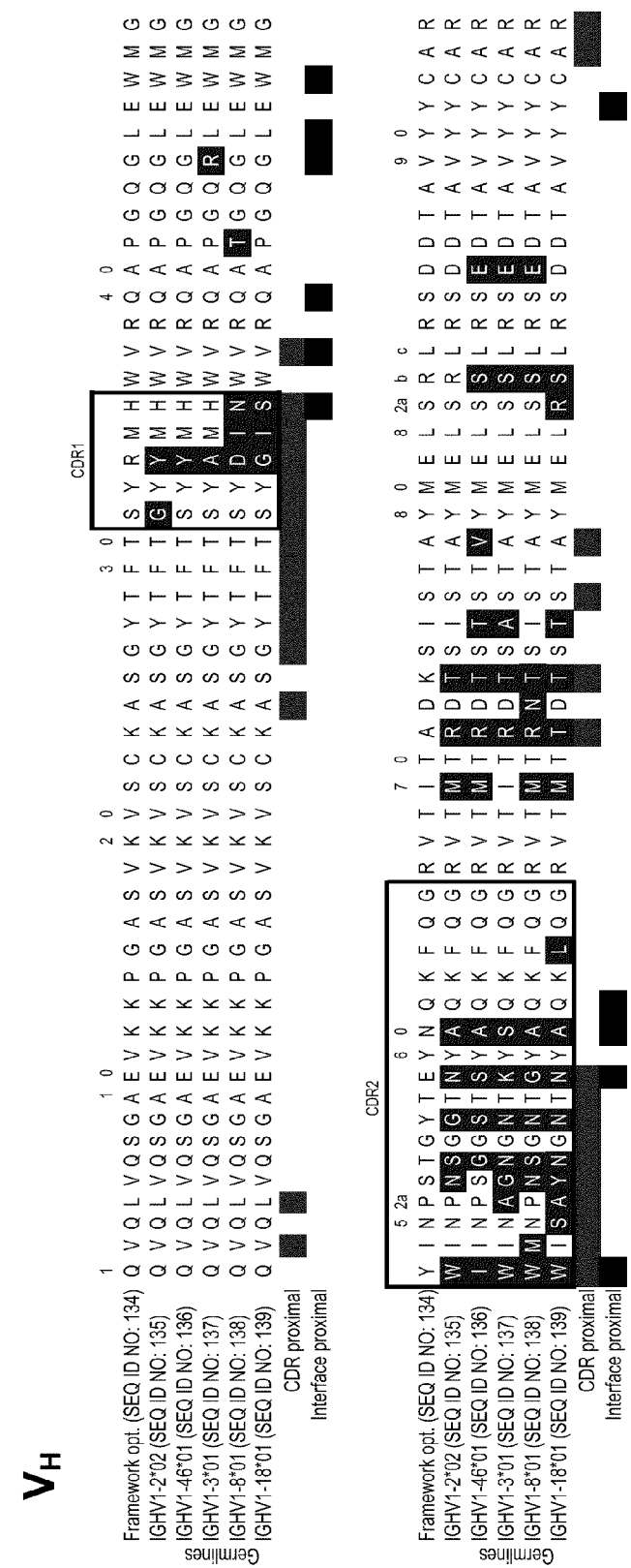
FIG. 2. (SEQ ID NO: 134-145) Comparison of the V-segment ($V_H$ and $V_L$) and J-segment ($V_L$) of an initial framework optimized anti-CD25 variable region sequence to the five closest matching human germline V- and J-segments. Sequences are numbered according to Kabat et. al., and CDR regions are outlined Amino acids in the human germline V-regions that differ from the framework optimized sequence are highlighted. Positions that are in CDRs or CDR proximal and/or proximal to the $V_H/V_L$ interface are indicated. For $V_L$, amino acids in common among all five J-regions are shown and those positions that differ are listed as X's.
Figure 2:
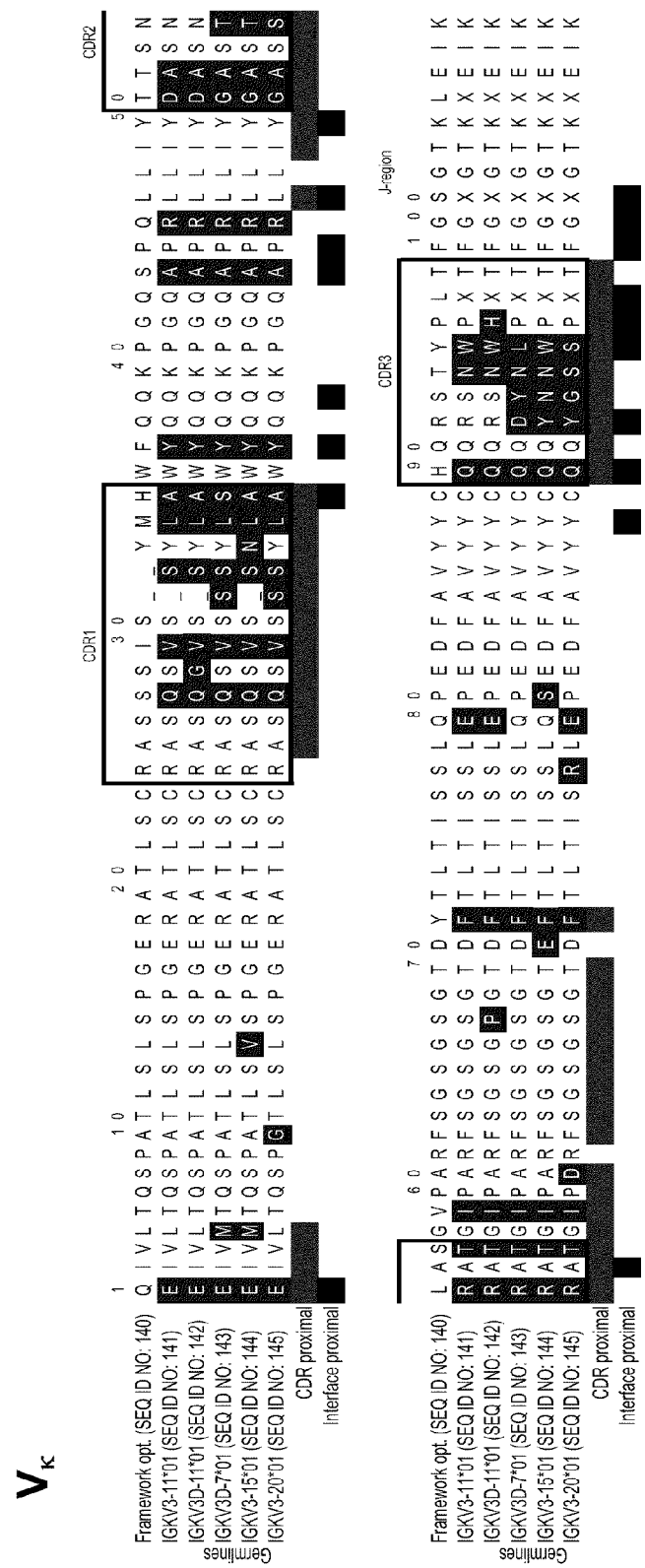

The framework optimized anti-CD25 heavy and light chains (H1 and L1, respectively) were aligned with the human germline V- and J-segments and the germlines were ranked based on the number of mutations away from the framework optimized sequence, the conservativeness of each mutation, and the proximity of each mutation to CDRs (FIG. 2). For $V_H$, the five highest ranking human germlines were IGHV1-2*02, IGHV1-46*01, IGHV1-3*01, IGHV1-8*01, and IGHV1-18*01, respectively. These germlines had 11, 13, 14, 17, and 18 differences from anti-CD25 H1, respectively. For VL, the five highest ranking human germlines were IGKV3-11*01, IGKV3D-11*01, IGKV3D-7*01, IGKV3-15*01, and IGKV3-20*01, with 19, 22, 23, 26, and 26 differences from anti-CD25 L1, respectively.

Figure 3:
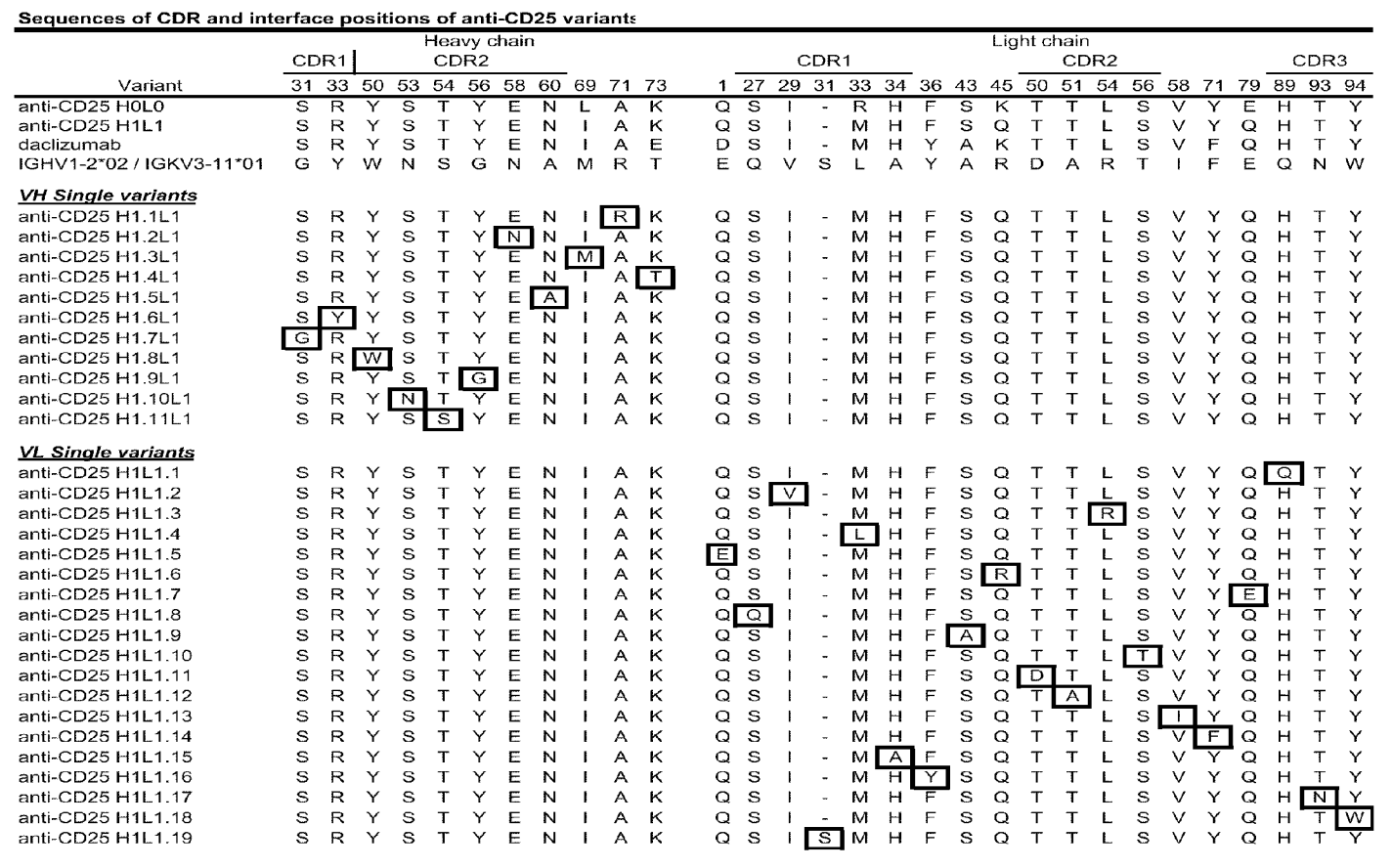

The highest ranking $V_H$ germline IGHV1-2*02 and $V_L$ germline IGKV3-11*01 were chosen as the basis for further engineering. Single variants were constructed in the anti-CD25 H1L1 background and expressed, purified, and assayed as mentioned above in order to assess the impact of the 11 differences between anti-CD25 H1 and IGHV1-2*02, and the 19 differences between anti-CD25 L1 and IGKV3-11*01. The single variants constructed are shown in FIG. 3 along with binding data and humanness scores (number of human 9-mers and number of identities (IDs) to the closest matching human germlines) for each variant. Variants that had $K_d$ values no worse than 1.5-fold weaker from that of anti-CD25 H1L1 were selected to be combined in the next round of engineering. Surprisingly, the majority of variants had increased or retained affinity. For $V_H$, ten out of eleven variants had neutral or higher affinity, with the only exception being R33Y in CDR1 which showed a decreased affinity of 5.6-fold. Three $V_H$ variants had a more than 2-fold increase in affinity: I69M (2.4-fold), Y56G (2.6-fold), and Y50W (6.2-fold). In $V_L$, twelve out of nineteen variants met our cutoff with H34A, T50D, T51A, H89Q, T93N, Y94W, and an insertion of serine at position 31 showing substantially reduced binding. No $V_L$ variants with substantially increased affinity were identified.

Figure 4:
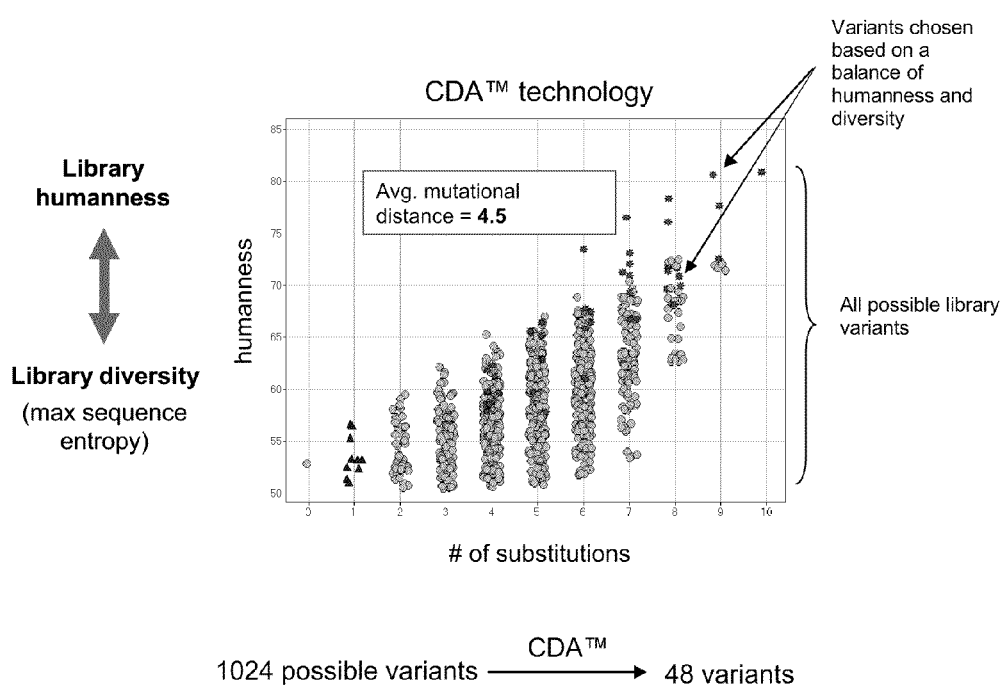
FIG. 4. Diagram illustrating CDA technology used to combine favorable single variants into $V_H$ and $V_L$ combination variants with high humanness scores and high library diversity while minimizing library size. Grey circles represent all possible library members and red stars indicate the members selected for the anti-CD25 $V_H$ combination variant library.

In the combination step, the ten heavy chain variants that met our affinity cutoff were explored in various combinations paired with the L1 light chain, and the twelve light chain variants in various combinations were paired with the H1 heavy chain. Since we were unsure how additive beneficial mutations would be, and since the number of possible combination variants is large (1024 for $V_H$ and 4096 for $V_L$), we developed a computational approach (Combination Design Automation or CDA™ technology) to the design of the combination variant library whereby humanness and diversity were balanced based on the number of variants desired (FIG. 4). We chose to construct a library of 48 $V_H$ variants paired with L1 and 48 $V_L$ variants paired with H1. FIG. 4 shows how CDA™ technology was used to design the library of 48 $V_H$ variants (shown as red circles) from all possible 1024 variants (grey circles). As can be seen from FIG. 4, the 48 variants with the best balance of humanness, number of substitutions, and mutational diversity were chosen for construction. All 96 total $V_H$ and $V_L$ combination variants were expressed, purified, and assayed for CD25 binding and results for four selected $V_H$ and $V_L$ combinations are shown in FIG. 5. These four $V_H$ combination variants all had substantially tighter binding than the starting template anti-CD25 H1L1: anti-CD25H1.12L1-8.0-fold tighter; anti-CD25 H1.14L1-2.4-fold tighter; anti-CD25 H1.22L1-4.9-fold tighter; and anti-CD25 H1.23L1-4.4-fold tighter. The single mutations in $V_H$ combined remarkably well and the variant that contained all 10 single mutations (anti-CD25 H1.12L1) had the highest affinity, demonstrating a high degree of additivity. For the $V_L$ combinations, all four of the shown variants had binding affinities within 2-fold of anti-CD25 H1L1.

Figure 7:
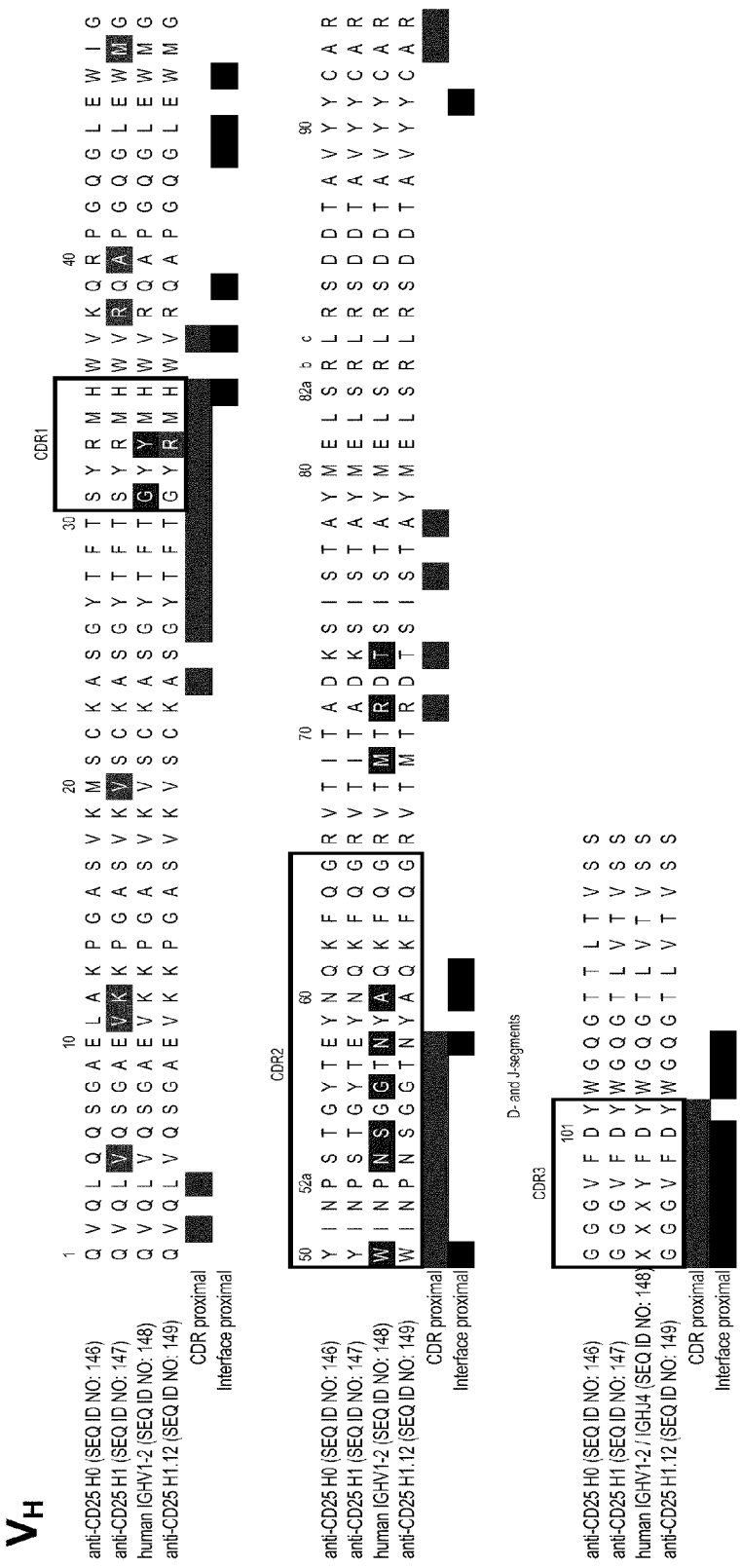
FIG. 7. (SEQ ID NO: 146-153) Amino acid sequence alignments of heavy chain and light chain variable regions for anti-TAC H0L0 (anti-CD25 H0L0-murine Fv), anti-CD25 H1 L1 (framework-optimized), human germlines IGHV1-2*02 (VH) and IGKV3-11*01 (VL), and engineered human equivalent anti-CD25H1.12L1.20 Amino acid differences between the following sequence pairs are highlighted: framework-optimized and murine Fv, human germline and framework-optimized, and engineered human equivalent anti-CD25H1.12L1.20 and human germline.
Figure 7:
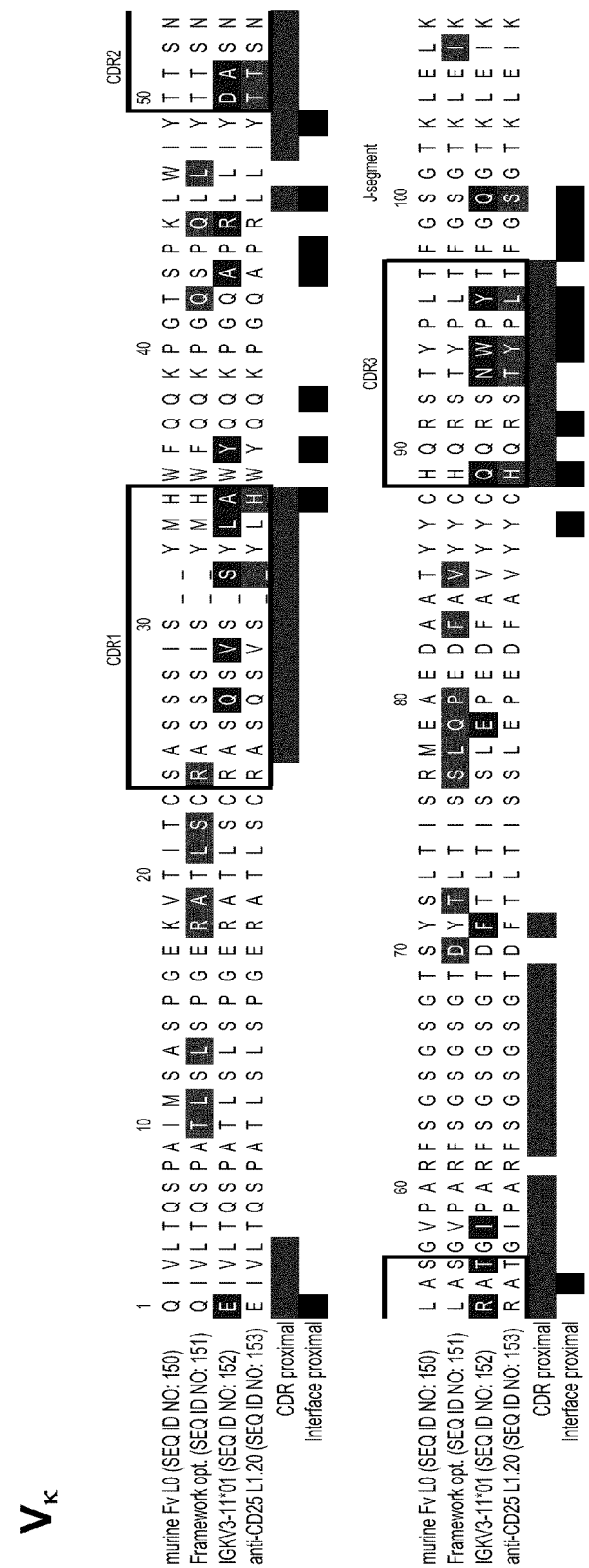

The four final $V_H$ and $V_L$ chains were paired with one another to create a library of sixteen human equivalent $V_H/V_L$ combination variants. Binding results and humanness scores are shown in FIG. 5. Compared to anti-CD25 H1L1, binding affinity ranged from 1.8-fold tighter in the case of variant anti-CD25 H1.14L1.20 to 5.9-fold tighter in the case of anti-CD25 H1.12L1.48. Antigen affinity was also comparable to anti-CD25 H0L0, with affinity differences ranging from 1.9-fold weaker to 1.7-fold tighter. Variant anti-CD25 H1.12L1.20 had the highest level of humanness and was ~1.5-fold tighter binding than anti-CD25 H0L0. Remarkably, this variant has twenty-two mutations compared to framework optimized anti-CD25 H1L1, twelve of which are in the Kabat defined CDRs. Biacore binding curves (25 nM CD25) for anti-CD25 H1.12L1.20 and its individual human equivalent chains paired with H1 or L1 are shown in FIG. 6, along with anti-CD25 H0L0 and daclizumab. Also shown in FIG. 6 is a plot of affinity versus number of identities to the closest human germline for anti-CD25 H0L0 (murine Fv), anti-CD25 H1 L1 (framework optimized), daclizumab, the sixteen engineered human equivalent VH/VL pairs, and anti-CD25 H1.12L1.20, demonstrating that we have progressively engineered the anti-CD25 Fv to be more human equivalent while simultaneously preserving antigen affinity. FIG. 7 shows an amino acid sequence alignment for anti-CD25 H0L0, anti-CD25 H1L1, the closest human germlines used for engineering, and anti-CD25 H1.12L1.20, with differences between the various sequence pairs highlighted.

Figure 8:
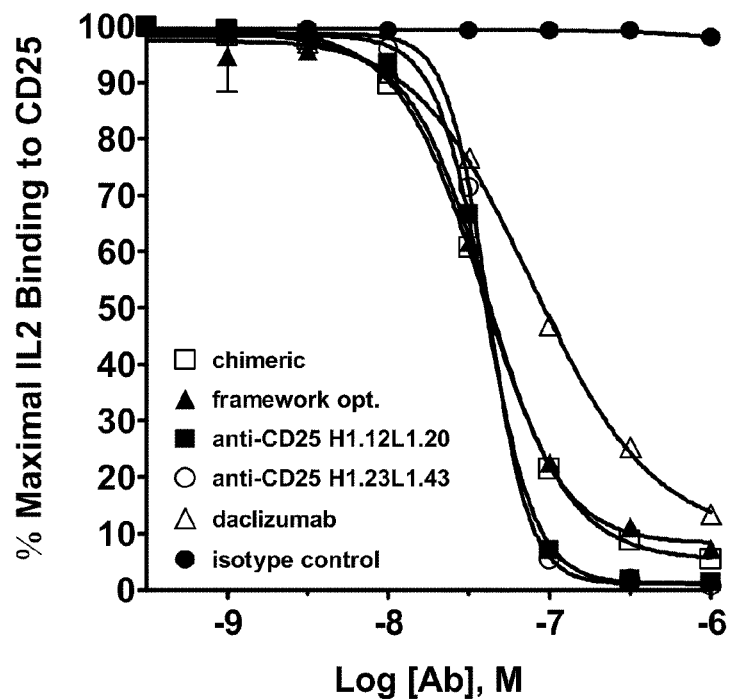
FIG. 8. Human equivalent anti-CD25 variants show high activity in a receptor blocking assay. Variants tested were chimeric (anti-CD25 H0L0), framework optimized (anti-CD25 H1L1), anti-CD25H1.12L1.20, anti-CD25H1.23L1.43, daclizumab, and a non-CD25 binding antibody as an isotype control. From EC50 values, relative potency of the mAbs was anti-CD25H1.12L1.20, anti-CD25H1.23L1.43>chimeric anti-CD25 H0L0, framework optimized anti-CD25 H1L1>daclizumab.

To demonstrate that our engineered human equivalent anti-CD25 mAbs had potent activity in another assay format, we evaluated two of our high affinity variants in a CD25 receptor blocking assay (FIG. 8). CD25 (R&D systems cat. #223-2A/CF) was coupled to a CM5 chip using standard coupling methods. Antibodies (chimeric anti-CD25 H0L0, framework optimized anti-CD25 H1L1, anti-CD25 H1.12L1.20, anti-CD25 H1.23L1.43, daclizumab, and an isotype control mAb) were serially diluted in half-log increments starting from 1000 nM to 0.1 nM and injected to block CD25 on the chip surface at 10 µL/min for 1 min, followed by injection of rh-IL2 (R&D Systems cat. #202-IL-010/CF) at 100 nM at the same speed for 1 min. To account for any drift resulting from the dissociation of the blocking antibody, IL-2 injection was preceded by injection of buffer alone so that the drift could be subtracted. The chip was regenerated after each cycle by injection of glycine buffer @ pH 1.5 for 30 sec at 10 µL/min. IL-2 binding was calculated from final relative RU values at the end of IL-2 injection. Curves were fit using a four parameter model in Prism 4.03. As can be seen from FIG. 9, both engineered human equivalent anti-CD25 mAbs showed a high degree of blocking IL-2 binding to CD25. From $EC_{50}$ values, relative potency of the mAbs was anti-CD25 H1.12L1.20, anti-CD25 H1.23L1.43>chimeric anti-CD25 H0L0, framework optimized anti-CD25 H1L1>daclizumab.

Example 2

Engineering of a Human Equivalent Anti-VEGF Monoclonal Antibody

An outline of the process of engineering a human equivalent anti-VEGF mAb from a murine anti-VEGF Fv is shown in FIG. 1. The murine anti-VEGF mAb A4.6.1 (Kim, et al., 1992, *Growth Factors* 7:53-64) was chosen as a starting point for engineering of a high affinity human equivalent anti-VEGF mAb. This mAb is the precursor of bevacizumab, a humanized and marketed anti-VEGF mAb used in the treatment of various types of cancer including colorectal, lung, and breast. The murine A4.6.1 Fv (anti-VEGF H0L0) was engineered into a "framework optimized" anti-VEGF mAb (anti-VEGF H1L1) by reducing the immunogenicity of the variable region using a method described in U.S. Ser. No. 11/004,590, entitled "Methods of Generating Variant Proteins with Increased Host String Content and Compositions Thereof", filed on Dec. 6, 2004. This method utilizes the homology present in human germline sequences and essentially makes murine to human mutations in order to increase the human string content of the Fv. Positions that are not within or proximal to the CDRs and $V_H/V_L$ interface are optimized in this step, and the relative humanness of the resulting Fv is comparable to mAbs humanized using CDR-grafting and other humanization techniques. Framework optimized heavy chain H1 and light chain L1 were constructed by gene synthesis, and Fab format antibodies were expressed transiently in 293E cells, purified by Ni-NTA chromatography, and evaluated by SDS-PAGE and SEC.

For kinetic analysis of anti-VEGF antibodies, VEGF was coupled to an activated CM5 biosensor chip using standard NHS-EDC chemistry by injecting 200 nM VEGF at a flow rate of 2 µL/min for 10 min. Binding was measured by injection of two-fold serial dilutions of anti-VEGF Fabs (3.13 nM to 200 nM) in buffer at 25° C. with a flow rate of 30 µL/min for 2 min followed by a dissociation phase of 4 min. Association rates ($k_{on}$) and dissociation rates ($k_{off}$) were calculated using a simple one-to-one Langmuir binding model (BIAcore Evaluation Software version 3.2). The equilibrium dissociation constant ($K_d$) was calculated as the ratio of $k_{off}/k_{on}$.

Figure 9:
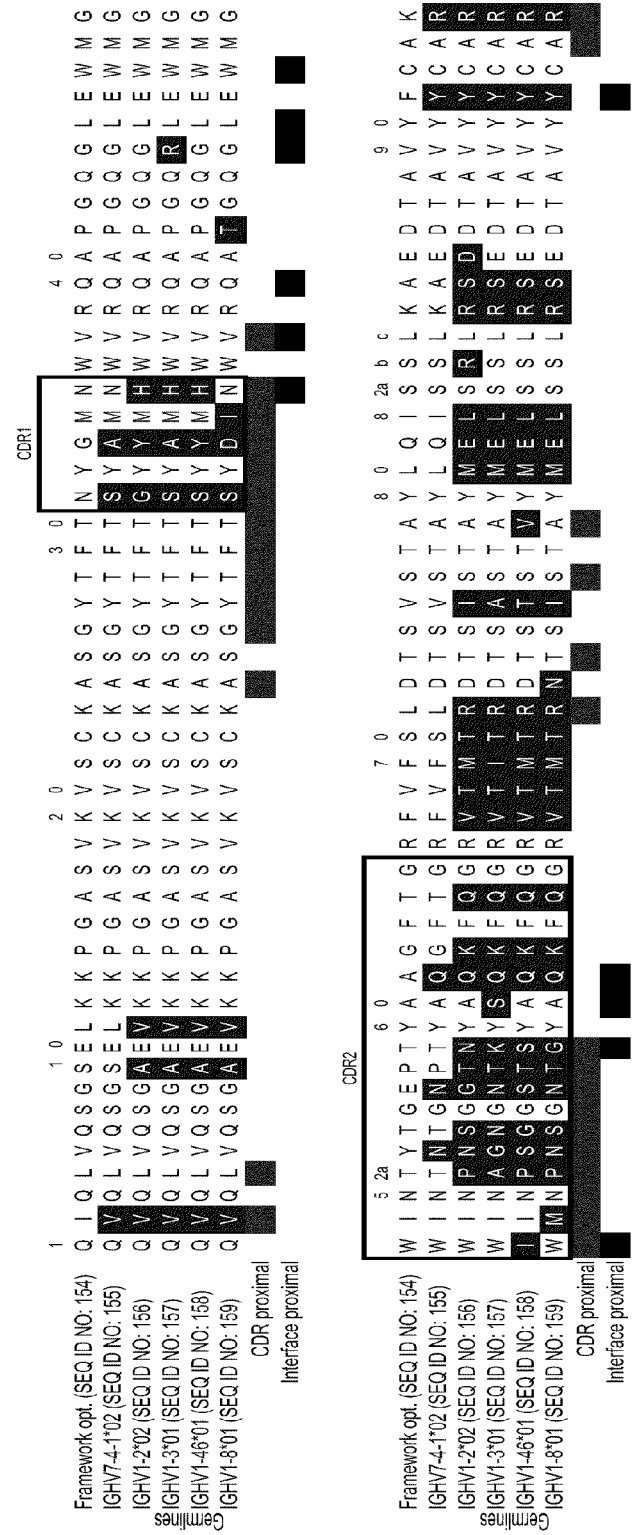
FIG. 9. (SEQ ID NO: 154-165) Comparison of the V-region ($V_H$ and $V_L$) and J-region ($V_L$) of an initial framework optimized anti-VEGF variable region sequence to the five closest matching human germline V-regions. Sequences are numbered according to Kabat et. al., and CDR regions are outlined. Amino acids in the human germline V-regions that differ from the framework optimized sequence are highlighted. Positions that are in CDRs or CDR proximal and/or proximal to the $V_H/V_L$ interface are indicated. For $V_L$, amino acids in common among all five J-regions are shown and those positions that differ are listed as X's.
Figure 9:
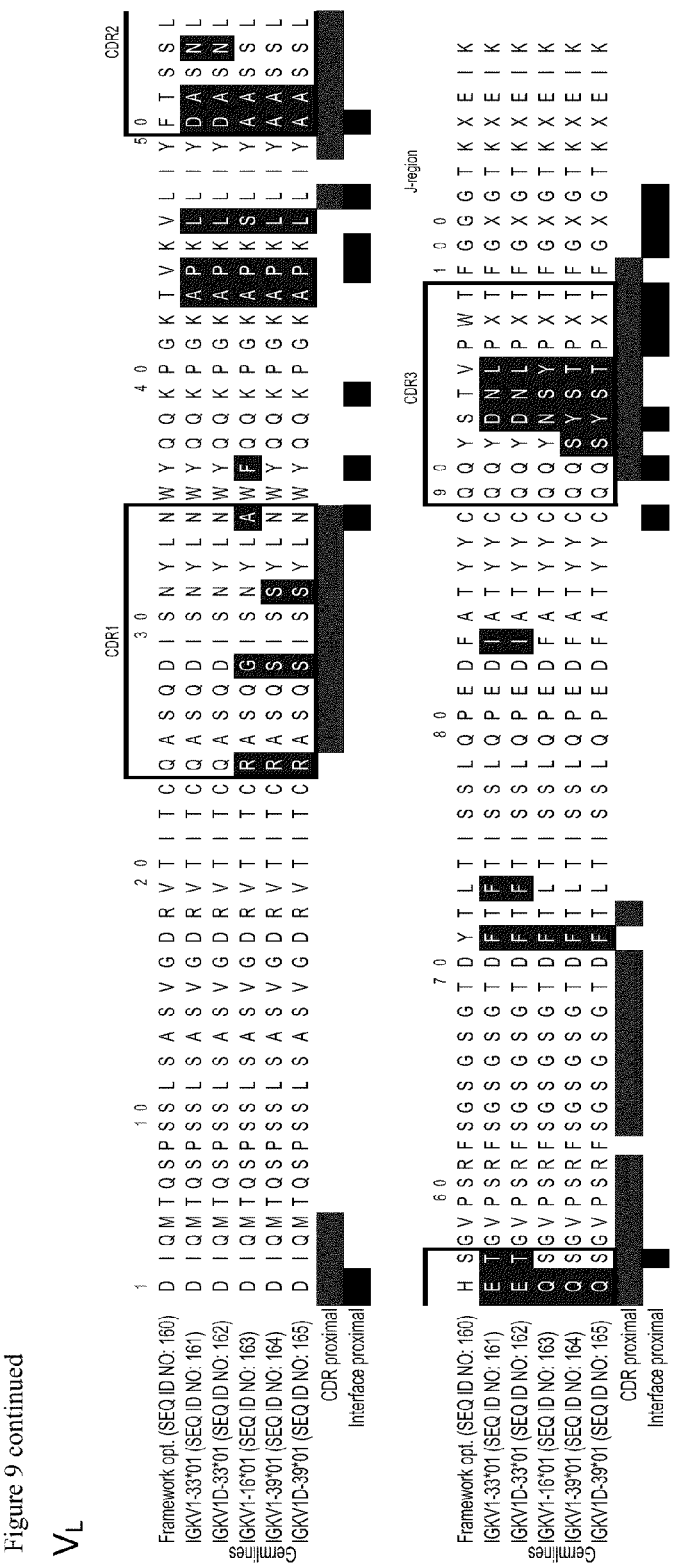

The framework optimized anti-VEGF heavy and light chains (H1 and L1, respectively) were aligned with the human germline V- and J-segments and the germlines were ranked based on the number of mutations away from the framework optimized sequence, the conservativeness of each mutation, and the proximity of each mutation to CDRs (FIG. 9). For $V_H$, the five highest ranking human germlines were IGHV7-4-1*02, IGHV1-2*02, IGHV1-3*01, IGHV1-46*01, and IGHV1-8*01, respectively. Germline V-segment IGHV7-4-1*02 was clearly the closest by being only eight mutations away from anti-VEGF H1, while the other four closest germlines were 30-31 mutations away. For $V_L$, the five highest ranking human germlines were IGKV1-33*01, IGKV1D-33*01, IGKV1-16*01, IGKV1D-39*01, and IGKV1D-39*01, all with fourteen differences from anti-VEGF L1.

The highest ranking $V_H$ germline IGHV7-4-1*02 and VL germline IGKV1-33*01 were chosen as the basis for further engineering. Single variants were constructed in the anti-VEGF H1L1 background and expressed, purified, and assayed as mentioned above in order to assess the impact of the eight differences between anti-VEGF H1 and IGHV7-4-1*02, and the fourteen differences between anti-VEGF L1 and IGKV1-33*01. Variants that had $K_d$ values similar to that of anti-VEGF H1L1 were selected to be combined in the next round of engineering.

In the combination step, the heavy chain variants that met our affinity cutoff were explored in various combinations paired with the L1 light chain, and the light chain variants in various combinations were paired with the H1 heavy chain. The heavy and light chains with the best combination of antigen affinity and humanness were subsequently combined into human equivalent $V_H/V_L$ pairs. All variants were expressed, purified, and assayed for VEGF binding and results for two selected $V_H$ and $V_L$ combinations along with anti-VEGF H0L0 and bevacizumab are shown in FIGS. 10 and 11. In FIG. 10, the top panel shows binding data for 100 nM of anti-VEGF H0L0 (murine Fv), anti-VEGF H1.33L1.51, anti-VEGF H1.33L1.55 and bevacizumab and the bottom panel shows relative VEGF affinity expressed as −Log [$K_d$] for the same four variants. FIG. 11 shows the human germline mutations included in the final two $V_H/V_L$ combination variants as well as $k_{on}$, $k_{off}$, $K_d$, fold change in $K_d$ compared to anti-VEGF H0L0, number of human 9-mers, and number of identities to the closest matching human germline V- and J-segments for the variants. As demonstrated by the data in FIGS. 10 and 11, the engineered human equivalent anti-VEGF mAbs have antigen affinities comparable to the marketed anti-VEGF mAb bevacizumab and within 3-fold of that of the chimeric antibody. Anti-VEGF H1.33L1.55 has thirteen more mutations compared to the framework optimized anti-VEGF H1L1, with nine of them located in the Kabat defined CDRs.

Example 3

Engineering of a Human Equivalent Anti-TNFα Monoclonal Antibody

An outline of the process of engineering a human equivalent anti-TNFα mAb from a murine anti-TNFα Fv is shown in FIG. 1. The murine anti-TNF mAb A2 (Knight, et al., 1993, Mol Immunol 30:1443-1453) was chosen as a starting point for engineering of a high affinity human equivalent anti-TNFα mAb. This mAb is the precursor of infliximab, a chimeric, marketed anti-TNFα mAb used in the treatment of rheumatoid arthritis. The murine A2 Fv (anti-TNFα H0L0) was engineered into a "framework optimized" anti-TNFα mAb (anti-TNFα H1L1) by reducing the immunogenicity of the variable region using a method described in U.S. Ser. No. 11/004,590, entitled "Methods of Generating Variant Proteins with Increased Host String Content and Compositions Thereof", filed on Dec. 6, 2004. This method utilizes the homology present in human germline sequences and essentially makes murine to human mutations in order to increase the human string content of the Fv. Positions that are not within or proximal to the CDRs and $V_H/V_L$ interface are optimized in this step, and the relative humanness of the resulting Fv is comparable to mAbs humanized using CDR-grafting and other humanization techniques. Framework optimized heavy chain H1 and light chain L1 were constructed by gene synthesis, and Fab format antibodies were expressed transiently in 293E cells, purified by Ni-NTA chromatography, and evaluated by SDS-PAGE and SEC.

For kinetic analysis of anti-TNFα antibodies, TNFα was coupled to an activated CM5 biosensor chip using standard NHS-EDC chemistry by injecting 200 nM TNFα at a flow rate of 2 µL/min for 10 min. Binding was measured by injection of two-fold serial dilutions of anti-TNF Fabs (6.25 nM to 50 nM) in buffer at 25° C. with a flow rate of 30 µL/min for 2 min followed by a dissociation phase of 3 min. For subsequent cycles, the chip was regenerated using pH4.0 acetate buffer. Association rates ($k_{on}$) and dissociation rates ($k_{off}$) were calculated using a simple one-to-one Langmuir binding model (BIAcore Evaluation Software version 3.2). The equilibrium dissociation constant ($K_d$) was calculated as the ratio of $k_{off}/k_{on}$. Data shown in Table 1 are the average of two independent runs with ±standard deviation shown.

The framework optimized anti-TNFα heavy and light chains (H1 and L1, respectively) were aligned with the human germline V- and J-segments and the germlines were ranked based on the number of mutations away from the framework optimized sequence, the conservativeness of each mutation, and the proximity of each mutation to CDRs. For $V_H$, the three highest ranking human germlines were IGHV3-73*01, IGHV3-72*01, and IGHV3-15*01, respectively. Germline V-segment IGHV3-73*01 was the closest with seventeen mutations away from anti-TNFα H1, while the other two closest germlines were 21-22 mutations away. For $V_L$, the three highest ranking human germlines were IGKV6-21*01, IGKV6D-21*01, and IGKV6D-41*01, with 11-24 differences from anti-TNFα L1.

The highest ranking $V_H$ germline IGHV3-73*01 and $V_L$ germline IGKV6-21*01 were chosen as the basis for further engineering. Single variants were constructed in the anti-TNFα H1L1 background and expressed, purified, and assayed as mentioned above in order to assess the impact of the seventeen differences between anti-TNFα H1 and IGHV3-73*01, and the eleven differences between anti-TNFα L1 and IGKV6-21*01. Variants that had $K_d$ values similar to that of anti-TNFα H1L1 were selected to be combined in the next round of engineering.

In the combination step, the heavy chain variants that met our affinity cutoff were explored in various combinations paired with the L1 light chain, and the light chain variants in various combinations were paired with the H1 heavy chain. The heavy and light chains with the best combination of antigen affinity and humanness were subsequently combined into human equivalent $V_H/V_L$ pairs. All variants were expressed, purified, and assayed for TNFα binding and results for four selected $V_H$ and $V_L$ combinations along with anti-TNFα H0L0 (A2; infliximab) and framework optimized anti-TNFα H1L1 are shown in Table 1. As demonstrated by the data in Table 1, the engineered human equivalent anti-TNFα mAbs have antigen affinities comparable to the marketed anti-TNF mAb infliximab and within 3-fold of that of the chimeric antibody. Anti-TNFα H1.103L1.33 has thirteen more mutations compared to the framework optimized anti-TNFα H1L1. Additional statistics for engineered mAbs are shown in FIG. 12.

TABLE 1

Binding measurement of anti-TNFα variants.

| Variant | $k_a$ (M/s × 10$^5$) | $k_d$ (1/s × 10$^{-4}$) | $K_d$ (nM) |
| --- | --- | --- | --- |
| Infliximab | 5.47 ± 1.88 | 13.10 ± 0.41 | 2.4 ± 0.1 |
| Anti-TNFα H1L1 | 6.05 ± 1.72 | 11.60 ± 0.40 | 1.9 ± 0.1 |
| Anti-TNFα H1.101L1.33 | 2.23 ± 0.41 | 8.74 ± 0.30 | 3.9 ± 0.7 |
| Anti-TNFα H1.45L1.33 | 4.89 ± 1.21 | 8.70 ± 0.30 | 1.8 ± 0.2 |
| Anti-TNFα H1.67L1.33 | 2.00 ± 0.42 | 7.76 ± 0.35 | 3.8 ± 0.9 |
| Anti-TNFα H1.103L1.33 | 2.92 ± 0.71 | 9.20 ± 0.30 | 3.1 ± 0.2 |

Example 4

Figure 13:
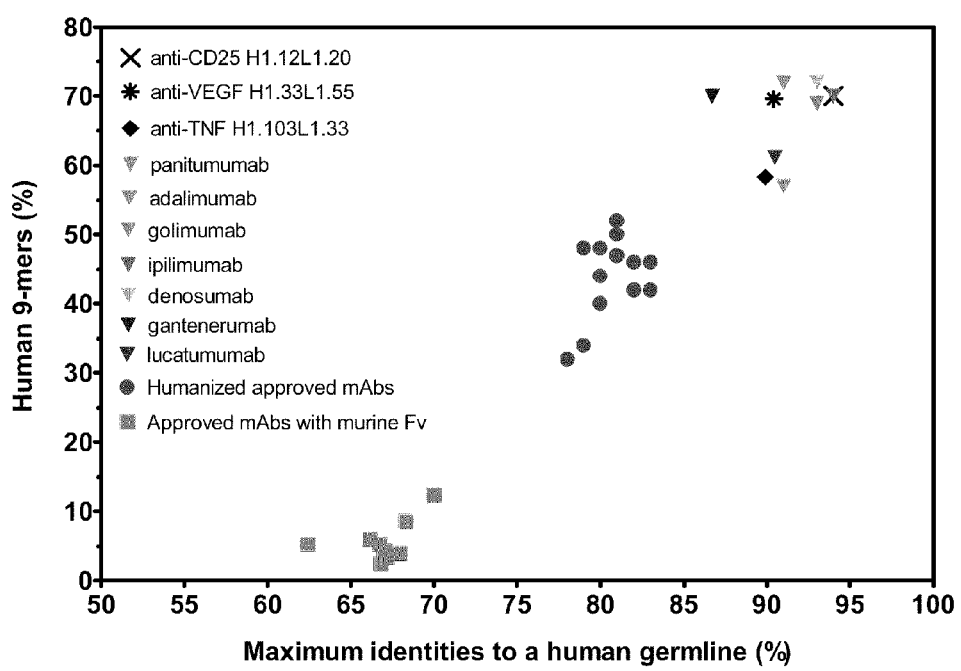
FIG. 13. Plot comparing humanness scores (% identity to the closest human germline V- and J-segments and % human 9-mers) for the approved and marketed murine, chimeric, and humanized monoclonal antibodies as well as several fully-human monoclonal antibodies in clinical development to fully-human anti-CD25H1.12L1.20, anti-VEGF H1.33L1.55, and anti-TNF H1.103L1.33. The fully-human antibodies engineered in this invention are comparable to the fully-human antibodies from transgenic mice and human phage display technologies.

Comparison of Engineered Human Equivalent mAbs to Human Equivalent mAbs Isolated from Transgenic Mice and Human Antibody Libraries To show that human equivalent mAbs engineered from murine variable regions are comparable in humanness to human equivalent mAbs isolated from transgenic mice or human phage display libraries, we obtained variable region sequences for currently marketed mAbs and several human equivalent mAbs in clinical development from the literature and analyzed their level of humanness as defined by the number of identities to the closest human germline and the number of human 9-mers. A plot of % identity to the closest human germline V and J-segments and % human 9-mers for approved murine, chimeric, and humanized mAbs as well as the two marketed human equivalent mAbs panitumumab and adalimumab is shown in FIG. 13. Also shown are five human equivalent mAbs in clinical development as well as the human equivalent mAbs engineered from murine variable regions, anti-CD25H1.12L1.20, anti-VEGF H1.33L1.55, and anti-TNF H1.103L1.33 (XmAb human equivalent mAbs). As can be seen from the plot, the sequences of human equivalent mAbs are more similar to those of human germlines than humanized and chimeric mAbs, thus human equivalent mAbs are expected to have less overall risk of immunogenicity. Also shown by the plot is that anti-CD25H1.12L1.20, anti-VEGF H1.33L1.55, and anti-TNFα H1.103L1.33 have levels of sequence humanness similar to human equivalent mAbs isolated from transgenic mice or human antibody libraries. FIG. 14 shows all antibodies included in the analysis and lists antigen, type of Fv (murine, humanized, or human equivalent), clinical status, the number and percent of identities to the closest human germline V- and J-segments, the number and percent of human 9-mers, the Fv length, and the VH and VL V- and J-segment germlines that had the highest identities and were used in the analysis.

The invention claimed is:

1. An isolated antibody that binds CD25, said antibody comprising a heavy chain and a light chain, said heavy chain comprising:
   a) a CDR1 having the amino acid sequence selected from the group consisting of SEQ ID NO:105 and SEQ ID NO:106;
   b) a CDR2 having the amino acid sequence of SEQ ID NO:107; and
   c) a CDR3 having the amino acid sequence of SEQ ID NO:110; and said light chain comprising:
   d) a CDR1 having the amino acid sequence of SEQ ID NO:118;
   e) a CDR2 having the amino acid sequence of SEQ ID NO:123; and
   f) a CDR3 having the amino acid sequence of SEQ ID NO:124.

2. The antibody according to claim 1, wherein said heavy chain comprises CDR1, CDR2, and CDR3 sequences as set forth in SEQ ID NOs: 105, 107, and 110, respectively, and the light chain comprises CDR1, CDR2, and CDR3 sequences as set forth in SEQ ID NOs: 118, 123, and 124, respectively.

3. The antibody according to claim 2, having a heavy chain variable region comprising the amino acid sequence of SEQ ID NO: 14 and a light chain variable region comprising the amino acid sequence of SEQ ID NO:64.

4. An isolated antibody that binds human CD25, said antibody comprising a heavy chain and a light chain, wherein said heavy chain comprises CDR1, CDR2, and CDR3 sequences as set forth in SEQ ID NOs: 105, 107, and 110, respectively, and the light chain comprises CDR1, CDR2, and CDR3 sequences as set forth in SEQ ID NOs: 118, 123, and 124, respectively.

* * * * *

```
                        SEQUENCE LISTING

<160> NUMBER OF SEQ ID NOS: 266

<210> SEQ ID NO 1
<211> LENGTH: 116
<212> TYPE: PRT
<213> ORGANISM: Mus musculus

<400> SEQUENCE: 1

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Arg Met His Trp Val Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Ala Arg Gly Gly Gly Val Phe Asp Tyr Trp Gly Gln Gly Thr Thr Leu
            100                 105                 110

Thr Val Ser Ser
        115

<210> SEQ ID NO 2
<211> LENGTH: 116
<212> TYPE: PRT
<213> ORGANISM: Artificial Sequence
<220> FEATURE:
<223> OTHER INFORMATION: framework-optimized anti-CD25 (H1)

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Met
        35                  40                  45

Gly Tyr Ile Asn Pro Ser Thr Gly Tyr Thr Glu Tyr Asn Gln Lys Phe
    50                  55                  60

Gln Gly Arg Val Thr Ile Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
            100                 105                 110
```

```
Thr Val Ser Ser
        115

<210> SEQ ID NO 3
<211> LENGTH: 116
<212> TYPE: PRT
<213> ORGANISM: Artificial Sequence
<220> FEATURE:
<223> OTHER INFORMATION: anti-CD25 H1.1 variable region

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Arg Met His Trp Val Arg Gln Ala Pro Gly Gln Gly Leu Glu Trp Met
            35                  40                  45

Gly Tyr Ile Asn Pro Ser Thr Gly Tyr Thr Glu Tyr Asn Gln Lys Phe
        50                  55                  60

Gln Gly Arg Val Thr Ile Thr Arg Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115

<210> SEQ ID NO 4
<211> LENGTH: 116
<212> TYPE: PRT
<213> ORGANISM: Artificial Sequence
<220> FEATURE:
<223> OTHER INFORMATION: anti-CD25 H1.2 variable region

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Arg Met His Trp Val Arg Gln Ala Pro Gly Gln Gly Leu Glu Trp Met
            35                  40                  45

Gly Tyr Ile Asn Pro Ser Thr Gly Tyr Thr Asn Tyr Asn Gln Lys Phe
        50                  55                  60

Gln Gly Arg Val Thr Ile Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115

<210> SEQ ID NO 5
<211> LENGTH: 116
<212> TYPE: PRT
<213> ORGANISM: Artificial Sequence
<220> FEATURE:
<223> OTHER INFORMATION: anti-CD25 H1.3 variable region

<400> SEQUENCE: 5
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Met
        35                  40                  45

Gly Tyr Ile Asn Pro Ser Thr Gly Tyr Thr Glu Tyr Asn Gln Lys Phe
    50                  55                  60

Gln Gly Arg Val Thr Met Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115

<210> SEQ ID NO 6
<211> LENGTH: 116
<212> TYPE: PRT
<213> ORGANISM: Artificial Sequence
<220> FEATURE:
<223> OTHER INFORMATION: anti-CD25 H1.4 variable region

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Met
        35                  40                  45

Gly Tyr Ile Asn Pro Ser Thr Gly Tyr Thr Glu Tyr Asn Gln Lys Phe
    50                  55                  60

Gln Gly Arg Val Thr Ile Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: anti-CD25 H1.5 variable region

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Met
        35                  40                  45

Gly Tyr Ile Asn Pro Ser Thr Gly Tyr Thr Glu Tyr Ala Gln Lys Phe
    50                  55                  60

```
Gln Gly Arg Val Thr Ile Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115

<210> SEQ ID NO 8
<211> LENGTH: 116
<212> TYPE: PRT
<213> ORGANISM: Artificial Sequence
<220> FEATURE:
<223> OTHER INFORMATION: anti-CD25 H1.6 variable region

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Tyr Ile Asn Pro Ser Thr Gly Tyr Thr Glu Tyr Asn Gln Lys Phe
    50                  55                  60

Gln Gly Arg Val Thr Ile Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115

<210> SEQ ID NO 9
<211> LENGTH: 116
<212> TYPE: PRT
<213> ORGANISM: Artificial Sequence
<220> FEATURE:
<223> OTHER INFORMATION: anti-CD25 H1.7 variable region

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Gly Gly Tyr Thr Phe Thr Ser Tyr
            20                  25                  30

Arg Met His Trp Val Arg Gln Ala Pro Gly Gln Gly Leu Glu Trp Met
        35                  40                  45

Gly Tyr Ile Asn Pro Ser Thr Gly Tyr Thr Glu Tyr Asn Gln Lys Phe
    50                  55                  60

Gln Gly Arg Val Thr Ile Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115
```

<210> SEQ ID NO 10
<211> LENGTH: 116
<212> TYPE: PRT
<213> ORGANISM: Artificial Sequence
<220> FEATURE:
<223> OTHER INFORMATION: anti-CD25 H1.8 variable region

<400> SEQUENCE: 10

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Met
        35                  40                  45

Gly Trp Ile Asn Pro Ser Thr Gly Tyr Thr Glu Tyr Asn Gln Lys Phe
    50                  55                  60

Gln Gly Arg Val Thr Ile Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115
```

<210> SEQ ID NO 11
<211> LENGTH: 116
<212> TYPE: PRT
<213> ORGANISM: Artificial Sequence
<220> FEATURE:
<223> OTHER INFORMATION: anti-CD25 H1.9 variable region

<400> SEQUENCE: 11

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Met
        35                  40                  45

Gly Tyr Ile Asn Pro Ser Thr Gly Tyr Thr Glu Tyr Asn Gln Lys Phe
    50                  55                  60

Gln Gly Arg Val Thr Ile Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115
```

<210> SEQ ID NO 12
<211> LENGTH: 116
<212> TYPE: PRT
<213> ORGANISM: Artificial Sequence
<220> FEATURE:
<223> OTHER INFORMATION: anti-CD25 H1.10 variable region

<400> SEQUENCE: 12

```
Gln Val Gln Leu Val Gln Ser Gly Ala Glu Val Lys Lys Pro Gly Ala
```

```
                1               5                   10                  15
Ser Val Lys Val Ser Cys Lys Ala Ser Gly Tyr Thr Phe Thr Ser Tyr
                20                  25                  30

Arg Met His Trp Val Arg Gln Ala Pro Gly Gln Gly Leu Glu Trp Met
                35                  40                  45

Gly Tyr Ile Asn Pro Asn Thr Gly Tyr Thr Glu Tyr Asn Gln Lys Phe
                50                  55                  60

Gln Gly Arg Val Thr Ile Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
                100                 105                 110

Thr Val Ser Ser
        115

<210> SEQ ID NO 13
<211> LENGTH: 116
<212> TYPE: PRT
<213> ORGANISM: Artificial Sequence
<220> FEATURE:
<223> OTHER INFORMATION: anti-CD25 H1.11 variable region

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Arg Met His Trp Val Arg Gln Ala Pro Gly Gln Gly Leu Glu Trp Met
                35                  40                  45

Gly Tyr Ile Asn Pro Ser Ser Gly Tyr Thr Glu Tyr Asn Gln Lys Phe
                50                  55                  60

Gln Gly Arg Val Thr Ile Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
                100                 105                 110

Thr Val Ser Ser
        115

<210> SEQ ID NO 14
<211> LENGTH: 116
<212> TYPE: PRT
<213> ORGANISM: Artificial Sequence
<220> FEATURE:
<223> OTHER INFORMATION: anti-CD25 H1.12 variable region

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Arg Met His Trp Val Arg Gln Ala Pro Gly Gln Gly Leu Glu Trp Met
                35                  40                  45

Gly Trp Ile Asn Pro Asn Ser Gly Gly Thr Asn Tyr Ala Gln Lys Phe
                50                  55                  60

Gln Gly Arg Val Thr Met Thr Arg Asp Thr Ser Ile Ser Thr Ala Tyr
```

```
                    65                  70                  75                  80
Met Glu Leu Ser Arg Leu Arg Ser Asp Asp Thr Ala Val Tyr Tyr Cys
                    85                  90                  95

Ala Arg Gly Gly Gly Val Phe Asp Tyr Trp Gly Gln Gly Thr Leu Val
                100                 105                 110

Thr Val Ser Ser
            115

<210> SEQ ID NO 15
<211> LENGTH: 116
<212> TYPE: PRT
<213> ORGANISM: Artificial Sequence
<220> FEATURE:
<223> OTHER INFORMATION: anti-CD25 H1.14 variable region

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Arg Met His Trp Val Arg Gln Ala Pro Gly Gln Gly Leu Glu Trp Met
                35                  40                  45

Gly Tyr Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
                100                 105                 110

Thr Val Ser Ser
            115

<210> SEQ ID NO 16
<211> LENGTH: 116
<212> TYPE: PRT
<213> ORGANISM: Artificial Sequence
<220> FEATURE:
<223> OTHER INFORMATION: anti-CD25 H1.22 variable region

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Arg Met His Trp Val Arg Gln Ala Pro Gly Gln Gly Leu Glu Trp Met
                35                  40                  45

Gly Trp Ile Asn Pro Asn Ser Gly Gly Thr Asn Tyr Ala Gln Lys Phe
        50                  55                  60

Gln Gly Arg Val Thr Ile Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
                100                 105                 110

Thr Val Ser Ser
            115
```

```
<210> SEQ ID NO 17
<211> LENGTH: 116
<212> TYPE: PRT
<213> ORGANISM: Artificial Sequence
<220> FEATURE:
<223> OTHER INFORMATION: anti-CD25 H1.23 variable region

<400> SEQUENCE: 17
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Arg Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115

```
<210> SEQ ID NO 18
<211> LENGTH: 123
<212> TYPE: PRT
<213> ORGANISM: Mus musculus

<400> SEQUENCE: 18
```

Glu Ile Gln Leu Val Gln Ser Gly Pro Glu Leu Lys Gln Pro Gly Glu
1               5                   10                  15

Thr Val Arg Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Glu Thr Ser Ala Ser Thr Ala Tyr
65                  70                  75                  80

Leu Gln Ile Ser Asn Leu Lys Asn Asp Asp Thr Ala Thr Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Thr Thr Val Thr Val Ser Ser
        115                 120

```
<210> SEQ ID NO 19
<211> LENGTH: 123
<212> TYPE: PRT
<213> ORGANISM: Artificial Sequence
<220> FEATURE:
<223> OTHER INFORMATION: framework-optimized anti-VEGF (H1)

<400> SEQUENCE: 19
```

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Tyr Ala Ala Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
            115                 120

<210> SEQ ID NO 20
<211> LENGTH: 123
<212> TYPE: PRT
<213> ORGANISM: Artificial Sequence
<220> FEATURE:
<223> OTHER INFORMATION: anti-VEGF H1.1 variable region

<400> SEQUENCE: 20

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Tyr Ala Ala Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
            115                 120

<210> SEQ ID NO 21
<211> LENGTH: 123
<212> TYPE: PRT
<213> ORGANISM: Artificial Sequence
<220> FEATURE:
<223> OTHER INFORMATION: anti-VEGF H1.2 variable region

<400> SEQUENCE: 21

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Tyr Ala Ala Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

```
Ala Lys Tyr Pro His Tyr Tyr Gly Ser Ser His Trp Tyr Phe Asp Val
            100                 105                 110

Trp Gly Ala Gly Thr Leu Val Thr Val Ser Ser
        115                 120

<210> SEQ ID NO 22
<211> LENGTH: 123
<212> TYPE: PRT
<213> ORGANISM: Artificial Sequence
<220> FEATURE:
<223> OTHER INFORMATION: anti-VEGF H1.3 variable region

<400> SEQUENCE: 22

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Ala Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Ala Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
        115                 120

<210> SEQ ID NO 23
<211> LENGTH: 123
<212> TYPE: PRT
<213> ORGANISM: Artificial Sequence
<220> FEATURE:
<223> OTHER INFORMATION: anti-VEGF H1.4 variable region

<400> SEQUENCE: 23

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asn Thr Gly Glu Pro Thr Tyr Ala Ala Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
        115                 120

<210> SEQ ID NO 24
<211> LENGTH: 123
<212> TYPE: PRT
<213> ORGANISM: Artificial Sequence
```

```
<220> FEATURE:
<223> OTHER INFORMATION: anti-VEGF H1.5 variable region

<400> SEQUENCE: 24

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Asn Pro Thr Tyr Ala Ala Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
        115                 120

<210> SEQ ID NO 25
<211> LENGTH: 123
<212> TYPE: PRT
<213> ORGANISM: Artificial Sequence
<220> FEATURE:
<223> OTHER INFORMATION: anti-VEGF H1.6 variable region

<400> SEQUENCE: 25

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
        115                 120

<210> SEQ ID NO 26
<211> LENGTH: 123
<212> TYPE: PRT
<213> ORGANISM: Artificial Sequence
<220> FEATURE:
<223> OTHER INFORMATION: anti-VEGF H1.7 variable region

<400> SEQUENCE: 26

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
```

```
                35                  40                  45
Gly Trp Ile Asn Thr Tyr Thr Gly Glu Pro Thr Tyr Ala Ala Gly Phe
        50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
            115                 120

<210> SEQ ID NO 27
<211> LENGTH: 123
<212> TYPE: PRT
<213> ORGANISM: Artificial Sequence
<220> FEATURE:
<223> OTHER INFORMATION: anti-VEGF H1.8 variable region

<400> SEQUENCE: 27

Gln Ile Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Gly Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Ala Gly Phe
        50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
            115                 120

<210> SEQ ID NO 28
<211> LENGTH: 123
<212> TYPE: PRT
<213> ORGANISM: Artificial Sequence
<220> FEATURE:
<223> OTHER INFORMATION: anti-VEGF H1.9 variable region

<400> SEQUENCE: 28

Gln Ile Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
                20                  25                  30

Ser Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Ala Gly Phe
        50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                85                  90                  95

Ala Lys Tyr Pro His Tyr Tyr Gly Ser Ser His Trp Tyr Phe Asp Val
```

-continued

```
                      100                 105                 110
Trp Gly Ala Gly Thr Leu Val Thr Val Ser Ser
            115                 120

<210> SEQ ID NO 29
<211> LENGTH: 123
<212> TYPE: PRT
<213> ORGANISM: Artificial Sequence
<220> FEATURE:
<223> OTHER INFORMATION: anti-VEGF H1.10 variable region

<400> SEQUENCE: 29

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Ala Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
            115                 120

<210> SEQ ID NO 30
<211> LENGTH: 123
<212> TYPE: PRT
<213> ORGANISM: Artificial Sequence
<220> FEATURE:
<223> OTHER INFORMATION: anti-VEGF H1.11 variable region

<400> SEQUENCE: 30

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Tyr Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Ala Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
            115                 120

<210> SEQ ID NO 31
<211> LENGTH: 123
<212> TYPE: PRT
<213> ORGANISM: Artificial Sequence
<220> FEATURE:
<223> OTHER INFORMATION: anti-VEGF H1.12 variable region
```

<400> SEQUENCE: 31

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Ala Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
            115                 120

<210> SEQ ID NO 32
<211> LENGTH: 123
<212> TYPE: PRT
<213> ORGANISM: Artificial Sequence
<220> FEATURE:
<223> OTHER INFORMATION: anti-VEGF H1.13 variable region

<400> SEQUENCE: 32

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Asp Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Ala Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
            115                 120

<210> SEQ ID NO 33
<211> LENGTH: 123
<212> TYPE: PRT
<213> ORGANISM: Artificial Sequence
<220> FEATURE:
<223> OTHER INFORMATION: anti-VEGF H1.32 variable region

<400> SEQUENCE: 33

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

```
Gly Trp Ile Asn Thr Tyr Thr Gly Glu Pro Thr Tyr Ala Ala Gly Phe
        50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
        115                 120

<210> SEQ ID NO 34
<211> LENGTH: 123
<212> TYPE: PRT
<213> ORGANISM: Artificial Sequence
<220> FEATURE:
<223> OTHER INFORMATION: anti-VEGF H1.33 variable region

<400> SEQUENCE: 34

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
                 20                  25                  30

Gly Met Asn Trp Val Arg Gln Ala Pro Gly Gln Gly Leu Glu Trp Met
             35                  40                  45

Gly Trp Ile Asn Thr Tyr Thr Gly Asn Pro Thr Tyr Ala Gln Gly Phe
        50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
        115                 120

<210> SEQ ID NO 35
<211> LENGTH: 123
<212> TYPE: PRT
<213> ORGANISM: Artificial Sequence
<220> FEATURE:
<223> OTHER INFORMATION: anti-VEGF H1.34 variable region

<400> SEQUENCE: 35

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Ser Tyr
                 20                  25                  30

Ala Met Asn Trp Val Arg Gln Ala Pro Gly Gln Gly Leu Glu Trp Met
             35                  40                  45

Gly Trp Ile Asn Thr Tyr Thr Gly Asn Pro Thr Tyr Ala Gln Gly Phe
        50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                 85                  90                  95

Ala Lys Tyr Pro His Tyr Tyr Gly Ser Ser His Trp Tyr Phe Asp Val
            100                 105                 110
```

```
Trp Gly Ala Gly Thr Leu Val Thr Val Ser Ser
        115                 120

<210> SEQ ID NO 36
<211> LENGTH: 123
<212> TYPE: PRT
<213> ORGANISM: Artificial Sequence
<220> FEATURE:
<223> OTHER INFORMATION: anti-VEGF H1.35 variable region

<400> SEQUENCE: 36

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Tyr Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
        115                 120

<210> SEQ ID NO 37
<211> LENGTH: 123
<212> TYPE: PRT
<213> ORGANISM: Artificial Sequence
<220> FEATURE:
<223> OTHER INFORMATION: anti-VEGF H1.36 variable region

<400> SEQUENCE: 37

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Tyr Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
        115                 120

<210> SEQ ID NO 38
<211> LENGTH: 123
<212> TYPE: PRT
<213> ORGANISM: Artificial Sequence
<220> FEATURE:
<223> OTHER INFORMATION: anti-VEGF H1.37 variable region

<400> SEQUENCE: 38
```

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Tyr Thr Gly Asn Pro Tyr Ala Ala Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
            115                 120
```

<210> SEQ ID NO 39
<211> LENGTH: 123
<212> TYPE: PRT
<213> ORGANISM: Artificial Sequence
<220> FEATURE:
<223> OTHER INFORMATION: anti-VEGF H1.38 variable region

<400> SEQUENCE: 39

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
            115                 120
```

<210> SEQ ID NO 40
<211> LENGTH: 123
<212> TYPE: PRT
<213> ORGANISM: Artificial Sequence
<220> FEATURE:
<223> OTHER INFORMATION: anti-VEGF H1.39 variable region

<400> SEQUENCE: 40

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Tyr Tyr
            20                  25                  30

Ala Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Ala Gly Phe
    50                  55                  60
```

```
Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
        115                 120
```

<210> SEQ ID NO 41
<211> LENGTH: 123
<212> TYPE: PRT
<213> ORGANISM: Artificial Sequence
<220> FEATURE:
<223> OTHER INFORMATION: anti-VEGF H1.40 variable region

<400> SEQUENCE: 41

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Tyr Tyr
                 20                  25                  30

Ala Met Asn Trp Val Arg Gln Ala Pro Gly Gln Gly Leu Glu Trp Met
             35                  40                  45

Gly Trp Ile Asn Thr Tyr Thr Gly Asn Pro Thr Tyr Ala Gln Gly Phe
     50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                 85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
        115                 120
```

<210> SEQ ID NO 42
<211> LENGTH: 123
<212> TYPE: PRT
<213> ORGANISM: Artificial Sequence
<220> FEATURE:
<223> OTHER INFORMATION: anti-VEGF H1.41 variable region

<400> SEQUENCE: 42

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Tyr Tyr
                 20                  25                  30

Ala Met Asn Trp Val Arg Gln Ala Pro Gly Gln Gly Leu Glu Trp Met
             35                  40                  45

Gly Trp Ile Asn Thr Tyr Thr Gly Asn Pro Thr Tyr Ala Gln Gly Phe
     50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Ala Gly Thr Leu Val Thr Val Ser Ser
        115                 120
```

<210> SEQ ID NO 43
<211> LENGTH: 106
<212> TYPE: PRT
<213> ORGANISM: Mus musculus

<400> SEQUENCE: 43

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Ile Ser Tyr Met
            20                  25                  30

His Trp Phe Gln Gln Lys Pro Gly Thr Ser Pro Lys Leu Trp Ile Tyr
        35                  40                  45

Thr Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys His Gln Arg Ser Thr Tyr Pro Leu Thr
                85                  90                  95

Phe Gly Ser Gly Thr Lys Leu Glu Leu Lys
            100                 105
```

<210> SEQ ID NO 44
<211> LENGTH: 106
<212> TYPE: PRT
<213> ORGANISM: Artificial Sequence
<220> FEATURE:
<223> OTHER INFORMATION: framework-optimized anti-CD25 (L1)

<400> SEQUENCE: 44

```
Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Ile Ser Tyr Met
            20                  25                  30

His Trp Phe Gln Gln Lys Pro Gly Gln Ser Pro Gln Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105
```

<210> SEQ ID NO 45
<211> LENGTH: 106
<212> TYPE: PRT
<213> ORGANISM: Artificial Sequence
<220> FEATURE:
<223> OTHER INFORMATION: anti-CD25 L1.1 variable region

<400> SEQUENCE: 45

```
Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Ile Ser Tyr Met
            20                  25                  30

His Trp Phe Gln Gln Lys Pro Gly Gln Ser Pro Gln Leu Leu Ile Tyr
        35                  40                  45
```

Thr Thr Ser Asn Leu Ala Ser Gly Val Pro Ala Arg Phe Ser Gly Ser
            50                  55                  60

Gly Ser Gly Thr Asp Tyr Thr Leu Thr Ile Ser Ser Leu Gln Pro Glu
 65                  70                  75                  80

Asp Phe Ala Val Tyr Tyr Cys Gln Gln Arg Ser Thr Tyr Pro Leu Thr
                 85                  90                  95

Phe Gly Ser Gly Thr Lys Leu Glu Ile Lys
            100                 105

<210> SEQ ID NO 46
<211> LENGTH: 106
<212> TYPE: PRT
<213> ORGANISM: Artificial Sequence
<220> FEATURE:
<223> OTHER INFORMATION: anti-CD25 L1.2 variable region

<400> SEQUENCE: 46

Gln Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Val Ser Tyr Met
                 20                  25                  30

His Trp Phe Gln Gln Lys Pro Gly Gln Ser Pro Gln Leu Leu Ile Tyr
             35                  40                  45

Thr Thr Ser Asn Leu Ala Ser Gly Val Pro Ala Arg Phe Ser Gly Ser
         50                  55                  60

Gly Ser Gly Thr Asp Tyr Thr Leu Thr Ile Ser Ser Leu Gln Pro Glu
 65                  70                  75                  80

Asp Phe Ala Val Tyr Tyr Cys His Gln Arg Ser Thr Tyr Pro Leu Thr
                 85                  90                  95

Phe Gly Ser Gly Thr Lys Leu Glu Ile Lys
            100                 105

<210> SEQ ID NO 47
<211> LENGTH: 106
<212> TYPE: PRT
<213> ORGANISM: Artificial Sequence
<220> FEATURE:
<223> OTHER INFORMATION: anti-CD25 L1.3 variable region

<400> SEQUENCE: 47

Gln Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Ile Ser Tyr Met
                 20                  25                  30

His Trp Phe Gln Gln Lys Pro Gly Gln Ser Pro Gln Leu Leu Ile Tyr
             35                  40                  45

Thr Thr Ser Asn Arg Ala Ser Gly Val Pro Ala Arg Phe Ser Gly Ser
         50                  55                  60

Gly Ser Gly Thr Asp Tyr Thr Leu Thr Ile Ser Ser Leu Gln Pro Glu
 65                  70                  75                  80

Asp Phe Ala Val Tyr Tyr Cys His Gln Arg Ser Thr Tyr Pro Leu Thr
                 85                  90                  95

Phe Gly Ser Gly Thr Lys Leu Glu Ile Lys
            100                 105

<210> SEQ ID NO 48
<211> LENGTH: 106
<212> TYPE: PRT
<213> ORGANISM: Artificial Sequence
<220> FEATURE:

<223> OTHER INFORMATION: anti-CD25 L1.4 variable region

<400> SEQUENCE: 48

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ile Ser Tyr Leu
            20                  25                  30

His Trp Phe Gln Gln Lys Pro Gly Gln Ser Pro Gln Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 49
<211> LENGTH: 106
<212> TYPE: PRT
<213> ORGANISM: Artificial Sequence
<220> FEATURE:
<223> OTHER INFORMATION: anti-CD25 L1.5 variable region

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ile Ser Tyr Met
            20                  25                  30

His Trp Phe Gln Gln Lys Pro Gly Gln Ser Pro Gln Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 50
<211> LENGTH: 106
<212> TYPE: PRT
<213> ORGANISM: Artificial Sequence
<220> FEATURE:
<223> OTHER INFORMATION: anti-CD25 L1.6 variable region

<400> SEQUENCE: 50

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ile Ser Tyr Met
            20                  25                  30

His Trp Phe Gln Gln Lys Pro Gly Gln Ser Pro Arg Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Gln Pro Glu
65                  70                  75                  80

```
Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 51
<211> LENGTH: 106
<212> TYPE: PRT
<213> ORGANISM: Artificial Sequence
<220> FEATURE:
<223> OTHER INFORMATION: anti-CD25 L1.7 variable region

<400> SEQUENCE: 51

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Ile Ser Tyr Met
                20                  25                  30

His Trp Phe Gln Gln Lys Pro Gly Gln Ser Pro Gln Leu Leu Ile Tyr
            35                  40                  45

Thr Thr Ser Asn Leu Ala Ser Gly Val Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 52
<211> LENGTH: 106
<212> TYPE: PRT
<213> ORGANISM: Artificial Sequence
<220> FEATURE:
<223> OTHER INFORMATION: anti-CD25 L1.8 variable region

<400> SEQUENCE: 52

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Tyr Met
                20                  25                  30

His Trp Phe Gln Gln Lys Pro Gly Gln Ser Pro Gln Leu Leu Ile Tyr
            35                  40                  45

Thr Thr Ser Asn Leu Ala Ser Gly Val Pro Ala Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 53
<211> LENGTH: 106
<212> TYPE: PRT
<213> ORGANISM: Artificial Sequence
<220> FEATURE:
<223> OTHER INFORMATION: anti-CD25 L1.9 variable region

<400> SEQUENCE: 53

Gln Ile Val Leu Thr Gln Ser Pro Ala Thr Leu Ser Leu Ser Pro Gly
```

```
                  1               5                  10                 15
            Glu Arg Ala Thr Leu Ser Cys Arg Ala Ser Ser Ser Ile Ser Tyr Met
                            20                  25                  30

His Trp Phe Gln Gln Lys Pro Gly Gln Ala Pro Gln Leu Leu Ile Tyr
                            35                  40                  45

Thr Thr Ser Asn Leu Ala Ser Gly Val Pro Ala Arg Phe Ser Gly Ser
                        50                  55                  60

Gly Ser Gly Thr Asp Tyr Thr Leu Thr Ile Ser Ser Leu Gln Pro Glu
            65                  70                  75                  80

Asp Phe Ala Val Tyr Tyr Cys His Gln Arg Ser Thr Tyr Pro Leu Thr
                            85                  90                  95

Phe Gly Ser Gly Thr Lys Leu Glu Ile Lys
                            100                 105

<210> SEQ ID NO 54
<211> LENGTH: 106
<212> TYPE: PRT
<213> ORGANISM: Artificial Sequence
<220> FEATURE:
<223> OTHER INFORMATION: anti-CD25 L1.10 variable region

<400> SEQUENCE: 54

Gln Ile Val Leu Thr Gln Ser Pro Ala Thr Leu Ser Leu Ser Pro Gly
            1               5                   10                  15

Glu Arg Ala Thr Leu Ser Cys Arg Ala Ser Ser Ser Ile Ser Tyr Met
                            20                  25                  30

His Trp Phe Gln Gln Lys Pro Gly Gln Ser Pro Gln Leu Leu Ile Tyr
                            35                  40                  45

Thr Thr Ser Asn Leu Ala Thr Gly Val Pro Ala Arg Phe Ser Gly Ser
                        50                  55                  60

Gly Ser Gly Thr Asp Tyr Thr Leu Thr Ile Ser Ser Leu Gln Pro Glu
            65                  70                  75                  80

Asp Phe Ala Val Tyr Tyr Cys His Gln Arg Ser Thr Tyr Pro Leu Thr
                            85                  90                  95

Phe Gly Ser Gly Thr Lys Leu Glu Ile Lys
                            100                 105

<210> SEQ ID NO 55
<211> LENGTH: 106
<212> TYPE: PRT
<213> ORGANISM: Artificial Sequence
<220> FEATURE:
<223> OTHER INFORMATION: anti-CD25 L1.11 variable region

<400> SEQUENCE: 55

Gln Ile Val Leu Thr Gln Ser Pro Ala Thr Leu Ser Leu Ser Pro Gly
            1               5                   10                  15

Glu Arg Ala Thr Leu Ser Cys Arg Ala Ser Ser Ser Ile Ser Tyr Met
                            20                  25                  30

His Trp Phe Gln Gln Lys Pro Gly Gln Ser Pro Gln Leu Leu Ile Tyr
                            35                  40                  45

Asp Thr Ser Asn Leu Ala Ser Gly Val Pro Ala Arg Phe Ser Gly Ser
                        50                  55                  60

Gly Ser Gly Thr Asp Tyr Thr Leu Thr Ile Ser Ser Leu Gln Pro Glu
            65                  70                  75                  80

Asp Phe Ala Val Tyr Tyr Cys His Gln Arg Ser Thr Tyr Pro Leu Thr
                            85                  90                  95

Phe Gly Ser Gly Thr Lys Leu Glu Ile Lys
```

-continued

<210> SEQ ID NO 56
<211> LENGTH: 106
<212> TYPE: PRT
<213> ORGANISM: Artificial Sequence
<220> FEATURE:
<223> OTHER INFORMATION: anti-CD25 L1.12 variable region

<400> SEQUENCE: 56

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Ile Ser Tyr Met
            20                  25                  30

His Trp Phe Gln Gln Lys Pro Gly Gln Ser Pro Gln Leu Leu Ile Tyr
        35                  40                  45

Thr Ala Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 57
<211> LENGTH: 106
<212> TYPE: PRT
<213> ORGANISM: Artificial Sequence
<220> FEATURE:
<223> OTHER INFORMATION: anti-CD25 L1.13 variable region

<400> SEQUENCE: 57

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Ile Ser Tyr Met
            20                  25                  30

His Trp Phe Gln Gln Lys Pro Gly Gln Ser Pro Gln Leu Leu Ile Tyr
        35                  40                  45

Thr Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 58
<211> LENGTH: 106
<212> TYPE: PRT
<213> ORGANISM: Artificial Sequence
<220> FEATURE:
<223> OTHER INFORMATION: anti-CD25 L1.14 variable region

<400> SEQUENCE: 58

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Ile Ser Tyr Met
            20                  25                  30

His Trp Phe Gln Gln Lys Pro Gly Gln Ser Pro Gln Leu Leu Ile Tyr
            35                  40                  45

Thr Thr Ser Asn Leu Ala Ser Gly Val Pro Ala Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 59
<211> LENGTH: 106
<212> TYPE: PRT
<213> ORGANISM: Artificial Sequence
<220> FEATURE:
<223> OTHER INFORMATION: anti-CD25 L1.15 variable region

<400> SEQUENCE: 59

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Ile Ser Tyr Met
            20                  25                  30

Ala Trp Phe Gln Gln Lys Pro Gly Gln Ser Pro Gln Leu Leu Ile Tyr
            35                  40                  45

Thr Thr Ser Asn Leu Ala Ser Gly Val Pro Ala Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 60
<211> LENGTH: 106
<212> TYPE: PRT
<213> ORGANISM: Artificial Sequence
<220> FEATURE:
<223> OTHER INFORMATION: anti-CD25 L1.16 variable region

<400> SEQUENCE: 60

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Ile Ser Tyr Met
            20                  25                  30

His Trp Tyr Gln Gln Lys Pro Gly Gln Ser Pro Gln Leu Leu Ile Tyr
            35                  40                  45

Thr Thr Ser Asn Leu Ala Ser Gly Val Pro Ala Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 61
<211> LENGTH: 106

```
<212> TYPE: PRT
<213> ORGANISM: Artificial Sequence
<220> FEATURE:
<223> OTHER INFORMATION: anti-CD25 L1.17 variable region

<400> SEQUENCE: 61

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Ile Ser Tyr Met
            20                  25                  30

His Trp Phe Gln Gln Lys Pro Gly Gln Ser Pro Gln Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Val Tyr Tyr Cys His Gln Arg Ser Asn Tyr Pro Leu Thr
                85                  90                  95

Phe Gly Ser Gly Thr Lys Leu Glu Ile Lys
            100                 105

<210> SEQ ID NO 62
<211> LENGTH: 106
<212> TYPE: PRT
<213> ORGANISM: Artificial Sequence
<220> FEATURE:
<223> OTHER INFORMATION: anti-CD25 L1.18 variable region

<400> SEQUENCE: 62

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Ile Ser Tyr Met
            20                  25                  30

His Trp Phe Gln Gln Lys Pro Gly Gln Ser Pro Gln Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Val Tyr Tyr Cys His Gln Arg Ser Thr Trp Pro Leu Thr
                85                  90                  95

Phe Gly Ser Gly Thr Lys Leu Glu Ile Lys
            100                 105

<210> SEQ ID NO 63
<211> LENGTH: 107
<212> TYPE: PRT
<213> ORGANISM: Artificial Sequence
<220> FEATURE:
<223> OTHER INFORMATION: anti-CD25 L1.19 variable region

<400> SEQUENCE: 63

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Ile Ser Tyr
            20                  25                  30

Met His Trp Phe Gln Gln Lys Pro Gly Gln Ser Pro Gln Leu Leu Ile
            35                  40                  45

Tyr Thr Thr Ser Asn Leu Ala Ser Gly Val Pro Ala Arg Phe Ser Gly
    50                  55                  60
```

```
Ser Gly Ser Gly Thr Asp Tyr Thr Leu Thr Ile Ser Ser Leu Gln Pro
 65                  70                  75                  80

Glu Asp Phe Ala Val Tyr Tyr Cys His Gln Arg Ser Thr Tyr Pro Leu
                 85                  90                  95

Thr Phe Gly Ser Gly Thr Lys Leu Glu Ile Lys
            100                 105

<210> SEQ ID NO 64
<211> LENGTH: 106
<212> TYPE: PRT
<213> ORGANISM: Artificial Sequence
<220> FEATURE:
<223> OTHER INFORMATION: anti-CD25 L1.20 variable region

<400> SEQUENCE: 64

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Leu
            20                  25                  30

His Trp Tyr Gln Gln Lys Pro Gly Gln Ala Pro Arg Leu Leu Ile Tyr
        35                  40                  45

Thr Thr Ser Asn Arg Ala Thr Gly Ile Pro Ala Arg Phe Ser Gly Ser
    50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys His Gln Arg Ser Thr Tyr Pro Leu Thr
                 85                  90                  95

Phe Gly Ser Gly Thr Lys Leu Glu Ile Lys
            100                 105

<210> SEQ ID NO 65
<211> LENGTH: 106
<212> TYPE: PRT
<213> ORGANISM: Artificial Sequence
<220> FEATURE:
<223> OTHER INFORMATION: anti-CD25 L1.43 variable region

<400> SEQUENCE: 65

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Leu
            20                  25                  30

His Trp Tyr Gln Gln Lys Pro Gly Gln Ala Pro Arg Leu Leu Ile Tyr
        35                  40                  45

Thr Thr Ser Asn Arg Ala Thr Gly Ile Pro Ala Arg Phe Ser Gly Ser
    50                  55                  60

Gly Ser Gly Thr Asp Tyr Thr Leu Thr Ile Ser Ser Leu Gln Pro Glu
 65                  70                  75                  80

Asp Phe Ala Val Tyr Tyr Cys His Gln Arg Ser Thr Tyr Pro Leu Thr
                 85                  90                  95

Phe Gly Ser Gly Thr Lys Leu Glu Ile Lys
            100                 105

<210> SEQ ID NO 66
<211> LENGTH: 106
<212> TYPE: PRT
<213> ORGANISM: Artificial Sequence
<220> FEATURE:
<223> OTHER INFORMATION: anti-CD25 L1.48 variable region
```

```
<400> SEQUENCE: 66

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Thr Thr Ser Asn Arg Ala Thr Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 67
<211> LENGTH: 106
<212> TYPE: PRT
<213> ORGANISM: Artificial Sequence
<220> FEATURE:
<223> OTHER INFORMATION: anti-CD25 L1.56 variable region

<400> SEQUENCE: 67

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Leu
            20                  25                  30

His Trp Phe Gln Gln Lys Pro Gly Gln Ser Pro Gln Leu Leu Ile Tyr
        35                  40                  45

Thr Thr Ser Asn Arg Ala Thr Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 68
<211> LENGTH: 107
<212> TYPE: PRT
<213> ORGANISM: Mus musculus

<400> SEQUENCE: 68

Asp Ile Gln Met Thr Gln Thr Thr Ser Ser Leu Ser Ala Ser Leu Gly
1               5                   10                  15

Asp Arg Val Ile Ile Ser Cys Ser Ala Ser Gln Asp Ile Ser Asn Tyr
            20                  25                  30

Leu Asn Trp Tyr Gln Gln Lys Pro Asp Gly Thr Val Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Val Pro Trp
                85                  90                  95
```

Thr Phe Gly Gly Gly Thr Lys Leu Glu Ile Lys
            100                 105

<210> SEQ ID NO 69
<211> LENGTH: 107
<212> TYPE: PRT
<213> ORGANISM: Artificial Sequence
<220> FEATURE:
<223> OTHER INFORMATION: framework-optimized anti-VEGF (L1)

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 70
<211> LENGTH: 107
<212> TYPE: PRT
<213> ORGANISM: Artificial Sequence
<220> FEATURE:
<223> OTHER INFORMATION: anti-VEGF L1.1 variable region

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Val Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 71
<211> LENGTH: 107
<212> TYPE: PRT
<213> ORGANISM: Artificial Sequence
<220> FEATURE:
<223> OTHER INFORMATION: anti-VEGF L1.2 variable region

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Pro Lys Val Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 72
<211> LENGTH: 107
<212> TYPE: PRT
<213> ORGANISM: Artificial Sequence
<220> FEATURE:
<223> OTHER INFORMATION: anti-VEGF L1.3 variable region

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Leu Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 73
<211> LENGTH: 107
<212> TYPE: PRT
<213> ORGANISM: Artificial Sequence
<220> FEATURE:
<223> OTHER INFORMATION: anti-VEGF L1.4 variable region

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
            35                  40                  45

Tyr Asp Thr Ser Ser Leu His Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 74

-continued

```
<211> LENGTH: 107
<212> TYPE: PRT
<213> ORGANISM: Artificial Sequence
<220> FEATURE:
<223> OTHER INFORMATION: anti-VEGF L1.5 variable region

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
        35                  40                  45

Tyr Phe Ala Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 75
<211> LENGTH: 107
<212> TYPE: PRT
<213> ORGANISM: Artificial Sequence
<220> FEATURE:
<223> OTHER INFORMATION: anti-VEGF L1.6 variable region

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
        35                  40                  45

Tyr Phe Thr Ser Asn Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 76
<211> LENGTH: 107
<212> TYPE: PRT
<213> ORGANISM: Artificial Sequence
<220> FEATURE:
<223> OTHER INFORMATION: anti-VEGF L1.7 variable region

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
        35                  40                  45

Tyr Phe Thr Ser Ser Leu Glu Ser Gly Val Pro Ser Arg Phe Ser Gly
```

```
                 50                  55                  60
Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gly Gly Thr Lys Leu Glu Ile Lys
                100                 105

<210> SEQ ID NO 77
<211> LENGTH: 107
<212> TYPE: PRT
<213> ORGANISM: Artificial Sequence
<220> FEATURE:
<223> OTHER INFORMATION: anti-VEGF L1.8 variable region

<400> SEQUENCE: 77

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Thr Val Lys Val Leu Ile
             35                  40                  45

Tyr Phe Thr Ser Ser Leu His Thr Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gly Gly Thr Lys Leu Glu Ile Lys
                100                 105

<210> SEQ ID NO 78
<211> LENGTH: 107
<212> TYPE: PRT
<213> ORGANISM: Artificial Sequence
<220> FEATURE:
<223> OTHER INFORMATION: anti-VEGF L1.9 variable region

<400> SEQUENCE: 78

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Thr Val Lys Val Leu Ile
             35                  40                  45

Tyr Phe Thr Ser Ser Leu His Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gly Gly Thr Lys Leu Glu Ile Lys
                100                 105

<210> SEQ ID NO 79
<211> LENGTH: 107
<212> TYPE: PRT
<213> ORGANISM: Artificial Sequence
<220> FEATURE:
<223> OTHER INFORMATION: anti-VEGF L1.10 variable region
```

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 80
<211> LENGTH: 107
<212> TYPE: PRT
<213> ORGANISM: Artificial Sequence
<220> FEATURE:
<223> OTHER INFORMATION: anti-VEGF L1.11 variable region

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 81
<211> LENGTH: 107
<212> TYPE: PRT
<213> ORGANISM: Artificial Sequence
<220> FEATURE:
<223> OTHER INFORMATION: anti-VEGF L1.12 variable region

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

```
Glu Asp Phe Ala Thr Tyr Tyr Cys Gln Gln Tyr Asp Thr Val Pro Trp
                85                  90                  95

Thr Phe Gly Gly Gly Thr Lys Leu Glu Ile Lys
            100                 105
```

<210> SEQ ID NO 82
<211> LENGTH: 107
<212> TYPE: PRT
<213> ORGANISM: Artificial Sequence
<220> FEATURE:
<223> OTHER INFORMATION: anti-VEGF L1.13 variable region

<400> SEQUENCE: 82

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Asn Val Pro Trp
                85                  90                  95

Thr Phe Gly Gly Gly Thr Lys Leu Glu Ile Lys
            100                 105
```

<210> SEQ ID NO 83
<211> LENGTH: 107
<212> TYPE: PRT
<213> ORGANISM: Artificial Sequence
<220> FEATURE:
<223> OTHER INFORMATION: anti-VEGF L1.14 variable region

<400> SEQUENCE: 83

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Thr Leu Pro Trp
                85                  90                  95

Thr Phe Gly Gly Gly Thr Lys Leu Glu Ile Lys
            100                 105
```

<210> SEQ ID NO 84
<211> LENGTH: 107
<212> TYPE: PRT
<213> ORGANISM: Artificial Sequence
<220> FEATURE:
<223> OTHER INFORMATION: anti-VEGF L1.15 variable region

<400> SEQUENCE: 84

```
Asp Ile Gln Met Thr Gln Ser Pro Ser Ser Leu Ser Ala Ser Val Gly
1               5                   10                  15
```

-continued

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
        35                  40                  45

Tyr Phe Thr Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 85
<211> LENGTH: 107
<212> TYPE: PRT
<213> ORGANISM: Artificial Sequence
<220> FEATURE:
<223> OTHER INFORMATION: anti-VEGF L1.16 variable region

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Asn Thr Val Pro Trp
                85                  90                  95

Thr Phe Gly Gly Gly Thr Lys Leu Glu Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: anti-VEGF L1.17 variable region

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Thr Val Pro Trp
                85                  90                  95

Thr Phe Gly Gly Gly Thr Lys Leu Glu Ile Lys
            100                 105

```
<210> SEQ ID NO 87
<211> LENGTH: 107
<212> TYPE: PRT
<213> ORGANISM: Artificial Sequence
<220> FEATURE:
<223> OTHER INFORMATION: anti-VEGF L1.18 variable region

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Val Val Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 88
<211> LENGTH: 107
<212> TYPE: PRT
<213> ORGANISM: Artificial Sequence
<220> FEATURE:
<223> OTHER INFORMATION: anti-VEGF L1.19 variable region

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
        35                  40                  45

Tyr Phe Thr Ser Ser Leu Phe Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 89
<211> LENGTH: 107
<212> TYPE: PRT
<213> ORGANISM: Artificial Sequence
<220> FEATURE:
<223> OTHER INFORMATION: anti-VEGF L1.20 variable region

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
```

```
                35                  40                  45
Tyr Phe Thr Ser Ser Leu Ile Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gly Gly Thr Lys Leu Glu Ile Lys
            100                 105

<210> SEQ ID NO 90
<211> LENGTH: 107
<212> TYPE: PRT
<213> ORGANISM: Artificial Sequence
<220> FEATURE:
<223> OTHER INFORMATION: anti-VEGF L1.50 variable region

<400> SEQUENCE: 90

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Val Leu Ile
             35                  40                  45

Tyr Phe Thr Ser Ser Leu His Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Ser Thr Val Pro Trp
                 85                  90                  95

Thr Phe Gly Gly Gly Thr Lys Leu Glu Ile Lys
            100                 105

<210> SEQ ID NO 91
<211> LENGTH: 107
<212> TYPE: PRT
<213> ORGANISM: Artificial Sequence
<220> FEATURE:
<223> OTHER INFORMATION: anti-VEGF L1.51 variable region

<400> SEQUENCE: 91

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Val Leu Ile
             35                  40                  45

Tyr Phe Thr Ser Ser Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Asp Asn Leu Pro Trp
                 85                  90                  95

Thr Phe Gly Gly Gly Thr Lys Leu Glu Ile Lys
            100                 105

<210> SEQ ID NO 92
<211> LENGTH: 107
<212> TYPE: PRT
```

<213> ORGANISM: Artificial Sequence
<220> FEATURE:
<223> OTHER INFORMATION: anti-VEGF L1.52 variable region

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Ala Ser Asn Leu Glu Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 93
<211> LENGTH: 107
<212> TYPE: PRT
<213> ORGANISM: Artificial Sequence
<220> FEATURE:
<223> OTHER INFORMATION: anti-VEGF L1.53 variable region

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Trp
                85                  90                  95

Thr Phe Gly Gly Gly Thr Lys Leu Glu Ile Lys
            100                 105

<210> SEQ ID NO 94
<211> LENGTH: 107
<212> TYPE: PRT
<213> ORGANISM: Artificial Sequence
<220> FEATURE:
<223> OTHER INFORMATION: anti-VEGF L1.54 variable region

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Ala Ser Asn Leu Glu Thr Gly Val Pro Ser Arg Phe Ser Gly
    50                  55                  60

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Ser Thr Val Pro Trp
                 85                  90                  95

Thr Phe Gly Gly Gly Thr Lys Leu Glu Ile Lys
            100                 105

<210> SEQ ID NO 95
<211> LENGTH: 107
<212> TYPE: PRT
<213> ORGANISM: Artificial Sequence
<220> FEATURE:
<223> OTHER INFORMATION: anti-VEGF L1.55 variable region

<400> SEQUENCE: 95

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Val Leu Ile
             35                  40                  45

Tyr Phe Ala Ser Asn Leu Glu Thr Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Asp Asn Leu Pro Trp
                 85                  90                  95

Thr Phe Gly Gly Gly Thr Lys Leu Glu Ile Lys
            100                 105

<210> SEQ ID NO 96
<211> LENGTH: 107
<212> TYPE: PRT
<213> ORGANISM: Artificial Sequence
<220> FEATURE:
<223> OTHER INFORMATION: anti-VEGF L1.56 variable region

<400> SEQUENCE: 96

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Val Leu Ile
             35                  40                  45

Tyr Phe Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Trp
                 85                  90                  95

Thr Phe Gly Gly Gly Thr Lys Leu Glu Ile Lys
            100                 105

<210> SEQ ID NO 97
<211> LENGTH: 107
<212> TYPE: PRT
<213> ORGANISM: Artificial Sequence
<220> FEATURE:
<223> OTHER INFORMATION: anti-VEGF L1.57 variable region

<400> SEQUENCE: 97
```

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Asp Thr Ser Ser Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Trp
                85                  90                  95

Thr Phe Gly Gly Gly Thr Lys Leu Glu Ile Lys
            100                 105
```

<210> SEQ ID NO 98
<211> LENGTH: 107
<212> TYPE: PRT
<213> ORGANISM: Artificial Sequence
<220> FEATURE:
<223> OTHER INFORMATION: anti-VEGF L1.58 variable region

<400> SEQUENCE: 98

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105
```

<210> SEQ ID NO 99
<211> LENGTH: 107
<212> TYPE: PRT
<213> ORGANISM: Artificial Sequence
<220> FEATURE:
<223> OTHER INFORMATION: anti-VEGF L1.59 variable region

<400> SEQUENCE: 99

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Asp Asn Leu Pro Trp
                85                  90                  95
```

```
Thr Phe Gly Gly Gly Thr Lys Leu Glu Ile Lys
            100                 105

<210> SEQ ID NO 100
<211> LENGTH: 107
<212> TYPE: PRT
<213> ORGANISM: Artificial Sequence
<220> FEATURE:
<223> OTHER INFORMATION: anti-VEGF L1.60 variable region

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Trp
                85                  90                  95

Thr Phe Gly Gly Gly Thr Lys Leu Glu Ile Lys
            100                 105

<210> SEQ ID NO 101
<211> LENGTH: 107
<212> TYPE: PRT
<213> ORGANISM: Artificial Sequence
<220> FEATURE:
<223> OTHER INFORMATION: anti-VEGF L1.61 variable region

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Ala Ser Asn Leu Glu Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 102
<211> LENGTH: 107
<212> TYPE: PRT
<213> ORGANISM: Artificial Sequence
<220> FEATURE:
<223> OTHER INFORMATION: anti-VEGF L1.62 variable region

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
```

```
                    20                  25                  30
Leu Asn Trp Tyr Gln Gln Lys Pro Gly Lys Ala Pro Lys Val Leu Ile
            35                  40                  45

Tyr Phe Thr Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 103
<211> LENGTH: 107
<212> TYPE: PRT
<213> ORGANISM: Artificial Sequence
<220> FEATURE:
<223> OTHER INFORMATION: anti-VEGF L1.63 variable region

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile
            35                  40                  45

Tyr Phe Ala Ser Asn Leu Glu Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Trp
                85                  90                  95

Thr Phe Gly Gly Gly Thr Lys Leu Glu Ile Lys
            100                 105

<210> SEQ ID NO 104
<211> LENGTH: 107
<212> TYPE: PRT
<213> ORGANISM: Artificial Sequence
<220> FEATURE:
<223> OTHER INFORMATION: anti-VEGF L1.64 variable region

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile
            35                  40                  45

Tyr Phe Thr Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Trp
                85                  90                  95

Thr Phe Gly Gly Gly Thr Lys Leu Glu Ile Lys
            100                 105
```

```
<210> SEQ ID NO 105
<211> LENGTH: 5
<212> TYPE: PRT
<213> ORGANISM: Artificial Sequence
<220> FEATURE:
<223> OTHER INFORMATION: anti-CD25 heavy chain CDR1

<400> SEQUENCE: 105

Gly Tyr Arg Met His
1               5

<210> SEQ ID NO 106
<211> LENGTH: 5
<212> TYPE: PRT
<213> ORGANISM: Artificial Sequence
<220> FEATURE:
<223> OTHER INFORMATION: anti-CD25 heavy chain CDR1

<400> SEQUENCE: 106

Ser Tyr Arg Met His
1               5

<210> SEQ ID NO 107
<211> LENGTH: 17
<212> TYPE: PRT
<213> ORGANISM: Artificial Sequence
<220> FEATURE:
<223> OTHER INFORMATION: anti-CD25 heavy chain CDR2

<400> SEQUENCE: 107

Trp Ile Asn Pro Asn Ser Gly Gly Thr Asn Tyr Ala Gln Lys Phe Gln
1               5                   10                  15

Gly

<210> SEQ ID NO 108
<211> LENGTH: 17
<212> TYPE: PRT
<213> ORGANISM: Artificial Sequence
<220> FEATURE:
<223> OTHER INFORMATION: anti-CD25 heavy chain CDR2

<400> SEQUENCE: 108

Tyr Ile Asn Pro Asn Ser Gly Gly Thr Asn Tyr Ala Gln Lys Phe Gln
1               5                   10                  15

Gly

<210> SEQ ID NO 109
<211> LENGTH: 17
<212> TYPE: PRT
<213> ORGANISM: Artificial Sequence
<220> FEATURE:
<223> OTHER INFORMATION: anti-CD25 heavy chain CDR2

<400> SEQUENCE: 109

Tyr Ile Asn Pro Ser Thr Gly Tyr Thr Glu Tyr Asn Gln Lys Phe Gln
1               5                   10                  15

Gly

<210> SEQ ID NO 110
<211> LENGTH: 7
<212> TYPE: PRT
<213> ORGANISM: Artificial Sequence
<220> FEATURE:
<223> OTHER INFORMATION: anti-CD25 heavy chain CDR3

<400> SEQUENCE: 110
```

```
Gly Gly Gly Val Phe Asp Tyr
1               5

<210> SEQ ID NO 111
<211> LENGTH: 5
<212> TYPE: PRT
<213> ORGANISM: Artificial Sequence
<220> FEATURE:
<223> OTHER INFORMATION: anti-VEGF heavy chain CDR1

<400> SEQUENCE: 111

Asn Tyr Gly Met Asn
1               5

<210> SEQ ID NO 112
<211> LENGTH: 5
<212> TYPE: PRT
<213> ORGANISM: Artificial Sequence
<220> FEATURE:
<223> OTHER INFORMATION: anti-VEGF heavy chain CDR1

<400> SEQUENCE: 112

Ser Tyr Ala Met Asn
1               5

<210> SEQ ID NO 113
<211> LENGTH: 5
<212> TYPE: PRT
<213> ORGANISM: Artificial Sequence
<220> FEATURE:
<223> OTHER INFORMATION: anti-VEGF heavy chain CDR1

<400> SEQUENCE: 113

Tyr Tyr Ala Met Asn
1               5

<210> SEQ ID NO 114
<211> LENGTH: 17
<212> TYPE: PRT
<213> ORGANISM: Artificial Sequence
<220> FEATURE:
<223> OTHER INFORMATION: anti-VEGF heavy chain CDR2

<400> SEQUENCE: 114

Trp Ile Asn Thr Tyr Thr Gly Glu Pro Thr Tyr Ala Ala Gly Phe Thr
1               5                   10                  15

Gly

<210> SEQ ID NO 115
<211> LENGTH: 17
<212> TYPE: PRT
<213> ORGANISM: Artificial Sequence
<220> FEATURE:
<223> OTHER INFORMATION: anti-VEGF heavy chain CDR2

<400> SEQUENCE: 115

Trp Ile Asn Thr Asn Thr Gly Asn Pro Thr Tyr Ala Gln Gly Phe Thr
1               5                   10                  15

Gly

<210> SEQ ID NO 116
<211> LENGTH: 17
<212> TYPE: PRT
<213> ORGANISM: Artificial Sequence
<220> FEATURE:
<223> OTHER INFORMATION: anti-VEGF heavy chain CDR2
```

```
<400> SEQUENCE: 116

Trp Ile Asn Thr Tyr Thr Gly Asn Pro Thr Tyr Ala Gln Gly Phe Thr
1               5                   10                  15

Gly

<210> SEQ ID NO 117
<211> LENGTH: 14
<212> TYPE: PRT
<213> ORGANISM: Artificial Sequence
<220> FEATURE:
<223> OTHER INFORMATION: anti-VEGF heavy chain CDR3

<400> SEQUENCE: 117

Tyr Pro His Tyr Tyr Gly Ser Ser His Trp Tyr Phe Asp Val
1               5                   10

<210> SEQ ID NO 118
<211> LENGTH: 10
<212> TYPE: PRT
<213> ORGANISM: Artificial Sequence
<220> FEATURE:
<223> OTHER INFORMATION: anti-CD25 light chain CDR1

<400> SEQUENCE: 118

Arg Ala Ser Gln Ser Val Ser Tyr Leu His
1               5                   10

<210> SEQ ID NO 119
<211> LENGTH: 10
<212> TYPE: PRT
<213> ORGANISM: Artificial Sequence
<220> FEATURE:
<223> OTHER INFORMATION: anti-CD25 light chain CDR1

<400> SEQUENCE: 119

Ser Ala Ser Ser Ser Ile Ser Tyr Met His
1               5                   10

<210> SEQ ID NO 120
<211> LENGTH: 10
<212> TYPE: PRT
<213> ORGANISM: Artificial Sequence
<220> FEATURE:
<223> OTHER INFORMATION: anti-CD25 light chain CDR1

<400> SEQUENCE: 120

Arg Ala Ser Ser Ser Ile Ser Tyr Met His
1               5                   10

<210> SEQ ID NO 121
<211> LENGTH: 10
<212> TYPE: PRT
<213> ORGANISM: Artificial Sequence
<220> FEATURE:
<223> OTHER INFORMATION: anti-CD25 light chain CDR1

<400> SEQUENCE: 121

Arg Ala Ser Gln Ser Val Ser Tyr Met His
1               5                   10

<210> SEQ ID NO 122
<211> LENGTH: 7
<212> TYPE: PRT
<213> ORGANISM: Artificial Sequence
<220> FEATURE:
<223> OTHER INFORMATION: anti-CD25 light chain CDR2
```

```
<400> SEQUENCE: 122

Thr Thr Ser Asn Leu Ala Ser
1               5

<210> SEQ ID NO 123
<211> LENGTH: 7
<212> TYPE: PRT
<213> ORGANISM: Artificial Sequence
<220> FEATURE:
<223> OTHER INFORMATION: anti-CD25 light chain CDR2

<400> SEQUENCE: 123

Thr Thr Ser Asn Arg Ala Thr
1               5

<210> SEQ ID NO 124
<211> LENGTH: 9
<212> TYPE: PRT
<213> ORGANISM: Artificial Sequence
<220> FEATURE:
<223> OTHER INFORMATION: anti-CD25 light chain CDR3

<400> SEQUENCE: 124

His Gln Arg Ser Thr Tyr Pro Leu Thr
1               5

<210> SEQ ID NO 125
<211> LENGTH: 11
<212> TYPE: PRT
<213> ORGANISM: Artificial Sequence
<220> FEATURE:
<223> OTHER INFORMATION: anti-VEGF light chain CDR1

<400> SEQUENCE: 125

Gln Ala Ser Gln Asp Ile Ser Asn Tyr Leu Asn
1               5                   10

<210> SEQ ID NO 126
<211> LENGTH: 7
<212> TYPE: PRT
<213> ORGANISM: Artificial Sequence
<220> FEATURE:
<223> OTHER INFORMATION: anti-VEGF light chain CDR2

<400> SEQUENCE: 126

Phe Ala Ser Asn Leu Glu Thr
1               5

<210> SEQ ID NO 127
<211> LENGTH: 7
<212> TYPE: PRT
<213> ORGANISM: Artificial Sequence
<220> FEATURE:
<223> OTHER INFORMATION: anti-VEGF light chain CDR2

<400> SEQUENCE: 127

Phe Thr Ser Ser Leu His Ser
1               5

<210> SEQ ID NO 128
<211> LENGTH: 7
<212> TYPE: PRT
<213> ORGANISM: Artificial Sequence
<220> FEATURE:
<223> OTHER INFORMATION: anti-VEGF light chain CDR2

<400> SEQUENCE: 128
```

```
Asp Thr Ser Ser Leu His Ser
1               5

<210> SEQ ID NO 129
<211> LENGTH: 7
<212> TYPE: PRT
<213> ORGANISM: Artificial Sequence
<220> FEATURE:
<223> OTHER INFORMATION: anti-VEGF light chain CDR2

<400> SEQUENCE: 129

Asp Ala Ser Asn Leu Glu Thr
1               5

<210> SEQ ID NO 130
<211> LENGTH: 7
<212> TYPE: PRT
<213> ORGANISM: Artificial Sequence
<220> FEATURE:
<223> OTHER INFORMATION: anti-VEGF light chain CDR2

<400> SEQUENCE: 130

Phe Ala Ser Asn Leu Glu Ser
1               5

<210> SEQ ID NO 131
<211> LENGTH: 7
<212> TYPE: PRT
<213> ORGANISM: Artificial Sequence
<220> FEATURE:
<223> OTHER INFORMATION: anti-VEGF light chain CDR2

<400> SEQUENCE: 131

Phe Thr Ser Asn Leu Glu Thr
1               5

<210> SEQ ID NO 132
<211> LENGTH: 9
<212> TYPE: PRT
<213> ORGANISM: Artificial Sequence
<220> FEATURE:
<223> OTHER INFORMATION: anti-VEGF light chain CDR3

<400> SEQUENCE: 132

Gln Gln Tyr Ser Thr Val Pro Trp Thr
1               5

<210> SEQ ID NO 133
<211> LENGTH: 9
<212> TYPE: PRT
<213> ORGANISM: Artificial Sequence
<220> FEATURE:
<223> OTHER INFORMATION: anti-VEGF light chain CDR3

<400> SEQUENCE: 133

Gln Gln Tyr Asp Asn Leu Pro Trp Thr
1               5

<210> SEQ ID NO 134
<211> LENGTH: 98
<212> TYPE: PRT
<213> ORGANISM: Artificial Sequence
<220> FEATURE:
<223> OTHER INFORMATION: Framework opt.>

<400> SEQUENCE: 134

Gln Val Gln Leu Val Gln Ser Gly Ala Glu Val Lys Lys Pro Gly Ala
1               5                   10                  15
```

-continued

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Met
        35                  40                  45

Gly Tyr Ile Asn Pro Ser Thr Gly Tyr Thr Glu Tyr Asn Gln Lys Phe
    50                  55                  60

Gln Gly Arg Val Thr Ile Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 135
<211> LENGTH: 98
<212> TYPE: PRT
<213> ORGANISM: Homo sapiens

<400> SEQUENCE: 135

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 136
<211> LENGTH: 98
<212> TYPE: PRT
<213> ORGANISM: Homo sapiens

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 137
<211> LENGTH: 98
<212> TYPE: PRT
<213> ORGANISM: Homo sapiens -continued

<400> SEQUENCE: 137

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Ala Met His Trp Val Arg Gln Ala Pro Gly Gln Arg Leu Glu Trp Met
        35                  40                  45
Gly Trp Ile Asn Ala Gly Asn Gly Asn Thr Lys Tyr Ser Gln Lys Phe
    50                  55                  60
Gln Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg
```

<210> SEQ ID NO 138
<211> LENGTH: 98
<212> TYPE: PRT
<213> ORGANISM: Homo sapiens

<400> SEQUENCE: 138

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Asp Ile Asn Trp Val Arg Gln Ala Thr Gly Gln Gly Leu Glu Trp Met
        35                  40                  45
Gly Trp Met Asn Pro Asn Ser Gly Asn Thr Gly Tyr Ala Gln Lys Phe
    50                  55                  60
Gln Gly Arg Val Thr Met Thr Arg Asn Thr Ser Ile Ser Thr Ala Tyr
65                  70                  75                  80
Met Glu Leu Ser Ser Leu Arg Ser Glu Asp Thr Ala Val Tyr Tyr Cys
                85                  90                  95
Ala Arg
```

<210> SEQ ID NO 139
<211> LENGTH: 98
<212> TYPE: PRT
<213> ORGANISM: Homo sapiens

<400> SEQUENCE: 139

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg
```

<210> SEQ ID NO 140

```
<211> LENGTH: 106
<212> TYPE: PRT
<213> ORGANISM: Artificial Sequence
<220> FEATURE:
<223> OTHER INFORMATION: Framework opt.>

<400> SEQUENCE: 140

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Ile Ser Tyr Met
            20                  25                  30

His Trp Phe Gln Gln Lys Pro Gly Gln Ser Pro Gln Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 141
<211> LENGTH: 107
<212> TYPE: PRT
<213> ORGANISM: Homo sapiens
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid

<400> SEQUENCE: 141

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Xaa
                85                  90                  95

Thr Phe Gly Xaa Gly Thr Lys Xaa Glu Ile Lys
            100                 105

<210> SEQ ID NO 142
<211> LENGTH: 107
<212> TYPE: PRT
<213> ORGANISM: Homo sapiens
<220> FEATURE:
<221> NAME/KEY: misc_feature
<222> LOCATION: (96)..(96)
<223> OTHER INFORMATION: Xaa can be any naturally occurring amino acid
<220> FEATURE:
```

```
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid

<400> SEQUENCE: 142

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His Xaa
                85                  90                  95

Thr Phe Gly Xaa Gly Thr Lys Xaa Glu Ile Lys
            100                 105

<210> SEQ ID NO 143
<211> LENGTH: 108
<212> TYPE: PRT
<213> ORGANISM: Homo sapiens
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid

<400> SEQUENCE: 143

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Xaa Thr Phe Gly Xaa Gly Thr Lys Xaa Glu Ile Lys
            100                 105

<210> SEQ ID NO 144
<211> LENGTH: 107
<212> TYPE: PRT
<213> ORGANISM: Homo sapiens
<220> FEATURE:
<221> NAME/KEY: misc_feature
<222> LOCATION: (96)..(96)
```

-continued

<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid

<400> SEQUENCE: 144

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Xaa
                85                  90                  95

Thr Phe Gly Xaa Gly Thr Lys Xaa Glu Ile Lys
            100                 105

<210> SEQ ID NO 145
<211> LENGTH: 108
<212> TYPE: PRT
<213> ORGANISM: Homo sapiens
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid

<400> SEQUENCE: 145

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Xaa Thr Phe Gly Xaa Gly Thr Lys Xaa Glu Ile Lys
            100                 105

<210> SEQ ID NO 146
<211> LENGTH: 116
<212> TYPE: PRT
<213> ORGANISM: Mus musculus

<400> SEQUENCE: 146

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Arg Met His Trp Val Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Gln Gly Arg Val Thr Ile Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Thr Leu
            100                 105                 110

Thr Val Ser Ser
        115

<210> SEQ ID NO 147
<211> LENGTH: 116
<212> TYPE: PRT
<213> ORGANISM: Artificial Sequence
<220> FEATURE:
<223> OTHER INFORMATION: Framework opt.>

<400> SEQUENCE: 147

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Met
        35                  40                  45

Gly Tyr Ile Asn Pro Ser Thr Gly Tyr Thr Glu Tyr Asn Gln Lys Phe
    50                  55                  60

Gln Gly Arg Val Thr Ile Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115

<210> SEQ ID NO 148
<211> LENGTH: 116
<212> TYPE: PRT
<213> ORGANISM: Homo sapiens
<220> FEATURE:
<221> NAME/KEY: misc_feature
<222> LOCATION: (99)..(101)
<223> OTHER INFORMATION: Xaa can be any naturally occurring amino acid

<400> SEQUENCE: 148

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
            50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Xaa Xaa Xaa Tyr Phe Asp Tyr Trp Gly Gln Gly Thr Leu Val
            100                 105                 110

Thr Val Ser Ser
            115

<210> SEQ ID NO 149
<211> LENGTH: 116
<212> TYPE: PRT
<213> ORGANISM: Artificial Sequence
<220> FEATURE:
<223> OTHER INFORMATION: Anti-CD25 H1.12

<400> SEQUENCE: 149

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Arg Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
            50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
            115

<210> SEQ ID NO 150
<211> LENGTH: 106
<212> TYPE: PRT
<213> ORGANISM: Mus musculus

<400> SEQUENCE: 150

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Ile Ser Tyr Met
            20                  25                  30

His Trp Phe Gln Gln Lys Pro Gly Thr Ser Pro Lys Leu Trp Ile Tyr
            35                  40                  45

Thr Thr Ser Asn Leu Ala Ser Gly Val Pro Ala Arg Phe Ser Gly Ser
            50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys His Gln Arg Ser Thr Tyr Pro Leu Thr
                85                  90                  95

Phe Gly Ser Gly Thr Lys Leu Glu Leu Lys
            100                 105

```
<210> SEQ ID NO 151
<211> LENGTH: 106
<212> TYPE: PRT
<213> ORGANISM: Artificial Sequence
<220> FEATURE:
<223> OTHER INFORMATION: Framework opt.>

<400> SEQUENCE: 151

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ile Ser Tyr Met
            20                  25                  30

His Trp Phe Gln Gln Lys Pro Gly Gln Ser Pro Gln Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 152
<211> LENGTH: 107
<212> TYPE: PRT
<213> ORGANISM: Homo sapiens
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid

<400> SEQUENCE: 152

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Xaa
                85                  90                  95

Thr Phe Gly Xaa Gly Thr Lys Xaa Glu Ile Lys
            100                 105

<210> SEQ ID NO 153
<211> LENGTH: 106
<212> TYPE: PRT
<213> ORGANISM: Artificial Sequence
<220> FEATURE:
<223> OTHER INFORMATION: Anti-CD25 L1.20

<400> SEQUENCE: 153
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Leu
            20                  25                  30

His Trp Tyr Gln Gln Lys Pro Gly Gln Ala Pro Arg Leu Leu Ile Tyr
        35                  40                  45

Thr Thr Ser Asn Arg Ala Thr Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Arg Ser Thr Tyr Pro Leu Thr
                85                  90                  95

Phe Gly Ser Gly Thr Lys Leu Glu Ile Lys
            100                 105

<210> SEQ ID NO 154
<211> LENGTH: 98
<212> TYPE: PRT
<213> ORGANISM: Artificial Sequence
<220> FEATURE:
<223> OTHER INFORMATION: Framework opt.>

<400> SEQUENCE: 154

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Ala Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Lys

<210> SEQ ID NO 155
<211> LENGTH: 98
<212> TYPE: PRT
<213> ORGANISM: Homo sapiens

<400> SEQUENCE: 155

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg
```

<210> SEQ ID NO 156
<211> LENGTH: 98
<212> TYPE: PRT
<213> ORGANISM: Homo sapiens

<400> SEQUENCE: 156

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 157
<211> LENGTH: 98
<212> TYPE: PRT
<213> ORGANISM: Homo sapiens

<400> SEQUENCE: 157

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 158
<211> LENGTH: 98
<212> TYPE: PRT
<213> ORGANISM: Homo sapiens

<400> SEQUENCE: 158

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys

```
                            85                  90                  95

Ala Arg

<210> SEQ ID NO 159
<211> LENGTH: 98
<212> TYPE: PRT
<213> ORGANISM: Homo sapiens

<400> SEQUENCE: 159

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 160
<211> LENGTH: 107
<212> TYPE: PRT
<213> ORGANISM: Artificial Sequence
<220> FEATURE:
<223> OTHER INFORMATION: Framework opt.>
<220> FEATURE:
<221> NAME/KEY: misc_feature
<222> LOCATION: (104)..(104)
<223> OTHER INFORMATION: Xaa can be any naturally occurring amino acid

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Thr Val Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gly Gly Thr Lys Xaa Glu Ile Lys
            100                 105

<210> SEQ ID NO 161
<211> LENGTH: 107
<212> TYPE: PRT
<213> ORGANISM: Homo sapiens
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
```

```
<220> FEATURE:
<221> NAME/KEY: misc_feature
<222> LOCATION: (104)..(104)
<223> OTHER INFORMATION: Xaa can be any naturally occurring amino acid

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Xaa
                85                  90                  95

Thr Phe Gly Xaa Gly Thr Lys Xaa Glu Ile Lys
            100                 105

<210> SEQ ID NO 162
<211> LENGTH: 107
<212> TYPE: PRT
<213> ORGANISM: Homo sapiens
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Xaa
                85                  90                  95

Thr Phe Gly Xaa Gly Thr Lys Xaa Glu Ile Lys
            100                 105

<210> SEQ ID NO 163
<211> LENGTH: 107
<212> TYPE: PRT
<213> ORGANISM: Homo sapiens
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
```

<222> LOCATION: (100)..(100)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Xaa
                85                  90                  95

Thr Phe Gly Xaa Gly Thr Lys Xaa Glu Ile Lys
            100                 105

<210> SEQ ID NO 164
<211> LENGTH: 107
<212> TYPE: PRT
<213> ORGANISM: Homo sapiens
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Xaa
                85                  90                  95

Thr Phe Gly Xaa Gly Thr Lys Xaa Glu Ile Lys
            100                 105

<210> SEQ ID NO 165
<211> LENGTH: 107
<212> TYPE: PRT
<213> ORGANISM: Homo sapiens
<220> FEATURE:
<221> NAME/KEY: misc_feature
<222> LOCATION: (96)..(96)
<223> OTHER INFORMATION: Xaa can be any naturally occurring amino acid

```
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Xaa
                85                  90                  95

Thr Phe Gly Xaa Gly Thr Lys Xaa Glu Ile Lys
            100                 105

<210> SEQ ID NO 166
<211> LENGTH: 121
<212> TYPE: PRT
<213> ORGANISM: Artificial Sequence
<220> FEATURE:
<223> OTHER INFORMATION: Rituximab VH

<400> SEQUENCE: 166

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 167
<211> LENGTH: 106
<212> TYPE: PRT
<213> ORGANISM: Artificial Sequence
<220> FEATURE:
<223> OTHER INFORMATION: Rituximab VL

<400> SEQUENCE: 167

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
```

```
                        20                  25                  30
His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
 50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
                100                 105

<210> SEQ ID NO 168
<211> LENGTH: 119
<212> TYPE: PRT
<213> ORGANISM: Artificial Sequence
<220> FEATURE:
<223> OTHER INFORMATION: Cetuximab VH

<400> SEQUENCE: 168

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
 50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ala
        115

<210> SEQ ID NO 169
<211> LENGTH: 107
<212> TYPE: PRT
<213> ORGANISM: Artificial Sequence
<220> FEATURE:
<223> OTHER INFORMATION: Cetuximab VL

<400> SEQUENCE: 169

Asp Ile Leu Leu Thr Gln Ser Pro Val Ile Leu Ser Val Ser Pro Gly
 1               5                  10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
```

<210> SEQ ID NO 170
<211> LENGTH: 120
<212> TYPE: PRT
<213> ORGANISM: Artificial Sequence
<220> FEATURE:
<223> OTHER INFORMATION: Infliximab VH

<400> SEQUENCE: 170

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser
        115                 120
```

<210> SEQ ID NO 171
<211> LENGTH: 107
<212> TYPE: PRT
<213> ORGANISM: Artificial Sequence
<220> FEATURE:
<223> OTHER INFORMATION: Infliximab VL

<400> SEQUENCE: 171

```
Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys
            100                 105
```

<210> SEQ ID NO 172
<211> LENGTH: 119
<212> TYPE: PRT
<213> ORGANISM: Artificial Sequence
<220> FEATURE:
<223> OTHER INFORMATION: Abciximab VH

<400> SEQUENCE: 172

```
Glu Val Gln Leu Gln Gln Ser Gly Ala Glu Leu Val Lys Pro Gly Ala
1               5                   10                  15
```

```
Ser Val Lys Leu Ser Cys Thr Ala Ser Gly Phe Asn Ile Lys Asp Thr
            20                  25                  30

Tyr Val His Trp Val Lys Gln Arg Pro Glu Gln Gly Leu Glu Trp Ile
            35                  40                  45

Gly Arg Ile Asp Pro Ala Asn Gly Tyr Thr Lys Tyr Asp Pro Lys Phe
 50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Val Arg Pro Leu Tyr Asp Tyr Tyr Ala Met Asp Tyr Trp Gly Gln Gly
                100                 105                 110

Thr Ser Val Thr Val Ser Ser
            115

<210> SEQ ID NO 173
<211> LENGTH: 107
<212> TYPE: PRT
<213> ORGANISM: Artificial Sequence
<220> FEATURE:
<223> OTHER INFORMATION: Abciximab VL

<400> SEQUENCE: 173

Asp Ile Leu Met Thr Gln Ser Pro Ser Ser Met Ser Val Ser Leu Gly
 1               5                  10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Met Gly Leu Ile
            35                  40                  45

Tyr Tyr Gly Thr Asn Leu Val Asp Gly Val Pro Ser Arg Phe Ser Gly
 50                  55                  60

Ser Gly Ser Gly Ala Asp Tyr Ser Leu Thr Ile Ser Ser Leu Asp Ser
 65                  70                  75                  80

Glu Asp Phe Ala Asp Tyr Tyr Cys Val Gln Tyr Ala Gln Leu Pro Tyr
                 85                  90                  95

Thr Phe Gly Gly Gly Thr Lys Leu Glu Ile Lys
                100                 105

<210> SEQ ID NO 174
<211> LENGTH: 117
<212> TYPE: PRT
<213> ORGANISM: Artificial Sequence
<220> FEATURE:
<223> OTHER INFORMATION: Basiliximab VH

<400> SEQUENCE: 174

Glu Val Gln Leu Gln Gln Ser Gly Thr Val Leu Ala Arg Pro Gly Ala
 1               5                  10                  15

Ser Val Lys Met Ser Cys Lys Ala Ser Gly Tyr Ser Phe Thr Arg Tyr
            20                  25                  30

Trp Met His Trp Ile Lys Gln Arg Pro Gly Gln Gly Leu Glu Trp Ile
            35                  40                  45

Gly Ala Ile Tyr Pro Gly Asn Ser Asp Thr Ser Tyr Asn Gln Lys Phe
 50                  55                  60

Glu Gly Lys Ala Lys Leu Thr Ala Val Thr Ser Ala Ser Thr Ala Tyr
 65                  70                  75                  80

Met Glu Leu Ser Ser Leu Thr His Glu Asp Ser Ala Val Tyr Tyr Cys
                 85                  90                  95
```

```
Ser Arg Asp Tyr Gly Tyr Tyr Phe Asp Phe Trp Gly Gln Gly Thr Thr
            100                 105                 110

Leu Thr Val Ser Ser
        115

<210> SEQ ID NO 175
<211> LENGTH: 104
<212> TYPE: PRT
<213> ORGANISM: Artificial Sequence
<220> FEATURE:
<223> OTHER INFORMATION: Basiliximab VL

<400> SEQUENCE: 175

Gln Ile Val Ser Thr Gln Ser Pro Ala Ile Met Ser Ala Ser Pro Gly
1               5                   10                  15

Glu Lys Val Thr Met Thr Cys Ser Ala Ser Ser Arg Ser Tyr Met
            20                  25                  30

Gln Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Thr Phe Gly
                85                  90                  95

Gly Gly Thr Lys Leu Glu Ile Lys
            100

<210> SEQ ID NO 176
<211> LENGTH: 121
<212> TYPE: PRT
<213> ORGANISM: Artificial Sequence
<220> FEATURE:
<223> OTHER INFORMATION: Ibritumomab VH

<400> SEQUENCE: 176

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 177
<211> LENGTH: 106
<212> TYPE: PRT
<213> ORGANISM: Artificial Sequence
<220> FEATURE:
<223> OTHER INFORMATION: Ibritumomab VL

<400> SEQUENCE: 177
```

```
Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Val Ser Tyr Ile
                20                  25                  30

His Trp Phe Gln Gln Lys Pro Gly Ser Ser Pro Lys Pro Trp Ile Tyr
                35                  40                  45

Ala Thr Ser Asn Leu Ala Ser Gly Val Pro Val Arg Phe Ser Gly Ser
            50                  55                  60

Gly Ser Gly Thr Ser Tyr Ser Leu Thr Ile Ser Arg Val Glu Ala Glu
 65                 70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 178
<211> LENGTH: 122
<212> TYPE: PRT
<213> ORGANISM: Artificial Sequence
<220> FEATURE:
<223> OTHER INFORMATION: Tositumomab VH

<400> SEQUENCE: 178

Gln Ala Tyr Leu Gln Gln Ser Gly Ala Glu Leu Val Arg Pro Gly Ala
 1               5                  10                  15

Ser Val Lys Met Ser Cys Lys Ala Ser Gly Tyr Thr Phe Thr Ser Tyr
                20                  25                  30

Asn Met His Trp Val Lys Gln Thr Pro Arg Gln Gly Leu Glu Trp Ile
                35                  40                  45

Gly Ala Ile Tyr Pro Gly Asn Gly Asp Thr Ser Tyr Asn Gln Lys Phe
            50                  55                  60

Lys Gly Lys Ala Thr Leu Thr Val Asp Lys Ser Ser Ser Thr Ala Tyr
 65                 70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
                100                 105                 110

Gly Thr Gly Thr Thr Val Thr Val Ser Gly
            115                 120

<210> SEQ ID NO 179
<211> LENGTH: 106
<212> TYPE: PRT
<213> ORGANISM: Artificial Sequence
<220> FEATURE:
<223> OTHER INFORMATION: Tositumomab VL

<400> SEQUENCE: 179

Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Val Ser Tyr Met
                20                  25                  30

His Trp Tyr Gln Gln Lys Pro Gly Ser Ser Pro Lys Pro Trp Ile Tyr
                35                  40                  45

Ala Pro Ser Asn Leu Ala Ser Gly Val Pro Ala Arg Phe Ser Gly Ser
            50                  55                  60

Gly Ser Gly Thr Ser Tyr Ser Leu Thr Ile Ser Arg Val Glu Ala Glu
 65                 70                  75                  80
```

Asp Ala Ala Thr Tyr Tyr Cys Gln Gln Trp Ser Phe Asn Pro Pro Thr
            85                  90                  95

Phe Gly Ala Gly Thr Lys Leu Glu Leu Lys
            100                 105

<210> SEQ ID NO 180
<211> LENGTH: 119
<212> TYPE: PRT
<213> ORGANISM: Artificial Sequence
<220> FEATURE:
<223> OTHER INFORMATION: Muromonab VH

<400> SEQUENCE: 180

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 181
<211> LENGTH: 106
<212> TYPE: PRT
<213> ORGANISM: Artificial Sequence
<220> FEATURE:
<223> OTHER INFORMATION: Muromonab VL

<400> SEQUENCE: 181

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105

<210> SEQ ID NO 182
<211> LENGTH: 114
<212> TYPE: PRT
<213> ORGANISM: Artificial Sequence
<220> FEATURE:
<223> OTHER INFORMATION: Satumomab VH -continued

<400> SEQUENCE: 182

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Ala Lys Gln Lys Pro Glu Gln Gly Leu Glu Trp Ile
        35                  40                  45

Gly Tyr Ile Ser Pro Gly Asn Asp Asp Ile Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Tyr Tyr Gly His Trp Gly Gln Gly Thr Thr Leu Thr Val
            100                 105                 110

Ser Ser

<210> SEQ ID NO 183
<211> LENGTH: 107
<212> TYPE: PRT
<213> ORGANISM: Artificial Sequence
<220> FEATURE:
<223> OTHER INFORMATION: Satumomab VL

<400> SEQUENCE: 183

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Arg Leu Glu Ile Lys
            100                 105

<210> SEQ ID NO 184
<211> LENGTH: 121
<212> TYPE: PRT
<213> ORGANISM: Artificial Sequence
<220> FEATURE:
<223> OTHER INFORMATION: Arcitumomab VH

<400> SEQUENCE: 184

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Asn Trp Val Arg Gln Pro Pro Gly Lys Ala Leu Glu Trp Leu
        35                  40                  45

Gly Phe Ile Gly Asn Lys Ala Asn Gly Tyr Thr Thr Glu Tyr Ser Ala
    50                  55                  60

Ser Val Lys Gly Arg Phe Thr Ile Ser Arg Asp Lys Ser Gln Ser Ile
65                  70                  75                  80

```
Leu Tyr Leu Gln Met Asn Thr Leu Arg Ala Glu Asp Ser Ala Thr Tyr
                85                  90                  95

Tyr Cys Thr Arg Asp Arg Gly Leu Arg Phe Tyr Phe Asp Tyr Trp Gly
            100                 105                 110

Gln Gly Thr Thr Leu Thr Val Ser Ser
        115                 120

<210> SEQ ID NO 185
<211> LENGTH: 106
<212> TYPE: PRT
<213> ORGANISM: Artificial Sequence
<220> FEATURE:
<223> OTHER INFORMATION: Arcitumomab VL

<400> SEQUENCE: 185

Gln Thr Val Leu Ser Gln Ser Pro Ala Ile Leu Ser Ala Ser Pro Gly
1               5                   10                  15

Glu Lys Val Thr Met Thr Cys Arg Ala Ser Ser Val Thr Tyr Ile
            20                  25                  30

His Trp Tyr Gln Gln Lys Pro Gly Ser Ser Pro Lys Ser Trp Ile Tyr
            35                  40                  45

Ala Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln His Trp Ser Ser Lys Pro Pro Thr
                85                  90                  95

Phe Gly Gly Gly Thr Lys Leu Glu Ile Lys
            100                 105

<210> SEQ ID NO 186
<211> LENGTH: 121
<212> TYPE: PRT
<213> ORGANISM: Artificial Sequence
<220> FEATURE:
<223> OTHER INFORMATION: Alemtuzumab VH

<400> SEQUENCE: 186

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Asp Phe
            20                  25                  30

Tyr Met Asn Trp Val Arg Gln Pro Pro Gly Arg Gly Leu Glu Trp Ile
            35                  40                  45

Gly Phe Ile Arg Asp Lys Ala Lys Gly Tyr Thr Thr Glu Tyr Asn Pro
        50                  55                  60

Ser Val Lys Gly Arg Val Thr Met Leu Val Asp Thr Ser Lys Asn Gln
65                  70                  75                  80

Phe Ser Leu Arg Leu Ser Ser Val Thr Ala Ala Asp Thr Ala Val Tyr
                85                  90                  95

Tyr Cys Ala Arg Glu Gly His Thr Ala Ala Pro Phe Tyr Trp Gly
            100                 105                 110

Gln Gly Ser Leu Val Thr Val Ser Ser
        115                 120

<210> SEQ ID NO 187
<211> LENGTH: 107
<212> TYPE: PRT
<213> ORGANISM: Artificial Sequence
```

```
<220> FEATURE:
<223> OTHER INFORMATION: Alemtuzumab VL

<400> SEQUENCE: 187

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys
            100                 105

<210> SEQ ID NO 188
<211> LENGTH: 123
<212> TYPE: PRT
<213> ORGANISM: Artificial Sequence
<220> FEATURE:
<223> OTHER INFORMATION: Bevacizumab VH

<400> SEQUENCE: 188

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 189
<211> LENGTH: 107
<212> TYPE: PRT
<213> ORGANISM: Artificial Sequence
<220> FEATURE:
<223> OTHER INFORMATION: Bevacizumab VL

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
```

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys
                100                 105

<210> SEQ ID NO 190
<211> LENGTH: 118
<212> TYPE: PRT
<213> ORGANISM: Artificial Sequence
<220> FEATURE:
<223> OTHER INFORMATION: Certolizumab VH

<400> SEQUENCE: 190

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Val Phe Thr Asp Tyr
                20                  25                  30

Gly Met Asn Trp Val Arg Gln Ala Pro Gly Lys Gly Leu Glu Trp Met
             35                  40                  45

Gly Trp Ile Asn Thr Tyr Ile Gly Glu Pro Ile Tyr Ala Asp Ser Val
 50                  55                  60

Lys Gly Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Arg Ser Tyr Ala Met Asp Tyr Trp Gly Gln Gly Thr
                100                 105                 110

Leu Val Thr Val Ser Ser
        115

<210> SEQ ID NO 191
<211> LENGTH: 107
<212> TYPE: PRT
<213> ORGANISM: Artificial Sequence
<220> FEATURE:
<223> OTHER INFORMATION: Certolizumab VL

<400> SEQUENCE: 191

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Val Gly Thr Asn
                20                  25                  30

Val Ala Trp Tyr Gln Gln Lys Pro Gly Lys Ala Pro Lys Ala Leu Ile
             35                  40                  45

Tyr Ser Ala Ser Phe Leu Tyr Ser Gly Val Pro Tyr Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ile Tyr Pro Leu
                 85                  90                  95

Thr Phe Gly Gln Gly Thr Lys Val Glu Ile Lys
                100                 105

<210> SEQ ID NO 192
<211> LENGTH: 116
<212> TYPE: PRT
```

```
<213> ORGANISM: Artificial Sequence
<220> FEATURE:
<223> OTHER INFORMATION: Daclizumab VH

<400> SEQUENCE: 192

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115

<210> SEQ ID NO 193
<211> LENGTH: 106
<212> TYPE: PRT
<213> ORGANISM: Artificial Sequence
<220> FEATURE:
<223> OTHER INFORMATION: Daclizumab VL

<400> SEQUENCE: 193

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys His Gln Arg Ser Thr Tyr Pro Leu Thr
                85                  90                  95

Phe Gly Gln Gly Thr Lys Val Glu Val Lys
            100                 105

<210> SEQ ID NO 194
<211> LENGTH: 122
<212> TYPE: PRT
<213> ORGANISM: Artificial Sequence
<220> FEATURE:
<223> OTHER INFORMATION: Eculizumab VH

<400> SEQUENCE: 194

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45
```

```
Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
            115                 120

<210> SEQ ID NO 195
<211> LENGTH: 107
<212> TYPE: PRT
<213> ORGANISM: Artificial Sequence
<220> FEATURE:
<223> OTHER INFORMATION: Eculizumab VL (

<400> SEQUENCE: 195

Asp Ile Gln Met Thr Gln Ser Pro Ser Ser Leu Ser Ala Ser Val Gly
 1               5                  10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Asn Val Leu Asn Thr Pro Leu
                 85                  90                  95

Thr Phe Gly Gln Gly Thr Lys Val Glu Ile Lys
            100                 105

<210> SEQ ID NO 196
<211> LENGTH: 121
<212> TYPE: PRT
<213> ORGANISM: Artificial Sequence
<220> FEATURE:
<223> OTHER INFORMATION: Efalizumab VH

<400> SEQUENCE: 196

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Phe Thr Gly His
            20                  25                  30

Trp Met Asn Trp Val Arg Gln Ala Pro Gly Lys Gly Leu Glu Trp Val
        35                  40                  45

Gly Met Ile His Pro Ser Asp Ser Glu Thr Arg Tyr Asn Gln Lys Phe
    50                  55                  60

Lys Asp Arg Phe Thr Ile Ser Val Asp Lys Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ile Tyr Phe Tyr Gly Thr Thr Tyr Phe Asp Tyr Trp Gly
            100                 105                 110

Gln Gly Thr Leu Val Thr Val Ser Ser
            115                 120
```

-continued

```
<210> SEQ ID NO 197
<211> LENGTH: 107
<212> TYPE: PRT
<213> ORGANISM: Artificial Sequence
<220> FEATURE:
<223> OTHER INFORMATION: Efalizumab VL

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Thr Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Phe Tyr Tyr Cys Gln Gln His Asn Glu Tyr Pro Leu
                85                  90                  95

Thr Phe Gly Gln Gly Thr Lys Val Glu Ile Lys
            100                 105

<210> SEQ ID NO 198
<211> LENGTH: 116
<212> TYPE: PRT
<213> ORGANISM: Artificial Sequence
<220> FEATURE:
<223> OTHER INFORMATION: Gemtuzumab VH

<400> SEQUENCE: 198

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser
        115

<210> SEQ ID NO 199
<211> LENGTH: 111
<212> TYPE: PRT
<213> ORGANISM: Artificial Sequence
<220> FEATURE:
<223> OTHER INFORMATION: Gemtuzumab VL

<400> SEQUENCE: 199

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30
```

```
Gly Ile Ser Phe Met Asn Trp Phe Gln Gln Lys Pro Gly Gly Ala Pro
            35                  40                  45

Lys Leu Leu Ile Tyr Ala Ala Ser Asn Gln Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Asp Asp Phe Ala Thr Tyr Tyr Cys Gln Gln Ser Lys
             85                  90                  95

Glu Val Pro Trp Thr Phe Gly Gln Gly Thr Lys Val Glu Ile Lys
            100                 105                 110

<210> SEQ ID NO 200
<211> LENGTH: 120
<212> TYPE: PRT
<213> ORGANISM: Artificial Sequence
<220> FEATURE:
<223> OTHER INFORMATION: Motavizumab VH

<400> SEQUENCE: 200

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys His Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
             85                  90                  95

Cys Ala Arg Asp Met Ile Phe Asn Phe Tyr Phe Asp Val Trp Gly Gln
            100                 105                 110

Gly Thr Thr Val Thr Val Ser Ser
            115                 120

<210> SEQ ID NO 201
<211> LENGTH: 106
<212> TYPE: PRT
<213> ORGANISM: Artificial Sequence
<220> FEATURE:
<223> OTHER INFORMATION: Motavizumab VL

<400> SEQUENCE: 201

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Arg Val Gly Tyr Met
             20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
             85                  90                  95

Phe Gly Gly Gly Thr Lys Val Glu Ile Lys
            100                 105
```

```
<210> SEQ ID NO 202
<211> LENGTH: 123
<212> TYPE: PRT
<213> ORGANISM: Artificial Sequence
<220> FEATURE:
<223> OTHER INFORMATION: Natalizumab VH

<400> SEQUENCE: 202

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Arg Leu Glu Trp Met
        35                  40                  45

Gly Arg Ile Asp Pro Ala Asn Gly Tyr Thr Lys Tyr Asp Pro Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Asn Tyr Gly Val Tyr Ala Met Asp Tyr
            100                 105                 110

Trp Gly Gln Gly Thr Leu Val Thr Val Ser Ser
        115                 120

<210> SEQ ID NO 203
<211> LENGTH: 106
<212> TYPE: PRT
<213> ORGANISM: Artificial Sequence
<220> FEATURE:
<223> OTHER INFORMATION: Natalizumab VL

<400> SEQUENCE: 203

Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asp Ile Asn Lys Tyr
            20                  25                  30

Met Ala Trp Tyr Gln Gln Thr Pro Gly Lys Ala Pro Arg Leu Leu Ile
        35                  40                  45

His Tyr Thr Ser Ala Leu Gln Pro Gly Ile Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Trp Thr
                85                  90                  95

Phe Gly Gln Gly Thr Lys Val Glu Ile Lys
            100                 105

<210> SEQ ID NO 204
<211> LENGTH: 121
<212> TYPE: PRT
<213> ORGANISM: Artificial Sequence
<220> FEATURE:
<223> OTHER INFORMATION: Omalizumab VH

<400> SEQUENCE: 204

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
```

-continued

```
                20                  25                  30
Tyr Ser Trp Asn Trp Ile Arg Gln Ala Pro Gly Lys Gly Leu Glu Trp
            35                  40                  45
Val Ala Ser Ile Thr Tyr Asp Gly Ser Thr Asn Tyr Ala Asp Ser Val
 50                  55                  60
Lys Gly Arg Phe Thr Ile Ser Arg Asp Asp Ser Lys Asn Thr Phe Tyr
 65                  70                  75                  80
Leu Gln Met Asn Ser Leu Arg Ala Glu Asp Thr Ala Val Tyr Tyr Cys
                85                  90                  95
Ala Arg Gly Ser His Tyr Phe Gly His Trp His Phe Ala Val Trp Gly
            100                 105                 110
Gln Gly Thr Leu Val Thr Val Ser Ser
            115                 120

<210> SEQ ID NO 205
<211> LENGTH: 111
<212> TYPE: PRT
<213> ORGANISM: Artificial Sequence
<220> FEATURE:
<223> OTHER INFORMATION: Omalizumab VL

<400> SEQUENCE: 205

Asp Ile Gln Leu Thr Gln Ser Pro Ser Ser Leu Ser Ala Ser Val Gly
 1               5                  10                  15
Asp Arg Val Thr Ile Thr Cys Arg Ala Ser Gln Ser Val Asp Tyr Asp
            20                  25                  30
Gly Asp Ser Tyr Met Asn Trp Tyr Gln Gln Lys Pro Gly Lys Ala Pro
            35                  40                  45
Lys Leu Leu Ile Tyr Ala Ala Ser Tyr Leu Glu Ser Gly Val Pro Ser
 50                  55                  60
Arg Phe Ser Gly Ser Gly Ser Gly Thr Asp Phe Thr Leu Thr Ile Ser
 65                  70                  75                  80
Ser Leu Gln Pro Glu Asp Phe Ala Thr Tyr Tyr Cys Gln Gln Ser His
                85                  90                  95
Glu Asp Pro Tyr Thr Phe Gly Gly Gly Thr Lys Val Glu Ile Lys
            100                 105                 110

<210> SEQ ID NO 206
<211> LENGTH: 120
<212> TYPE: PRT
<213> ORGANISM: Artificial Sequence
<220> FEATURE:
<223> OTHER INFORMATION: Palivizumab VH

<400> SEQUENCE: 206

Gln Val Thr Leu Arg Glu Ser Gly Pro Ala Leu Val Lys Pro Thr Gln
 1               5                  10                  15
Thr Leu Thr Leu Thr Cys Thr Phe Ser Gly Phe Ser Leu Ser Thr Ser
            20                  25                  30
Gly Met Ser Val Gly Trp Ile Arg Gln Pro Pro Gly Lys Ala Leu Glu
            35                  40                  45
Trp Leu Ala Asp Ile Trp Trp Asp Asp Lys Lys Asp Tyr Asn Pro Ser
 50                  55                  60
Leu Lys Ser Arg Leu Thr Ile Ser Lys Asp Thr Ser Lys Asn Gln Val
 65                  70                  75                  80
Val Leu Lys Val Thr Asn Met Asp Pro Ala Asp Thr Ala Thr Tyr Tyr
                85                  90                  95
Cys Ala Arg Ser Met Ile Thr Asn Trp Tyr Phe Asp Val Trp Gly Ala
```

```
                    100                 105                 110

Gly Thr Thr Val Thr Val Ser Ser
        115                 120

<210> SEQ ID NO 207
<211> LENGTH: 106
<212> TYPE: PRT
<213> ORGANISM: Artificial Sequence
<220> FEATURE:
<223> OTHER INFORMATION: Palivizumab VL

<400> SEQUENCE: 207

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 208
<211> LENGTH: 123
<212> TYPE: PRT
<213> ORGANISM: Artificial Sequence
<220> FEATURE:
<223> OTHER INFORMATION: Ranibizumab VH

<400> SEQUENCE: 208

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser
        115                 120

<210> SEQ ID NO 209
<211> LENGTH: 107
<212> TYPE: PRT
<213> ORGANISM: Artificial Sequence
<220> FEATURE:
<223> OTHER INFORMATION: Ranibizumab VL

<400> SEQUENCE: 209
```

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 210
<211> LENGTH: 120
<212> TYPE: PRT
<213> ORGANISM: Artificial Sequence
<220> FEATURE:
<223> OTHER INFORMATION: Tocilizumab VH

<400> SEQUENCE: 210

```
Gln Val Thr Leu Arg Glu Ser Gly Pro Ala Leu Val Arg Pro Thr Gln
1               5                   10                  15

Thr Leu Thr Leu Thr Cys Thr Phe Ser Gly Phe Ser Leu Ser Thr Ser
            20                  25                  30

Gly Met Thr Val Gly Trp Ile Arg Gln Pro Pro Gly Glu Ala Leu Glu
        35                  40                  45

Trp Leu Ala His Ile Trp Trp Asn Asp Asp Lys Tyr Tyr Asn Pro Ala
    50                  55                  60

Leu Gly Lys Arg Leu Ala Val Ser Lys Asp Thr Ser Lys Asn Gln Val
65              70                  75                  80

Val Leu Ser Met Asn Thr Val Gly Pro Gly Asp Thr Ala Thr Tyr Tyr
                85                  90                  95

Cys Ala Arg Met Glu Asp Tyr Asp Glu Ala Met Asp Tyr Trp Gly Gln
            100                 105                 110

Gly Ile Leu Val Thr Val Ser Ser
        115                 120
```

<210> SEQ ID NO 211
<211> LENGTH: 106
<212> TYPE: PRT
<213> ORGANISM: Artificial Sequence
<220> FEATURE:
<223> OTHER INFORMATION: Tocilizumab VL

<400> SEQUENCE: 211

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Tyr Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65              70                  75                  80
```

```
Glu Asp Ile Ala Thr Tyr Tyr Cys Gln Arg Phe Trp Gly Thr Pro Pro
                85                  90                  95

Phe Gly Gln Gly Thr Lys Val Glu Ile Lys
            100                 105

<210> SEQ ID NO 212
<211> LENGTH: 120
<212> TYPE: PRT
<213> ORGANISM: Artificial Sequence
<220> FEATURE:
<223> OTHER INFORMATION: Trastuzumab VH

<400> SEQUENCE: 212

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 213
<211> LENGTH: 107
<212> TYPE: PRT
<213> ORGANISM: Artificial Sequence
<220> FEATURE:
<223> OTHER INFORMATION: Trastuzumab VL

<400> SEQUENCE: 213

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 214
<211> LENGTH: 120
<212> TYPE: PRT
<213> ORGANISM: Artificial Sequence
<220> FEATURE:
<223> OTHER INFORMATION: anti-TNF H0 variable region (A2; infliximab)

<400> SEQUENCE: 214
```

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser
            115             120
```

<210> SEQ ID NO 215
<211> LENGTH: 120
<212> TYPE: PRT
<213> ORGANISM: Artificial Sequence
<220> FEATURE:
<223> OTHER INFORMATION: framework-optimized anti-TNF variable region
      (H1)

<400> SEQUENCE: 215

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
            20                  25                  30

Trp Met Asn Trp Val Arg Gln Ala Ser Gly Lys Gly Leu Glu Trp Val
        35                  40                  45

Gly Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
            115             120
```

<210> SEQ ID NO 216
<211> LENGTH: 120
<212> TYPE: PRT
<213> ORGANISM: Artificial Sequence
<220> FEATURE:
<223> OTHER INFORMATION: anti-TNF H1.1 variable region

<400> SEQUENCE: 216

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn His
            20                  25                  30

Trp Met Asn Trp Val Arg Gln Ala Ser Gly Lys Gly Leu Glu Trp Val
        35                  40                  45

Gly Glu Ile Arg Ser Lys Ser Ile Asn Ser Ala Thr His Tyr Ala Glu
```

```
                    50                  55                  60
Ser Val Lys Gly Arg Phe Thr Ile Ser Arg Asp Asp Ser Lys Ser Ile
 65                  70                  75                  80

Val Tyr Leu Gln Met Asn Ser Leu Lys Thr Glu Asp Thr Ala Val Tyr
                     85                  90                  95

Tyr Cys Ser Arg Asn Tyr Tyr Gly Ser Thr Tyr Asp Tyr Trp Gly Gln
                    100                 105                 110

Gly Thr Leu Val Thr Val Ser Ser
                115                 120

<210> SEQ ID NO 217
<211> LENGTH: 120
<212> TYPE: PRT
<213> ORGANISM: Artificial Sequence
<220> FEATURE:
<223> OTHER INFORMATION: anti-TNF H1.2 variable region

<400> SEQUENCE: 217

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Ile Phe Ser Gly His
                 20                  25                  30

Trp Met Asn Trp Val Arg Gln Ala Ser Gly Lys Gly Leu Glu Trp Val
             35                  40                  45

Gly Glu Ile Arg Ser Lys Ser Ile Asn Ser Ala Thr His Tyr Ala Glu
         50                  55                  60

Ser Val Lys Gly Arg Phe Thr Ile Ser Arg Asp Asp Ser Lys Ser Ile
 65                  70                  75                  80

Val Tyr Leu Gln Met Asn Ser Leu Lys Thr Glu Asp Thr Ala Val Tyr
                     85                  90                  95

Tyr Cys Ser Arg Asn Tyr Tyr Gly Ser Thr Tyr Asp Tyr Trp Gly Gln
                    100                 105                 110

Gly Thr Leu Val Thr Val Ser Ser
                115                 120

<210> SEQ ID NO 218
<211> LENGTH: 120
<212> TYPE: PRT
<213> ORGANISM: Artificial Sequence
<220> FEATURE:
<223> OTHER INFORMATION: anti-TNF H1.3 variable region

<400> SEQUENCE: 218

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Ile Phe Ser Asn Ser
                 20                  25                  30

Trp Met Asn Trp Val Arg Gln Ala Ser Gly Lys Gly Leu Glu Trp Val
             35                  40                  45

Gly Glu Ile Arg Ser Lys Ser Ile Asn Ser Ala Thr His Tyr Ala Glu
         50                  55                  60

Ser Val Lys Gly Arg Phe Thr Ile Ser Arg Asp Asp Ser Lys Ser Ile
 65                  70                  75                  80

Val Tyr Leu Gln Met Asn Ser Leu Lys Thr Glu Asp Thr Ala Val Tyr
                     85                  90                  95

Tyr Cys Ser Arg Asn Tyr Tyr Gly Ser Thr Tyr Asp Tyr Trp Gly Gln
                    100                 105                 110

Gly Thr Leu Val Thr Val Ser Ser
```

```
            115                 120

<210> SEQ ID NO 219
<211> LENGTH: 120
<212> TYPE: PRT
<213> ORGANISM: Artificial Sequence
<220> FEATURE:
<223> OTHER INFORMATION: anti-TNF H1.4 variable region

<400> SEQUENCE: 219

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
            20                  25                  30

Ala Met Asn Trp Val Arg Gln Ala Ser Gly Lys Gly Leu Glu Trp Val
        35                  40                  45

Gly Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
            115                 120

<210> SEQ ID NO 220
<211> LENGTH: 120
<212> TYPE: PRT
<213> ORGANISM: Artificial Sequence
<220> FEATURE:
<223> OTHER INFORMATION: anti-TNF H1.5 variable region

<400> SEQUENCE: 220

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
            20                  25                  30

Trp Met His Trp Val Arg Gln Ala Ser Gly Lys Gly Leu Glu Trp Val
        35                  40                  45

Gly Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
            115                 120

<210> SEQ ID NO 221
<211> LENGTH: 120
<212> TYPE: PRT
<213> ORGANISM: Artificial Sequence
<220> FEATURE:
<223> OTHER INFORMATION: anti-TNF H1.6 variable region

<400> SEQUENCE: 221
```

-continued

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
            20                  25                  30

Trp Met Asn Trp Val Arg Gln Ala Ser Gly Lys Gly Leu Glu Trp Val
        35                  40                  45

Gly Arg Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
        115                 120

<210> SEQ ID NO 222
<211> LENGTH: 120
<212> TYPE: PRT
<213> ORGANISM: Artificial Sequence
<220> FEATURE:
<223> OTHER INFORMATION: anti-TNF H1.7 variable region

<400> SEQUENCE: 222

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
            20                  25                  30

Trp Met Asn Trp Val Arg Gln Ala Ser Gly Lys Gly Leu Glu Trp Val
        35                  40                  45

Gly Glu Ile Arg Ser Lys Ala Ile Asn Ser Ala Thr His Tyr Ala Glu
    50                  55                  60

Ser Val Lys Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
        115                 120

<210> SEQ ID NO 223
<211> LENGTH: 120
<212> TYPE: PRT
<213> ORGANISM: Artificial Sequence
<220> FEATURE:
<223> OTHER INFORMATION: anti-TNF H1.8 variable region

<400> SEQUENCE: 223

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
            20                  25                  30

Trp Met Asn Trp Val Arg Gln Ala Ser Gly Lys Gly Leu Glu Trp Val
        35                  40                  45

Gly Glu Ile Arg Ser Lys Ser Asn Asn Ser Ala Thr His Tyr Ala Glu
    50                  55                  60

```
Ser Val Lys Gly Arg Phe Thr Ile Ser Arg Asp Asp Ser Lys Ser Ile
 65                  70                  75                  80

Val Tyr Leu Gln Met Asn Ser Leu Lys Thr Glu Asp Thr Ala Val Tyr
                 85                  90                  95

Tyr Cys Ser Arg Asn Tyr Tyr Gly Ser Thr Tyr Asp Tyr Trp Gly Gln
                100                 105                 110

Gly Thr Leu Val Thr Val Ser Ser
            115                 120

<210> SEQ ID NO 224
<211> LENGTH: 120
<212> TYPE: PRT
<213> ORGANISM: Artificial Sequence
<220> FEATURE:
<223> OTHER INFORMATION: anti-TNF H1.9 variable region

<400> SEQUENCE: 224

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
                20                  25                  30

Trp Met Asn Trp Val Arg Gln Ala Ser Gly Lys Gly Leu Glu Trp Val
             35                  40                  45

Gly Glu Ile Arg Ser Lys Ser Ile Ser Ser Ala Thr His Tyr Ala Glu
         50                  55                  60

Ser Val Lys Gly Arg Phe Thr Ile Ser Arg Asp Asp Ser Lys Ser Ile
 65                  70                  75                  80

Val Tyr Leu Gln Met Asn Ser Leu Lys Thr Glu Asp Thr Ala Val Tyr
                 85                  90                  95

Tyr Cys Ser Arg Asn Tyr Tyr Gly Ser Thr Tyr Asp Tyr Trp Gly Gln
                100                 105                 110

Gly Thr Leu Val Thr Val Ser Ser
            115                 120

<210> SEQ ID NO 225
<211> LENGTH: 120
<212> TYPE: PRT
<213> ORGANISM: Artificial Sequence
<220> FEATURE:
<223> OTHER INFORMATION: anti-TNF H1.10 variable region

<400> SEQUENCE: 225

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
                20                  25                  30

Trp Met Asn Trp Val Arg Gln Ala Ser Gly Lys Gly Leu Glu Trp Val
             35                  40                  45

Gly Glu Ile Arg Ser Lys Ser Ile Asn Tyr Ala Thr His Tyr Ala Glu
         50                  55                  60

Ser Val Lys Gly Arg Phe Thr Ile Ser Arg Asp Asp Ser Lys Ser Ile
 65                  70                  75                  80

Val Tyr Leu Gln Met Asn Ser Leu Lys Thr Glu Asp Thr Ala Val Tyr
                 85                  90                  95

Tyr Cys Ser Arg Asn Tyr Tyr Gly Ser Thr Tyr Asp Tyr Trp Gly Gln
                100                 105                 110

Gly Thr Leu Val Thr Val Ser Ser
            115                 120
```

<210> SEQ ID NO 226
<211> LENGTH: 120
<212> TYPE: PRT
<213> ORGANISM: Artificial Sequence
<220> FEATURE:
<223> OTHER INFORMATION: anti-TNF H1.11 variable region

<400> SEQUENCE: 226

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
            20                  25                  30

Trp Met Asn Trp Val Arg Gln Ala Ser Gly Lys Gly Leu Glu Trp Val
        35                  40                  45

Gly Glu Ile Arg Ser Lys Ser Ile Asn Ser Ala Thr Ala Tyr Ala Glu
    50                  55                  60

Ser Val Lys Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
        115                 120

<210> SEQ ID NO 227
<211> LENGTH: 120
<212> TYPE: PRT
<213> ORGANISM: Artificial Sequence
<220> FEATURE:
<223> OTHER INFORMATION: anti-TNF H1.12 variable region

<400> SEQUENCE: 227

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
            20                  25                  30

Trp Met Asn Trp Val Arg Gln Ala Ser Gly Lys Gly Leu Glu Trp Val
        35                  40                  45

Gly Glu Ile Arg Ser Lys Ser Ile Asn Ser Ala Thr His Tyr Ala Ala
    50                  55                  60

Ser Val Lys Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
        115                 120

<210> SEQ ID NO 228
<211> LENGTH: 120
<212> TYPE: PRT
<213> ORGANISM: Artificial Sequence
<220> FEATURE:
<223> OTHER INFORMATION: anti-TNF H1.13 variable region

<400> SEQUENCE: 228

Glu Val Gln Leu Val Glu Ser Gly Gly Gly Leu Val Gln Pro Gly Gly
1               5                   10                  15

```
Ser Leu Lys Leu Ser Cys Ala Ala Ser Gly Phe Ile Phe Ser Asn His
            20                  25                  30

Trp Met Asn Trp Val Arg Gln Ala Ser Gly Lys Gly Leu Glu Trp Val
        35                  40                  45

Gly Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Asn Ile
65                  70                  75                  80

Val Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
        115                 120
```

<210> SEQ ID NO 229
<211> LENGTH: 120
<212> TYPE: PRT
<213> ORGANISM: Artificial Sequence
<220> FEATURE:
<223> OTHER INFORMATION: anti-TNF H1.14 variable region

<400> SEQUENCE: 229

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
            20                  25                  30

Trp Met Asn Trp Val Arg Gln Ala Ser Gly Lys Gly Leu Glu Trp Val
        35                  40                  45

Gly Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Thr
65                  70                  75                  80

Val Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
        115                 120
```

<210> SEQ ID NO 230
<211> LENGTH: 120
<212> TYPE: PRT
<213> ORGANISM: Artificial Sequence
<220> FEATURE:
<223> OTHER INFORMATION: anti-TNF H1.15 variable region

<400> SEQUENCE: 230

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
            20                  25                  30

Trp Met Asn Trp Val Arg Gln Ala Ser Gly Lys Gly Leu Glu Trp Val
        35                  40                  45

Gly Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ile
65                  70                  75                  80
```

```
Ala Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
        115                 120

<210> SEQ ID NO 231
<211> LENGTH: 120
<212> TYPE: PRT
<213> ORGANISM: Artificial Sequence
<220> FEATURE:
<223> OTHER INFORMATION: anti-TNF H1.16 variable region

<400> SEQUENCE: 231

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
            20                  25                  30

Trp Met Asn Trp Val Arg Gln Ala Ser Gly Lys Gly Leu Glu Trp Val
        35                  40                  45

Gly Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Thr Arg Asn Tyr Tyr Gly Ser Thr Tyr Asp Tyr Trp Gly Gln
            100                 105                 110

Gly Thr Leu Val Thr Val Ser Ser
        115                 120

<210> SEQ ID NO 232
<211> LENGTH: 120
<212> TYPE: PRT
<213> ORGANISM: Artificial Sequence
<220> FEATURE:
<223> OTHER INFORMATION: anti-TNF H1.45 variable region

<400> SEQUENCE: 232

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
            20                  25                  30

Trp Met Asn Trp Val Arg Gln Ala Ser Gly Lys Gly Leu Glu Trp Val
        35                  40                  45

Gly Glu Ile Arg Ser Lys Ala Ile Asn Tyr Ala Thr His Tyr Ala Glu
    50                  55                  60

Ser Val Lys Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
        115                 120

<210> SEQ ID NO 233
```

```
<211> LENGTH: 120
<212> TYPE: PRT
<213> ORGANISM: Artificial Sequence
<220> FEATURE:
<223> OTHER INFORMATION: anti-TNF H1.67 variable region

<400> SEQUENCE: 233

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn His
            20                  25                  30

Trp Met Asn Trp Val Arg Gln Ala Ser Gly Lys Gly Leu Glu Trp Val
        35                  40                  45

Gly Glu Ile Arg Ser Lys Ala Ile Ser Tyr Ala Thr His Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
        115                 120

<210> SEQ ID NO 234
<211> LENGTH: 120
<212> TYPE: PRT
<213> ORGANISM: Artificial Sequence
<220> FEATURE:
<223> OTHER INFORMATION: anti-TNF H1.101 variable region

<400> SEQUENCE: 234

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
            20                  25                  30

Trp Met Asn Trp Val Arg Gln Ala Ser Gly Lys Gly Leu Glu Trp Val
        35                  40                  45

Gly Glu Ile Arg Ser Lys Ala Ile Asn Tyr Ala Thr His Tyr Ala Glu
    50                  55                  60

Ser Val Lys Gly Arg Phe Thr Ile Ser Arg Asp Asp Ser Lys Ser Thr
65                  70                  75                  80

Ala Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
        115                 120

<210> SEQ ID NO 235
<211> LENGTH: 120
<212> TYPE: PRT
<213> ORGANISM: Artificial Sequence
<220> FEATURE:
<223> OTHER INFORMATION: anti-TNF H1.103 variable region

<400> SEQUENCE: 235

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
```

```
                  20                  25                  30

Trp Met Asn Trp Val Arg Gln Ala Ser Gly Lys Gly Leu Glu Trp Val
            35                  40                  45

Gly Glu Ile Arg Ser Lys Ala Asn Asn Tyr Ala Thr His Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
        115                 120

<210> SEQ ID NO 236
<211> LENGTH: 107
<212> TYPE: PRT
<213> ORGANISM: Mus musculus

<400> SEQUENCE: 236

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys
            100                 105

<210> SEQ ID NO 237
<211> LENGTH: 107
<212> TYPE: PRT
<213> ORGANISM: Artificial Sequence
<220> FEATURE:
<223> OTHER INFORMATION: framework-optimized anti-TNF (L1) variable
      region light chain

<400> SEQUENCE: 237

Asp Ile Leu Leu Thr Gln Ser Pro Asp Phe Gln Ser Val Thr Pro Lys
1               5                   10                  15

Glu Lys Val Thr Ile Thr Cys Arg Ala Ser Gln Phe Val Gly Ser Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Trp Pro Phe
                85                  90                  95

Thr Phe Gly Ser Gly Thr Lys Leu Glu Ile Lys
            100                 105
```

```
<210> SEQ ID NO 238
<211> LENGTH: 107
<212> TYPE: PRT
<213> ORGANISM: Artificial Sequence
<220> FEATURE:
<223> OTHER INFORMATION: anti-TNF L1.1 variable region light chain

<400> SEQUENCE: 238

Glu Ile Leu Leu Thr Gln Ser Pro Asp Phe Gln Ser Val Thr Pro Lys
1               5                   10                  15

Glu Lys Val Thr Ile Thr Cys Arg Ala Ser Gln Phe Val Gly Ser Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Trp Pro Phe
                85                  90                  95

Thr Phe Gly Ser Gly Thr Lys Leu Glu Ile Lys
            100                 105

<210> SEQ ID NO 239
<211> LENGTH: 107
<212> TYPE: PRT
<213> ORGANISM: Artificial Sequence
<220> FEATURE:
<223> OTHER INFORMATION: anti-TNF L1.2 variable region light chain

<400> SEQUENCE: 239

Asp Ile Val Leu Thr Gln Ser Pro Asp Phe Gln Ser Val Thr Pro Lys
1               5                   10                  15

Glu Lys Val Thr Ile Thr Cys Arg Ala Ser Gln Phe Val Gly Ser Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Trp Pro Phe
                85                  90                  95

Thr Phe Gly Ser Gly Thr Lys Leu Glu Ile Lys
            100                 105

<210> SEQ ID NO 240
<211> LENGTH: 107
<212> TYPE: PRT
<213> ORGANISM: Artificial Sequence
<220> FEATURE:
<223> OTHER INFORMATION: anti-TNF L1.3 variable region light chain

<400> SEQUENCE: 240

Asp Ile Leu Leu Thr Gln Ser Pro Asp Phe Gln Ser Val Thr Pro Lys
1               5                   10                  15

Glu Lys Val Thr Ile Thr Cys Arg Ala Ser Gln Ser Val Gly Ser Ser
            20                  25                  30

Ile His Trp Tyr Gln Gln Lys Pro Asp Gln Ser Pro Lys Leu Leu Ile
```

```
                35                  40                  45
Lys Tyr Ala Ser Glu Ser Met Ser Gly Ile Pro Ser Arg Phe Ser Gly
         50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Ser His Ser Trp Pro Phe
                 85                  90                  95

Thr Phe Gly Ser Gly Thr Lys Leu Glu Ile Lys
            100                 105

<210> SEQ ID NO 241
<211> LENGTH: 107
<212> TYPE: PRT
<213> ORGANISM: Artificial Sequence
<220> FEATURE:
<223> OTHER INFORMATION: anti-TNF L1.4 variable region light chain

<400> SEQUENCE: 241

Asp Ile Leu Leu Thr Gln Ser Pro Asp Phe Gln Ser Val Thr Pro Lys
 1               5                  10                  15

Glu Lys Val Thr Ile Thr Cys Arg Ala Ser Gln Phe Ile Gly Ser Ser
             20                  25                  30

Ile His Trp Tyr Gln Gln Lys Pro Asp Gln Ser Pro Lys Leu Leu Ile
         35                  40                  45

Lys Tyr Ala Ser Glu Ser Met Ser Gly Ile Pro Ser Arg Phe Ser Gly
     50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Ser His Ser Trp Pro Phe
                 85                  90                  95

Thr Phe Gly Ser Gly Thr Lys Leu Glu Ile Lys
            100                 105

<210> SEQ ID NO 242
<211> LENGTH: 107
<212> TYPE: PRT
<213> ORGANISM: Artificial Sequence
<220> FEATURE:
<223> OTHER INFORMATION: anti-TNF L1.7 variable region light chain

<400> SEQUENCE: 242

Asp Ile Leu Leu Thr Gln Ser Pro Asp Phe Gln Ser Val Thr Pro Lys
 1               5                  10                  15

Glu Lys Val Thr Ile Thr Cys Arg Ala Ser Gln Phe Val Gly Ser Ser
             20                  25                  30

Ile His Trp Tyr Gln Gln Lys Pro Asp Gln Ser Pro Lys Leu Leu Ile
         35                  40                  45

Lys Tyr Ala Ser Glu Ser Phe Ser Gly Ile Pro Ser Arg Phe Ser Gly
     50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Ser His Ser Trp Pro Phe
                 85                  90                  95

Thr Phe Gly Ser Gly Thr Lys Leu Glu Ile Lys
            100                 105

<210> SEQ ID NO 243
<211> LENGTH: 107
<212> TYPE: PRT
```

<213> ORGANISM: Artificial Sequence
<220> FEATURE:
<223> OTHER INFORMATION: anti-TNF L1.8 variable region light chain

<400> SEQUENCE: 243

| Asp | Ile | Leu | Leu | Thr | Gln | Ser | Pro | Asp | Phe | Gln | Ser | Val | Thr | Pro | Lys |
|---|---|---|---|---|---|---|---|---|---|---|---|---|---|---|---|
| 1 | | | | 5 | | | | | 10 | | | | | 15 | |

| Glu | Lys | Val | Thr | Ile | Thr | Cys | Arg | Ala | Ser | Gln | Phe | Val | Gly | Ser | Ser |
|---|---|---|---|---|---|---|---|---|---|---|---|---|---|---|---|
| | | | 20 | | | | | 25 | | | | | 30 | | |

| Ile | His | Trp | Tyr | Gln | Gln | Lys | Pro | Asp | Gln | Ser | Pro | Lys | Leu | Leu | Ile |
|---|---|---|---|---|---|---|---|---|---|---|---|---|---|---|---|
| | | | 35 | | | | | 40 | | | | | 45 | | |

| Lys | Tyr | Ala | Ser | Glu | Ser | Met | Ser | Gly | Val | Pro | Ser | Arg | Phe | Ser | Gly |
|---|---|---|---|---|---|---|---|---|---|---|---|---|---|---|---|
| 50 | | | | | 55 | | | | | 60 | | | | | |

| Ser | Gly | Ser | Gly | Thr | Asp | Phe | Thr | Leu | Thr | Ile | Asn | Ser | Leu | Glu | Ala |
|---|---|---|---|---|---|---|---|---|---|---|---|---|---|---|---|
| 65 | | | | | 70 | | | | | 75 | | | | | 80 |

| Glu | Asp | Ala | Ala | Thr | Tyr | Tyr | Cys | Gln | Gln | Ser | His | Ser | Trp | Pro | Phe |
|---|---|---|---|---|---|---|---|---|---|---|---|---|---|---|---|
| | | | | 85 | | | | | 90 | | | | | 95 | |

| Thr | Phe | Gly | Ser | Gly | Thr | Lys | Leu | Glu | Ile | Lys |
|---|---|---|---|---|---|---|---|---|---|---|
| | | | 100 | | | | | 105 | | |

<210> SEQ ID NO 244
<211> LENGTH: 107
<212> TYPE: PRT
<213> ORGANISM: Artificial Sequence
<220> FEATURE:
<223> OTHER INFORMATION: anti-TNF L1.9 variable region light chain

<400> SEQUENCE: 244

| Asp | Ile | Leu | Leu | Thr | Gln | Ser | Pro | Asp | Phe | Gln | Ser | Val | Thr | Pro | Lys |
|---|---|---|---|---|---|---|---|---|---|---|---|---|---|---|---|
| 1 | | | | 5 | | | | | 10 | | | | | 15 | |

| Glu | Lys | Val | Thr | Ile | Thr | Cys | Arg | Ala | Ser | Gln | Phe | Val | Gly | Ser | Ser |
|---|---|---|---|---|---|---|---|---|---|---|---|---|---|---|---|
| | | | 20 | | | | | 25 | | | | | 30 | | |

| Ile | His | Trp | Tyr | Gln | Gln | Lys | Pro | Asp | Gln | Ser | Pro | Lys | Leu | Leu | Ile |
|---|---|---|---|---|---|---|---|---|---|---|---|---|---|---|---|
| | | | 35 | | | | | 40 | | | | | 45 | | |

| Lys | Tyr | Ala | Ser | Glu | Ser | Met | Ser | Gly | Ile | Pro | Ser | Arg | Phe | Ser | Gly |
|---|---|---|---|---|---|---|---|---|---|---|---|---|---|---|---|
| 50 | | | | | 55 | | | | | 60 | | | | | |

| Ser | Gly | Ser | Gly | Thr | Asp | Phe | Thr | Leu | Thr | Ile | Asn | Ser | Leu | Glu | Ala |
|---|---|---|---|---|---|---|---|---|---|---|---|---|---|---|---|
| 65 | | | | | 70 | | | | | 75 | | | | | 80 |

| Glu | Asp | Ala | Ala | Thr | Tyr | Tyr | Cys | His | Gln | Ser | His | Ser | Trp | Pro | Phe |
|---|---|---|---|---|---|---|---|---|---|---|---|---|---|---|---|
| | | | | 85 | | | | | 90 | | | | | 95 | |

| Thr | Phe | Gly | Ser | Gly | Thr | Lys | Leu | Glu | Ile | Lys |
|---|---|---|---|---|---|---|---|---|---|---|
| | | | 100 | | | | | 105 | | |

<210> SEQ ID NO 245
<211> LENGTH: 107
<212> TYPE: PRT
<213> ORGANISM: Artificial Sequence
<220> FEATURE:
<223> OTHER INFORMATION: anti-TNF L1.10 variable region light chain

<400> SEQUENCE: 245

| Asp | Ile | Leu | Leu | Thr | Gln | Ser | Pro | Asp | Phe | Gln | Ser | Val | Thr | Pro | Lys |
|---|---|---|---|---|---|---|---|---|---|---|---|---|---|---|---|
| 1 | | | | 5 | | | | | 10 | | | | | 15 | |

| Glu | Lys | Val | Thr | Ile | Thr | Cys | Arg | Ala | Ser | Gln | Phe | Val | Gly | Ser | Ser |
|---|---|---|---|---|---|---|---|---|---|---|---|---|---|---|---|
| | | | 20 | | | | | 25 | | | | | 30 | | |

| Ile | His | Trp | Tyr | Gln | Gln | Lys | Pro | Asp | Gln | Ser | Pro | Lys | Leu | Leu | Ile |
|---|---|---|---|---|---|---|---|---|---|---|---|---|---|---|---|
| | | | 35 | | | | | 40 | | | | | 45 | | |

| Lys | Tyr | Ala | Ser | Glu | Ser | Met | Ser | Gly | Ile | Pro | Ser | Arg | Phe | Ser | Gly |
|---|---|---|---|---|---|---|---|---|---|---|---|---|---|---|---|
| 50 | | | | | 55 | | | | | 60 | | | | | |

-continued

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Ser Ser Trp Pro Phe
                85                  90                  95

Thr Phe Gly Ser Gly Thr Lys Leu Glu Ile Lys
            100                 105

<210> SEQ ID NO 246
<211> LENGTH: 107
<212> TYPE: PRT
<213> ORGANISM: Artificial Sequence
<220> FEATURE:
<223> OTHER INFORMATION: anti-TNF L1.11 variable region light chain

<400> SEQUENCE: 246

Asp Ile Leu Leu Thr Gln Ser Pro Asp Phe Gln Ser Val Thr Pro Lys
1               5                   10                  15

Glu Lys Val Thr Ile Thr Cys Arg Ala Ser Gln Phe Val Gly Ser Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Met Ser Gly Ile Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Leu Pro Phe
                85                  90                  95

Thr Phe Gly Ser Gly Thr Lys Leu Glu Ile Lys
            100                 105

<210> SEQ ID NO 247
<211> LENGTH: 107
<212> TYPE: PRT
<213> ORGANISM: Artificial Sequence
<220> FEATURE:
<223> OTHER INFORMATION: anti-TNF L1.12 variable region light chain

<400> SEQUENCE: 247

Asp Ile Leu Leu Thr Gln Ser Pro Asp Phe Gln Ser Val Thr Pro Lys
1               5                   10                  15

Glu Lys Val Thr Ile Thr Cys Arg Ala Ser Gln Phe Val Gly Ser Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Ala Ser Gly Ile Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Trp Pro Phe
                85                  90                  95

Thr Phe Gly Ser Gly Thr Lys Leu Glu Ile Lys
            100                 105

<210> SEQ ID NO 248
<211> LENGTH: 107
<212> TYPE: PRT
<213> ORGANISM: Artificial Sequence
<220> FEATURE:
<223> OTHER INFORMATION: anti-TNF L1.13 variable region light chain

<400> SEQUENCE: 248

```
Asp Ile Leu Leu Thr Gln Ser Pro Asp Phe Gln Ser Val Thr Pro Lys
1               5                   10                  15

Glu Lys Val Thr Ile Thr Cys Arg Ala Ser Gln Phe Val Gly Ser Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Gln Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Trp Pro Phe
                85                  90                  95

Thr Phe Gly Ser Gly Thr Lys Leu Glu Ile Lys
            100                 105
```

<210> SEQ ID NO 249
<211> LENGTH: 107
<212> TYPE: PRT
<213> ORGANISM: Artificial Sequence
<220> FEATURE:
<223> OTHER INFORMATION: anti-TNF L1.14 variable region light chain

<400> SEQUENCE: 249

```
Asp Ile Leu Leu Thr Gln Ser Pro Asp Phe Gln Ser Val Thr Pro Lys
1               5                   10                  15

Glu Lys Val Thr Ile Thr Cys Arg Ala Ser Gln Phe Val Gly Ser Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Tyr Ser Trp Pro Phe
                85                  90                  95

Thr Phe Gly Ser Gly Thr Lys Leu Glu Ile Lys
            100                 105
```

<210> SEQ ID NO 250
<211> LENGTH: 107
<212> TYPE: PRT
<213> ORGANISM: Artificial Sequence
<220> FEATURE:
<223> OTHER INFORMATION: anti-TNF L1.15 variable region light chain

<400> SEQUENCE: 250

```
Asp Ile Leu Leu Thr Gln Ser Pro Asp Phe Gln Ser Val Thr Pro Lys
1               5                   10                  15

Glu Lys Val Thr Ile Thr Cys Arg Ala Ser Gln Phe Val Gly Ser Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Thr Pro Phe
                85                  90                  95
```

Thr Phe Gly Ser Gly Thr Lys Leu Glu Ile Lys
            100                 105

<210> SEQ ID NO 251
<211> LENGTH: 107
<212> TYPE: PRT
<213> ORGANISM: Artificial Sequence
<220> FEATURE:
<223> OTHER INFORMATION: anti-TNF L1.30 variable region light chain

<400> SEQUENCE: 251

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Phe Val Gly Ser Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Trp Pro Phe
                85                  90                  95

Thr Phe Gly Ser Gly Thr Lys Leu Glu Ile Lys
            100                 105

<210> SEQ ID NO 252
<211> LENGTH: 107
<212> TYPE: PRT
<213> ORGANISM: Artificial Sequence
<220> FEATURE:
<223> OTHER INFORMATION: anti-TNF L1.33 variable region light chain

<400> SEQUENCE: 252

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Phe Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Glu Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Trp Pro Phe
                85                  90                  95

Thr Phe Gly Ser Gly Thr Lys Leu Glu Ile Lys
            100                 105

<210> SEQ ID NO 253
<211> LENGTH: 5
<212> TYPE: PRT
<213> ORGANISM: Artificial Sequence
<220> FEATURE:
<223> OTHER INFORMATION: anti-TNF heavy chain CDR1

<400> SEQUENCE: 253

Asn His Trp Met Asn
1               5

```
<210> SEQ ID NO 254
<211> LENGTH: 19
<212> TYPE: PRT
<213> ORGANISM: Artificial Sequence
<220> FEATURE:
<223> OTHER INFORMATION: anti-TNF heavy chain CDR2

<400> SEQUENCE: 254

Glu Ile Arg Ser Lys Ser Ile Asn Ser Ala Thr His Tyr Ala Glu Ser
1               5                   10                  15

Val Lys Gly

<210> SEQ ID NO 255
<211> LENGTH: 19
<212> TYPE: PRT
<213> ORGANISM: Artificial Sequence
<220> FEATURE:
<223> OTHER INFORMATION: anti-TNF heavy chain CDR2

<400> SEQUENCE: 255

Glu Ile Arg Ser Lys Ala Ile Asn Tyr Ala Thr His Tyr Ala Glu Ser
1               5                   10                  15

Val Lys Gly

<210> SEQ ID NO 256
<211> LENGTH: 19
<212> TYPE: PRT
<213> ORGANISM: Artificial Sequence
<220> FEATURE:
<223> OTHER INFORMATION: anti-TNF heavy chain CDR2

<400> SEQUENCE: 256

Glu Ile Arg Ser Lys Ala Ile Ser Tyr Ala Thr His Tyr Ala Ala Ser
1               5                   10                  15

Val Lys Gly

<210> SEQ ID NO 257
<211> LENGTH: 19
<212> TYPE: PRT
<213> ORGANISM: Artificial Sequence
<220> FEATURE:
<223> OTHER INFORMATION: anti-TNF heavy chain CDR2

<400> SEQUENCE: 257

Glu Ile Arg Ser Lys Ala Asn Asn Tyr Ala Thr His Tyr Ala Ala Ser
1               5                   10                  15

Val Lys Gly

<210> SEQ ID NO 258
<211> LENGTH: 9
<212> TYPE: PRT
<213> ORGANISM: Artificial Sequence
<220> FEATURE:
<223> OTHER INFORMATION: anti-TNF heavy chain CDR3

<400> SEQUENCE: 258

Asn Tyr Tyr Gly Ser Thr Tyr Asp Tyr
1               5

<210> SEQ ID NO 259
<211> LENGTH: 11
<212> TYPE: PRT
<213> ORGANISM: Artificial Sequence
<220> FEATURE:
<223> OTHER INFORMATION: anti-TNF light chain CDR1
```

```
<400> SEQUENCE: 259

Arg Ala Ser Gln Phe Val Gly Ser Ser Ile His
1               5                   10

<210> SEQ ID NO 260
<211> LENGTH: 11
<212> TYPE: PRT
<213> ORGANISM: Artificial Sequence
<220> FEATURE:
<223> OTHER INFORMATION: anti-TNF light chain CDR1

<400> SEQUENCE: 260

Arg Ala Ser Gln Phe Val Gly Ser Ser Ile His
1               5                   10

<210> SEQ ID NO 261
<211> LENGTH: 11
<212> TYPE: PRT
<213> ORGANISM: Artificial Sequence
<220> FEATURE:
<223> OTHER INFORMATION: anti-TNF light chain CDR1

<400> SEQUENCE: 261

Arg Ala Ser Gln Phe Ile Gly Ser Ser Leu His
1               5                   10

<210> SEQ ID NO 262
<211> LENGTH: 7
<212> TYPE: PRT
<213> ORGANISM: Artificial Sequence
<220> FEATURE:
<223> OTHER INFORMATION: anti-TNF light chain CDR2

<400> SEQUENCE: 262

Tyr Ala Ser Glu Ser Met Ser
1               5

<210> SEQ ID NO 263
<211> LENGTH: 7
<212> TYPE: PRT
<213> ORGANISM: Artificial Sequence
<220> FEATURE:
<223> OTHER INFORMATION: anti-TNF light chain CDR2

<400> SEQUENCE: 263

Tyr Ala Ser Glu Ser Phe Ser
1               5

<210> SEQ ID NO 264
<211> LENGTH: 9
<212> TYPE: PRT
<213> ORGANISM: Artificial Sequence
<220> FEATURE:
<223> OTHER INFORMATION: anti-TNF light chain CDR3

<400> SEQUENCE: 264

Gln Gln Ser His Ser Trp Pro Phe Thr
1               5

<210> SEQ ID NO 265
<211> LENGTH: 121
<212> TYPE: PRT
<213> ORGANISM: Artificial Sequence
<220> FEATURE:
<223> OTHER INFORMATION: Rituximab VH

<400> SEQUENCE: 265
```

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
            115                 120

<210> SEQ ID NO 266
<211> LENGTH: 120
<212> TYPE: PRT
<213> ORGANISM: Artificial Sequence
<220> FEATURE:
<223> OTHER INFORMATION: anti-TNF H1.11 variable region

<400> SEQUENCE: 266

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asn His
                20                  25                  30

Trp Met Asn Trp Val Arg Gln Ala Ser Gly Lys Gly Leu Glu Trp Val
            35                  40                  45

Gly Glu Ile Arg Ser Lys Ser Ile Asn Ser Ala Thr Ala Tyr Ala Glu
        50                  55                  60

Ser Val Lys Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Leu Val Thr Val Ser Ser
            115                 120
```